(12) United States Patent   (10) Patent No.: US 7,872,006 B2
Moritani et al.              (45) Date of Patent:     Jan. 18, 2011

(54) PYRAZOLE COMPOUNDS HAVING CANNABINOID RECEPTOR (CB1) ANTAGONIZING ACTIVITY

(75) Inventors: Yasunori Moritani, Osaka (JP); Ritsuo Imashiro, Osaka (JP); Atsushi Sato, Osaka (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 0 days.

(21) Appl. No.: 12/083,610

(22) PCT Filed: Oct. 20, 2006

(86) PCT No.: PCT/JP2006/321446

§ 371 (c)(1),
(2), (4) Date: Apr. 15, 2008

(87) PCT Pub. No.: WO2007/046550

PCT Pub. Date: Apr. 26, 2007

(65) Prior Publication Data

US 2009/0048256 A1     Feb. 19, 2009

Related U.S. Application Data

(60) Provisional application No. 60/729,205, filed on Oct. 24, 2005, provisional application No. 60/806,075, filed on Jun. 28, 2006.

(30) Foreign Application Priority Data

Oct. 21, 2005 (JP) .............................. 2005 306817
Jun. 20, 2006 (JP) .............................. 2006-169479

(51) Int. Cl.
A61K 31/5377 (2006.01)
A61K 31/496 (2006.01)
A61K 31/435 (2006.01)
A61K 31/4155 (2006.01)
C07D 413/02 (2006.01)
C07D 403/02 (2006.01)
C07D 401/02 (2006.01)
C07D 231/10 (2006.01)

(52) U.S. Cl. .............................. 514/236.5; 514/254.05; 514/341; 514/406; 544/140; 544/371; 546/275.4; 548/364.1; 548/373.1

(58) Field of Classification Search .................. 544/140, 544/371; 546/275.4; 548/364.1, 373.1; 514/236.5, 514/254.05, 341, 406
See application file for complete search history.

(56) References Cited

FOREIGN PATENT DOCUMENTS

EP     1 602 656 A1   12/2005

(Continued)

OTHER PUBLICATIONS

Lan, Ruoxi. Structure-Activity Relationships of Pyrazole Derivatives as Cannabinoid Receptor Antagonists. J. Med. Chem. 42 (1999) 769-776.*

(Continued)

*Primary Examiner*—Kamal A Saeed
*Assistant Examiner*—Samantha L Shterengarts
(74) *Attorney, Agent, or Firm*—Birch, Stewart, Kolasch & Birch, LLP

(57) ABSTRACT

The present invention relates to a pyrazole compound having potent CB1-antagonizing activity, having the following formula [I]:

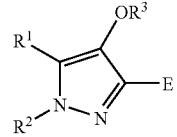

[I]

wherein
$R^1$ and $R^2$ are the same or different and an optionally substituted aryl group etc.,
$R^3$ is an alkyl group etc.,
E is one of the following groups of the formula (i) to (iv):

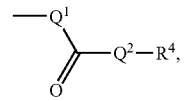

(i)

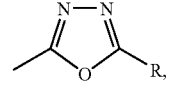

(ii)

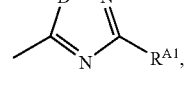

(iii)

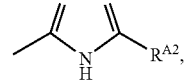

(iv)

$Q^1$ is a single bond, an alkylene group or a group of the formula: —$N(R^7)$—,
$R^7$ is a hydrogen atom or an alkyl group,
$Q^2$ is a single bond, an oxygen atom or an alkylene group,
$R^4$ is a cycloalkyl group, a group of the formula: —$N(R^5)(R^6)$ etc.,
one of $R^5$ and $R^6$ is a hydrogen atom or an alkyl group and the other is an alkyl group, a group of the formula: —$N(R^8)(R^9)$ etc.,
D is an oxygen atom etc.,
$R^{41}$ is an amino group etc.,
$R^{42}$ is an optionally substituted aliphatic heterocyclic group,
R is an alkyl group optionally substituted by one to three halogen atom(s) etc.,
one of $R^8$ and $R^9$ is a hydrogen atom or an alkyl group and the other is an alkyl group etc., or a pharmaceutically acceptable salt thereof.

7 Claims, No Drawings

FOREIGN PATENT DOCUMENTS

| | | |
|---|---|---|
| WO | WO-03/0202017 A1 | 3/2003 |
| WO | WO-2004/094421 A1 | 11/2004 |
| WO | WO-2005/044822 A1 | 5/2005 |
| WO | WO-2005/080343 A2 | 9/2005 |
| WO | WO-2006/035310 A2 | 4/2006 |
| WO | WO-2006/133926 A1 | 12/2006 |

OTHER PUBLICATIONS

Golub et al. Science (1999), vol. 286 521-537.*
Lala et al. Cancer and Metastasis Reviews (1998), 17(1), 91-106.*
Mikael, et al., Database Caplus [online] Chemical Abstracts Service, Columbus, Ohio, Us; Begtrup; "Reactions of glyoxals with hydrazones: a new route to 4-hydroxypyrazoles", XP002416224 retrieved from STN Database accession No. 1985:166654.
Lisa A. Matsuda, et al., Structure of a cannabinoid receptor and functional expression of the cloned cDNA, Nature, vol. 346, Aug. 9, 1990, pp. 561-564.
Sean Munro, et al., Molecular characterization of a peripheral receptor for cannabinoids, Nature, vol. 365, Sep. 2, 1993, pp. 61-65.
Giancarlo Colombo, et al., Appetite Suppression and Weight Loss After the Cannabinoid Antagonist SR 141716, Life Science, vol. 63, No. 8, Jun. 2, 1998, pp. PL113-PL117.
Jos H. M. Lange, et al., Synthesis, Biological Properties, and Molecular Modeling Investigations of Novel 3,4-Diarylpyrazolines as Potent and Selective CB1 Cannabinoid Receptor Antagonists, Journal of Medicinal Chemistry, vol. 47(3), 2004, pp. 627-643.

* cited by examiner

PYRAZOLE COMPOUNDS HAVING CANNABINOID RECEPTOR (CB1) ANTAGONIZING ACTIVITY

This application is the National Phase of PCT/JP2006/321446 filed on Oct. 20, 2006, which claims priority under 35 U.S.C. 119(e) to U.S. Provisional Application No. 60/729,205 filed on Oct. 24, 2005 and U.S. Provisional Application No. 60/806,075 filed on Jun. 28, 2006 and under 35 U.S.C. 119(a) to Patent Application No. 2005-306817 filed in Japan on Oct. 21, 2005 and to Patent Application No. 2006-169479 filed in Japan on Jun. 20, 2006. All of these prior applications are hereby expressly incorporated by reference into the present application.

TECHNICAL FIELD

The present invention relates to a novel pyrazole compound or a pharmaceutically acceptable salt thereof which has potent central cannabinoid receptor (CB1) antagonizing activity and hence is useful as a medicine.

BACKGROUND ART

It is well known that, by intake of marijuana, various psychiatric or neurological reactions such as confusion of temporal or space sense, euphoria, alteration of memories, analgesia, hallucination and the like would be produced. The compounds generally referred to as "cannabinoid" including Δ9-tetrahydrocannabinol (Δ9-THC) are responsible for many of such reactions. The effect of cannabinoid is considered to be produced by an interaction between the compound and its endogenous specific/high-affinity receptors. Two subtypes of cannabinoid receptors (CB1 and CB2) have been identified and cloned. The CB1 receptor is distributed in central nervous system (CNS) regions including brain (Non-patent literature 1) while the CB2 receptor is distributed in immune system including spleen (Non-patent literature 2).

Substances having affinity to such cannabinoid receptors (agonists, antagonists or inverse agonists) may produce various pharmacological effects like marijuana. In particular, substances having affinity to central CB1 receptor may be useful for treatment of a CNS disease such as a psychotic disorder, a neurological disorder and the like.

There have been known various compounds, including pyrazol-3-carboxamide compounds such as SR141716 (Non-patent literature 3), 4,5-dihydropyrazole compounds such as SLV-319 (Non-patent literature 4), dihydropyrazolo[3,4-c]pyridin-7-one compounds, 2H-pyrazolo[4,3-d]pyrimidin-7(6H)-one (Patent literature 1) and the like as the substances having affinity to such cannabinoid receptors. Among them, at least SR141716 and SLV-319 are under clinical studies on the efficacy thereof as anorexigenics (anti-obesity agent).

(Patent literature 1) WO2004/094417
(Non-patent literature 1) Nature, Vol. 346, 1990, pp 561-564
(Non-patent literature 2) Nature, Vol. 365, 1993, pp 61-65
(Non-patent literature 3) Life Science, Vol. 63, 1998, PL113-PL117
(Non-patent literature 4) Journal of Medicinal Chemistry, Vol. 47(3), 2004, pp. 627-643

DISCLOSURE OF INVENTION

The object of the present invention is to provide a novel pyrazole compound which has potent CB1 receptor-antagonizing activity and hence is useful as a medicine.

MEANS TO SOLVE THE PROBLEM

The present invention relates to a pyrazole compound of the formula [I]:

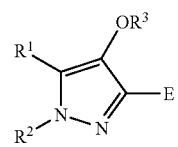

wherein $R^1$ and $R^2$ are the same or different and an optionally substituted aryl group or an optionally substituted heteroaryl group, $R^3$ is (a) a hydrogen atom, (b) an alkyl group optionally substituted by one to three group(s) selected from a halogen atom, a cyano group, an alkyloxy group, an alkyloxycarbonyl group, an amino group optionally substituted by one to two alkyl group(s), an acylamino group, an alkylcarbamoylamino group, an alkylsulfonyl-amino group, a di(alkyl)amino-sulfonylamino group, a carbamoyl group optionally substituted by one to two alkyl group(s), an alkyloxycarbonyl group, an alkylthio group, an alkylsulfinyl group, an alkylsulfonyl group and an optionally substituted saturated or unsaturated heterocyclic group, (c) an aminosulfonyl group optionally substituted by one to two alkyl group(s), or (d) an optionally substituted saturated or unsaturated heterocyclic group, or (e) $R^3$ combines with $R^1$ to form, together with $R^1$, an adjacent oxygen atom and a pyrazole ring, a ring group of the following formula:

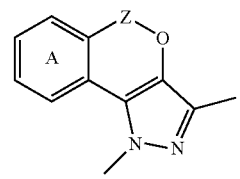

Ring A is an optionally substituted aryl (or heteroaryl) group, -Z-O— is a group of the formula: —$(CH_2)_m$—O—; —O—$(CH_2)_n$—O—; or —N($R^O$)—$(CH_2)_n$—O—, $R^O$ is a hydrogen atom or an alkyl group, m is an integer of 1 to 3, n is an integer of 2 to 3, E is one of the groups of the following formula (i) to (iv):

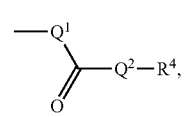

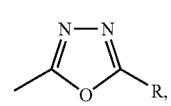

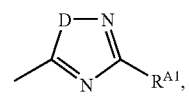

-continued

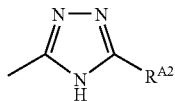

(iv)

$Q^1$ is a single bond, an alkylene group or a group of the formula: —N($R^7$)—, $R^7$ is a hydrogen atom or an alkyl group, $Q^2$ is a single bond, an oxygen atom or an alkylene group, $R^4$ is a cycloalkyl group, a group of the formula: —N($R^5$)($R^6$), an optionally substituted aryl group or an optionally substituted saturated or unsaturated heterocyclic group, one of $R^5$ and $R^6$ is a hydrogen atom or an alkyl group and the other is (a) an alkyl group optionally substituted by a halogen atom, an amino group, an alkylthio group, an alkylsulfinyl group, an alkylsulfonyl group and an optionally substituted aryl group, (b) an optionally substituted cycloalkyl group, (c) a group of the formula: —N($R^8$)($R^9$), (d) an optionally substituted aryl group or (e) an optionally substituted, saturated or unsaturated heterocyclic group, one of $R^8$ and $R^9$ is a hydrogen atom or an alkyl group and the other is (a) an alkyl group optionally substituted by one to two group(s) selected from an oxo group, a cyano group, an alkyloxy group, an acyl group and an optionally substituted aryl group, (b) a cycloalkyl group, (c) an acyl group, (d) an optionally substituted aryl group or (e) an optionally substituted saturated or unsaturated heterocyclic group, D is an oxygen atom or a group of the formula: —NH—, $R^{41}$ is an amino group or a group of the formula:

in which k is an integer of 3 to 5, $R^{42}$ is an optionally substituted aliphatic heterocyclic group, R is an alkyl group optionally substituted by one to three halogen atom(s), an alkyloxy-alkylcarbonyl group, an alkylthio group, an optionally substituted cycloalkyl group, an optionally substituted aryl group or an optionally substituted saturated or unsaturated heterocyclic group, or a pharmaceutically acceptable salt thereof.

BEST MODE TO CARRY OUT INVENTION

With regard to the compound [I] of the present invention, in case that $R^1$ (or Ring A) and $R^2$ are an aryl group, examples of such aryl group include a 6- to 10-membered mono- or bicyclic aryl group such as a phenyl group or a naphthyl group. Among them, preferred example of such aryl group is a phenyl group.

In case that $R^1$ (or Ring A) and $R^2$ are a heteroaryl group, examples of such heteroaryl group include a 5- to 6-membered oxygen-containing heteroaryl group such as a furyl group or a pyranyl group, a 5- to 6-membered sulfur-containing heteroaryl group such as thienyl group or a 5- to 6-membered nitrogen-containing heteroaryl group such as a pyridyl group. Among them, preferred example of such heteroaryl group is a thienyl group or a pyridyl group.

The aryl group and/or the heteroaryl group in Ring A, $R^1$ or $R^2$ mentioned above may be substituted by one to three group(s) selected from (a) a halogen atom, (b) a cyano group, (c) an alkyl group optionally substituted by one to three halogen atom(s), (d) an alkyloxy group optionally substituted by one to three halogen atom(s) and (e) a an alkylsulfonyl group.

Examples of the aryl group in R, $R^3$, $R^4$, $R^5$, $R^6$, $R^8$ or $R^9$ include a 6- to 10-membered mono- or bicyclic aryl group such as a phenyl group, a naphthyl group and the like, and among them, a phenyl group is preferable. Besides, such aryl group may be substituted by one to three group(s) selected from (a) a halogen atom, (b) a hydroxyl group, (c) a cyano group, (d) an oxo group, (e) an alkyl group optionally substituted by one to three halogen atom(s), (f) an alkyloxy-alkyl group, (g) an amino-alkyl group, (h) a cycloalkyl group, (i) an aryl-alkyl group, (j) an alkyloxy group optionally substituted by one to three halogen atom(s), (k) an amino group optionally substituted by one to two alkyl group(s), (l) a carbamoyl group optionally substituted by one to two alkyl group(s), (m) an acyl group, (n) an alkylthio group, (o) an alkylsulfinyl group, (p) an alkylsulfonyl group, (q) an aminosulfonyl group optionally substituted by one to two alkyl group(s), (r) an aryl-sulfonyl group, (s) an aryl group (said aryl group being optionally substituted by one to three group(s) selected from a halogen atom, a cyano group, an alkyl group optionally substituted by one to three halogen atom(s), an alkyl oxy group and an alkylsulfonyl group), and (t) a heteroaryl group.

In case that R, $R^3$, $R^4$, $R^5$, $R^6$, $R^8$ or $R^9$ is a saturated or unsaturated heterocyclic group, examples of such heterocyclic group include (a) a saturated or unsaturated, 4- to 7-membered heteromonocyclic group, said heteromonocyclic group containing one to four heteroatoms selected from oxygen atom, sulfur atom and nitrogen atom; (b) a saturated or unsaturated, 8- to 15-membered nitrogen-containing bicyclic or tricyclic heterocyclic group formed by fusing the aforementioned heteromonocyclic group with one or two other cyclic groups selected from a $C_{3-8}$ cycloalkyl group, a 5- to 6-membered monocyclic aryl group and a saturated or unsaturated, 4- to 7-membered heteromonocyclic group, said heteromonocyclic group containing one to four heteroatoms selected from oxygen atom, sulfur atom and nitrogen atom; or (c) a saturated or unsaturated, 8- to 11-membered nitrogen-containing spiro-heterocyclic group.

Examples of the saturated or unsaturated heterocyclic group in R, $R^3$, $R^4$, $R^5$, $R^6$, $R^8$ or $R^9$ is (A) a saturated or unsaturated oxygen- or sulfur-containing heterocyclic group selected from a furyl group, a tetrahydrofuranyl group, a pyranyl group, a tetrahydropyranyl group, a thienyl group, a tetrahydrothienyl group, a thiopyranyl group, a tetrahydrothiopyranyl group, a benzofuranyl group, a dihydrobenzofuranyl group, an isobenzofuranyl group, a chromanyl group, an isochromanyl group, a chromenyl group, an isochromenyl group, a benzothienyl group and a dihydrobenzothienyl group; or (B) a saturated or unsaturated nitrogen-containing heterocyclic group selected from an azetidyl group, a pyrrolidinyl group, a pyrrolinyl group, an imidazolidinyl group, an imidazolinyl group, a pyrazolidinyl group, a pyrazolinyl group, a pyrrolyl group, a 2H-pyrrolyl group, an imidazolyl group, a pyrazolyl group, a dihydropyrazolyl group, a thiazolidinyl group, an isothiazolidinyl group, an isoxazolyl group, an oxazolidinyl group, an oxadiazolyl group, a triazolyl group, a pyridyl group, a dihydropyridyl group, a tetrahydropyridyl group, a piperidyl group, a pyrazinyl group, a piperazinyl group, a pyrimidinyl group, a tetrahydropyrimidinyl group, a pyridazinyl group, a morpholinyl group, an azocinyl group, an azacycloheptyl group, an indolizinyl group, a benzimidazolyl group, a benzotriazolyl group, an indolyl group, an isoindolyl group, a 3H-indolyl group, a 1H-indazolyl group, a tetrazolyl group, a purinyl group, a pteridinyl group, a 4H-quinolizinyl group, a quinolyl group, a dihydroquinolyl group, a tetrahydroquinolyl group, an isoquinolyl group, a dihydroisoquinolyl group, a tetrahydroisoquinolyl group, a dihydrophthalazinyl group, a naphthyridinyl group, a quinoxalinyl group, a quinazolinyl group, a dihydroquinazolinyl group, a dihydrobenzothiazinyl group, a dihydrobenzoxazinyl group, a cinnolinyl group, a xanthenyl group, a carbazolyl group, a beta-carbolinyl group, a phenanthridinyl group, an acridinyl group, a 5H-dihydro-dibenzazepinyl group and a spiro-heterocyclic group of the formula:

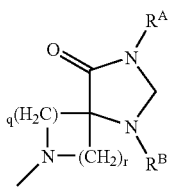

wherein $R^A$ and $R^B$ are the same or different and a hydrogen atom or an alkyl group, and q and r are an integer of 1 or 2.

Among them, preferred examples of the saturated or unsaturated heterocyclic group in R, $R^3$, $R^4$, $R^5$, $R^6$, $R^8$ or $R^9$ include a saturated or unsaturated, 5- to 7-membered, nitrogen-, oxygen- or sulfur-containing heteromonocyclic such as an azetidyl group, a pyrrolyl group, a pyrrolidinyl group, a piperidyl group, a pyridyl group, a piperazinyl group, a pyrimidinyl group, a pyrazinyl group, an azacycloheptyl group, a furyl group, a tetrahydropyranyl group, a tetrahydrothiopyranyl group, a piperazinyl group, a morpholinyl group, a thiomorpholinyl group, a thienyl group, a tetrahydrothienyl group, a thiazolyl group, an isothiazolyl group, an oxazolyl group, an isoxazolyl group, an oxadiazolyl group, a tetrazolyl group or a pyridyl group.

Moreover, the saturated or unsaturated nitrogen-containing heterocyclic group in R, $R^3$, $R^4$, $R^5$, $R^6$, $R^8$ and $R^9$ mentioned above may be substituted by one to four group(s) selected from (a) a halogen atom, (b) a hydroxyl group, (c) a cyano group, (d) an oxo group, (e) an alkyl group optionally substituted by one to three halogen atom(s), (f) an alkyloxyalkyl group, (g) an aminoalkyl group, (h) an alkylsulfinylalkyl group, (i) an alkylsulfonylalkyl group, (j) a cycloalkyl group, (k) an arylalkyl group, (l) an alkyloxy group optionally substituted by one to three halogen atom(s), (m) a carboxyl group, (n) an amino group optionally substituted by one to two group(s) selected from an alkyl group and an acyl group, (o) a carbamoyl group optionally substituted by one to two alkyl group(s), (p) an acyl group, (q) an alkylthio group, (r) an alkylsulfinyl group, (s) an alkylsulfonyl group, (t) an aminosulfonyl group optionally substituted by one to two alkyl group(s), (u) an aryl-sulfonyl group, (v) an aryl group optionally substituted by one to three group(s) selected from a halogen atom, a cyano group, an alkyl group optionally substituted by one to three halogen atom(s), an alkyloxy group and an alkylsulfonyl group and (w) a heteroaryl group optionally substituted by one to three group(s) selected from an alkyl group optionally substituted by one to three halogen atom(s), a halogen atom and a cyano group.

Examples of the acyl group in R, $R^3$, $R^4$, $R^5$, $R^6$, $R^8$ and $R^9$ include a group composed by removing a hydroxyl group from a carboxylic acid compound of the following formula: $R^x$—COOH [Ac-1], namely, a group of the formula: $R^x$—CO—, in which $R^x$ is (a) a hydrogen atom, (b) an alkyl group optionally substituted by one to three group(s) selected from a halogen atom, a cyano group and an alkylsulfonyl group, (c) an alkyloxy group optionally substituted by an aryl group, (d) a cycloalkyl group, (e) an aryl group optionally substituted by one to two group(s) selected from a halogen atom, a cyano group, an alkyl group, a trihalogenoalkyl group and an alkyloxy group, (f) an amino group optionally substituted by one to two alkyl group(s) or (g) a saturated or unsaturated heterocyclic group optionally substituted by one to two group(s) selected from a halogen atom, a cyano group, an alkyl group and a trihalogenoalkyl group. Concrete examples of such acyl group may be (a1) a formyl group, (b1) a $C_{1-6}$ alkyl-carbonyl group such as an acetyl group, a propionyl group and the like, a trihalogeno-$C_{1-6}$alkyl-carbonyl group such as a trifluoroacetyl group and the like, or a cyano-$C_{1-6}$ alkyl-carbonyl group such as a cyanoacetyl group, (c1) a $C_{1-6}$ alkyloxy-carbonyl group such as a methoxycarbonyl group, an ethoxycarbonyl group, a tert-butoxycarbonyl group and the like, or an aryl-$C_{1-6}$ alkyloxy-carbonyl group such as a benzyloxycarbonyl group, (d1) a $C_{3-8}$ cycloalkyl-carbonyl group such as a cyclopropylcarbonyl group, a cyclopentylcarbonyl group and the like, (e1) an arylcarbonyl group such as a benzoyl group, a mono- or di-halogeno-aryl-carbonyl group such as a chlorobenzoyl group, a fluorobenzoyl group, a difluorobenzoyl group and the like, a cyano-aryl-carbonyl group such as a cyanobenzoyl group, a trihalogeno-$C_{1-4}$ alkyl-aryl-carbonyl group such as a trifluoromethylbenzoyl group, or a trihalogeno-$C_{1-4}$ alkyloxy-aryl-carbonyl group such as a trifluoromethoxybenzoyl group, (f1) a carbamoyl group, a N—($C_{1-4}$ alkyl)-carbamoyl group or (g1) a furoyl group, a thenoyl group, a bromothenoyl group, a cyanothenoyl group, a pyridylcarbonyl group, a chloropyridylcarbonyl group, a cyanopyridylcarbonyl group, a trifluoromethylpyridyl-carbonyl group or a pyrazinylcarbonyl group.

Among the compounds [I] of the present invention, examples of preferred compound include a compound [I] in which $R^1$ and $R^2$ are the same or different and a phenyl group optionally substituted by one to two group(s) selected from a halogen atom, a cyano group, a trihalogenoalkyl group, an alkyloxy group, an alkylthio group, an alkylsulfinyl group and an alkylsulfonyl group, $R^3$ is (a) a hydrogen atom, (b) an alkyl group optionally substituted by one to three group(s) selected from a halogen atom, a cyano group, an alkyloxy group, an alkylthio group, an acyl group, an amino group, an acylamino group, a carbamoyl group, an alkylcarbamoylamino group, an alkylsulfonylamino group, a di(alkyl)amino-sulfonylamino group and a saturated or unsaturated 5- to 6-membered heterocyclic group (said heterocyclic group being optionally substituted by one to two group(s) selected from an oxo group and an alkyl group), (c) an aminosulfonyl group optionally substituted by one to two alkyl group(s) or (d) a saturated or unsaturated 5- to 6-membered heterocyclic group (said heterocyclic group being optionally substituted by one to two group(s) selected from an oxo group and an alkyl group), E is a group of the formula (i), $Q^1$ is a single bond or a group of the formula: —NH—, $Q^2$ is a single bond, an oxygen atom or an alkylene group, $R^4$ is (a) an aryl group optionally substituted by one to three group(s) selected from a halogen atom, a cyano group and an alkylsulfonyl group, (b) a cycloalkyl group, (c) a saturated or unsaturated 5- to 7-membered heteromonocyclic group optionally substituted by one to two group(s) selected from a halogen atom, an oxo group, a cyano group, an alkyl group optionally substituted by one to three halogen atom(s), an amino group optionally substituted by one to two alkyl group(s), a carbamoyl group and an acyl group, (d) a group of the formula: —N(R⁵)(R⁶) or (e) a spiro heterocyclic group of the formula:

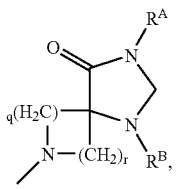

R⁵ is a hydrogen atom or an alkyl group,

R⁶ is (1) an alkyl group optionally substituted by one to three group(s) selected from a halogen atom, an amino group, an alkyloxy group, an alkylthio group, an alkylsulfinyl group, an alkylsulfonyl group and an aryl group; (2) a cycloalkyl group optionally substituted by a carbamoyl group; (3) a group of the formula: —N(R⁸)(R⁹), (4) an acyl group, (5) an aryl group optionally substituted by one to three group(s) selected from a halogen atom, a cyano group, a trihalogenoalkyl group and an alkyloxy group, or (6) a saturated or unsaturated 5- to 7-membered heteromonocyclic group optionally substituted by one to four group(s) selected from a halogen atom, an oxo group, an alkyl group optionally substituted by one to three halogen atom(s), an alkyloxyalkyl group, an aryl-alkyl group, an alkyloxy group optionally substituted by one to three halogen atom(s), an acyl group, a carboxyl group, a carbamoyl group, an alkylsulfonyl group, an aminosulfonyl group optionally substituted by one to two alkyl group(s), an aryl-sulfonyl group, an amino group optionally substituted by one to two group(s) selected from an alkyl group and an acyl group, an aryl group optionally substituted by one to two halogen atom(s) and a heteroaryl group optionally substituted by one to two group(s) selected from an alkyl group optionally substituted by one to three halogen atom(s), a halogen atom and a cyano group, R^A is a hydrogen atom, R^B is an alkyl group, q and r are an integer of 1, R⁸ is a hydrogen atom or an alkyl group and R⁹ is an alkyl group optionally substituted by one to two group(s) selected from an oxo group, a cyano group and an aryl group, an acyl group, an aryl group or a heteroaryl group.

Besides, among the compounds [I] of the present invention, examples of other preferred compound include:

(1) a compound [I] in which R¹ and R² are the same or different and a halogenophenyl group, R³ is an alkyl group or an alkyloxyalkyl group, E is a group of the formula (ii), R is (a) an alkyl group optionally substituted by one to three halogen atom(s), (b) an alkyloxyalkyl group, (c) a cycloalkyl group optionally substituted by a group selected from a hydroxyl group and an alkyl group, (d) an alkylthio group, (e) an aryl group optionally substituted by one to two group(s) selected from a halogen atom and a cyano group or (f) a saturated or unsaturated heterocyclic group optionally substituted by an alkylsulfonyl group, an acyl group and a heteroaryl group; or (2) a compound [I] in which R¹ and R² are the same or different and a halogenophenyl group, R³ is an alkyl group or an alkyloxyalkyl group, E is a group of the formula (iii) and R^{A1} is an amino group or a group of the formula:

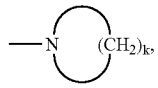

and k is an integer of 3 to 4; or (3) a compound [I] in which R¹ and R² are the same or different and a halogenophenyl group, R³ is an alkyl group or an alkyloxyalkyl group, E is a group of the formula (iv) and R^{A2} is a 4- to 7-membered nitrogen-containing aliphatic heterocyclic group optionally substituted by a pyrimidinyl group or a halogeno-pyrimidinyl group.

Among them, examples of more preferred compound include a compound [I] in which

R¹ is a phenyl group substituted by one to two group(s) selected from a halogen atom and a trihalogeno-$C_{1-4}$ alkyl group, R² is a phenyl group substituted by one to two halogen atoms, R³ is a $C_{1-4}$ alkyl group optionally substituted by one to three halogen atom(s), a $C_{1-4}$ alkyloxy-$C_{1-4}$ alkyl group, a cyano-$C_{1-4}$ alkyloxy group, an amino-$C_{1-4}$ alkyl group (the amino moiety of said group being optionally substituted by a group selected from an acyl group, a di(alkyl)aminosulfonyl group and a $C_{1-4}$ alkyl-carbamoyl group), a carbamoyl-$C_{1-4}$ alkyl group, an oxazolyl-$C_{1-4}$ alkyl group (the oxazolyl moiety of said group being optionally substituted by one to two $C_{1-4}$ alkyl group(s)), a thiazolyl-$C_{1-4}$ alkyl group, E is a group of the formula (i), Q¹ is a single bond, Q² is a single bond or a $C_{1-4}$ alkylene group, R⁴ is a saturated or unsaturated 5- to 6-membered heteromonocyclic group optionally substituted by one to three group(s) selected from an oxo group, a carbamoyl group and a $C_{1-4}$ alkyl-amino group or a group of the formula: —NH(R⁶), and R⁶ is (a) a $C_{1-4}$ alkyl group, (b) $C_{5-8}$ cycloalkyl group optionally substituted a carbamoyl group, (c) a phenyl group optionally substituted by one to two halogen atom(s), (d) a saturated or unsaturated 5- to 7-membered heteromonocyclic group optionally substituted by one to three group(s) selected from a halogen atom, an oxo group, $C_{1-4}$ alkyl group optionally substituted by one to three halogen atom(s), a phenyl group optionally substituted by one to two halogen atom(s), a cyanophenyl group, a $C_{1-4}$ alkyloxy-phenyl group, an acyl group, a phenyl-$C_{1-4}$ alkyl group, a carboxyl group, an amino group optionally substituted by one to two group(s) selected from a $C_{1-4}$ alkyl group and a cyano group, a carbamoyl group and a pyridyl group optionally substituted by one to two group(s) selected from a halogen atom, a $C_{1-4}$ alkyl group and a trihalogeno-$C_{1-4}$ alkyl group, or (e) an amino group optionally substituted by one to two group(s) selected from a $C_{1-4}$ alkyl group and a pyridyl group.

Among them, other examples of more preferred compound include:

(1) a compound [I] in which R¹ and R² are the same or different and a halogenophenyl group, R³ is a $C_{1-4}$ alkyl group, a trihalogeno-$C_{1-4}$ alky group or a $C_{1-4}$ alkyloxy-$C_{1-4}$ alkyl group, E is a group of the formula (ii), R is (a) a $C_{1-4}$ alkyl group optionally substituted by one to three halogen atom(s), (b) $C_{5-8}$ cycloalkyl group optionally substituted by a group selected from a hydroxyl group and a $C_{1-4}$ alkyl group, (c) a $C_{1-4}$ alkylthio group, (d) an aryl group optionally substituted by one to two group(s) selected from a halogen atom and a cyano group, or (e) a saturated or unsaturated heterocyclic group optionally substituted by a group selected from a $C_{1-4}$ alkylsulfonyl group, an acyl group and a heteroaryl group; or (2) a compound [I] in which $R^1$ and $R^2$ are the same or different and a halogenophenyl group, $R^3$ is a $C_{1-4}$ alkyl group or a $C_{1-4}$ alkyloxy-$C_{1-4}$ alkyl group, E is a group of the formula (iii) and $R^{41}$ is an amino group or a group of the formula:

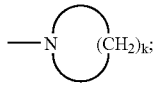

or (3) a compound [I] in which $R^1$ and $R^2$ are the same or different and a halogenophenyl group, $R^3$ is a $C_{1-4}$ alkyl group or a $C_{1-4}$ alkyloxy-$C_{1-4}$ alkyl group, E is a group of the formula (Iv) and $R^{42}$ is a 4- to 7-membered aliphatic heterocyclic group optionally substituted by a pyrimidinyl group or a trihalogeno-$C_{1-4}$ alkyl-pyrimidinyl group.

Among them, examples of further preferred compound include a compound [I] in which $R^1$ is a phenyl group substituted by a group selected from a chlorine atom and a trifluoro-$C_{1-3}$ alkyl group, $R^2$ is a phenyl group substituted by one to two group(s) selected from a chlorine atom or a fluorine atom, $R^3$ is a $C_{1-4}$ alkyl group optionally substituted by one to three group(s) selected from a fluorine atom, a cyano group, a $C_{1-4}$ alkyloxy group, an amino-$C_{1-3}$ alkyl group, a $C_{1-3}$ alkyl-carbonylamino group, a $C_{1-3}$ alkyl-carbamoylamino group, a $C_{1-3}$ alkyl-sulfonylamino group, a di($C_{1-3}$ alkyl)aminosulfonylamino group, a thiazolyl group and an oxazolyl group optionally substituted by one to two $C_{1-3}$ alkyl group(s), E is a group of the formula (i), $Q^1$ is a single bond, $Q^2$ is a single bond or a $C_{1-4}$ alkylene group, $R^4$ is a saturated or unsaturated 5- to 6-membered heteromonocyclic group optionally substituted by one to two group(s) selected from an oxo group, a $C_{1-3}$ alkylamino group and a carbamoyl group or a group of the formula: —NH($R^6$), $R^6$ is (a) a $C_{1-3}$ alkyl group, (b) a $C_{3-6}$ cycloalkyl group optionally substituted by a carbamoyl group, (c) a phenyl group optionally substituted by one to two group(s) selected from a chlorine atom, a fluorine atom, a cyano group and a $C_{1-3}$ alkyloxy group, (d) a saturated or unsaturated 5- to 7-membered heteromonocyclic group optionally substituted by one to three group(s) selected from a fluorine atom, an oxo group, a $C_{1-3}$ alkyl group optionally substituted by one to three fluorine atom(s), a trifluoro-$C_{1-3}$ alkyl-carbonyl group, a $C_{1-3}$ alkyloxy-$C_{1-3}$ alkyl-carbonyl group, a cyano-$C_{1-3}$ alkyl-carbonyl group, a carbamoyl group, an amino group optionally substituted by one to two group(s) selected from a $C_{1-3}$ alkyl group, a trifluoro-$C_{1-3}$ alkyl-carbonyl group and a benzoyl group, a benzoyl group optionally substituted by one to two group(s) selected from a chlorine atom, a fluorine atom, a cyano group, a $C_{1-3}$ alkyloxy group and a trifluoro-$C_{1-3}$ alkyl group, a carboxyl group, a benzyl group, a phenyl group optionally substituted by one to two group(s) selected from a chlorine atom and a fluorine atom and a pyridyl group optionally substituted by one to two group(s) selected from a chlorine atom, a fluorine atom, a cyano group, a $C_{1-3}$ alkyl group and a trifluoro-$C_{1-3}$ alkyl group, or (e) an amino group substituted by one to two group(s) selected from $C_{1-3}$ alkyl group and a pyridyl group.

Among them, other example of the further preferred compound [I] include:

(1) a compound [I] in which $R^1$ is a chlorophenyl group or a trifluoromethyl-phenyl group, $R^2$ is a chlorophenyl group, $R^3$ is a $C_{1-3}$ alkyl group, E is a group of the formula (ii) and R is a trifluoro-$C_{1-3}$ alkyl group; or (2) a compound [I] in which $R^1$ is a chlorophenyl group, $R^2$ is a chlorophenyl group, $R^3$ is a $C_{1-3}$ alkyl group, E is a group of the formula (iii) and $R^{41}$ is a 5- to 6-membered aliphatic heterocyclic group; or (3) a compound [I] in which $R^1$ is a chlorophenyl group, $R^2$ is a chlorophenyl group, $R^3$ is a $C_{1-3}$ alkyl group, E is a group of the formula (iv) and $R^{42}$ is a 5- to 6-membered aliphatic heterocyclic group optionally substituted by a trifluoro-$C_{1-3}$ alkyl-pyrimidinyl group.

Among the compounds [I] of the present invention, examples of particularly preferred compound include a compound selected from the group consisting of:

1-(2-chlorophenyl)-5-(4-chlorophenyl)-4-methoxy-3-[N-(1-azacycloheptyl)-carbamoyl]-1H-pyrazole;

1-(2-chlorophenyl)-5-(4-chlorophenyl)-4-methoxy-3-[N-(4-tetrahydropyranyl)-carbamoyl]-1H-pyrazole;

1-(2-chlorophenyl)-5-(4-chlorophenyl)-4-ethoxy-3-(N-morpholinocarbamoyl)-1H-pyrazole;

1-(2-chlorophenyl)-5-(4-chlorophenyl)-4-methoxy-3-[N-(2,2,2-trifluoroethyl)-carbamoyl]-1H-pyrazole;

1-(2-chlorophenyl)-5-(4-chlorophenyl)-4-methoxy-3-(N-piperidinocarbamoyl)-1H-pyrazole;

1-(2-chlorophenyl)-5-(4-chlorophenyl)-4-methoxy-3-(N-morpholino-carbamoyl)-1H-pyrazole;

1-(2-chlorophenyl)-5-(4-chlorophenyl)-4-methoxy-3-[N-(1-pyrrolidinyl)-carbamoyl]-1H-pyrazole;

1-(2-chlorophenyl)-5-(4-chlorophenyl)-4-ethoxy-3-(N-piperidinocarbamoyl)-1H-pyrazole;

1-(2-chlorophenyl)-5-(4-chlorophenyl)-4-(2-methoxyethoxy)-3-(N-piperidino-carbamoyl)-1H-pyrazole;

1-(2-chlorophenyl)-5-(4-chlorophenyl)-4-methoxy-3-(1-morpholinoacetyl)-1H-pyrazole;

1-(2,4-dichlorophenyl)-5-(4-chlorophenyl)-4-methoxy-3-(N-piperidino-carbamoyl-1H-pyrazole;

1-(2,4-dichlorophenyl)-5-(4-chlorophenyl)-4-methoxy-3-[N-(1-pyrrolidinyl-carbamoyl]-1H-pyrazole;

1-(2,4-dichlorophenyl)-5-(4-chlorophenyl)-4-methoxy-3-(N-morpholino-carbamoyl)-1H-pyrazole;

1-(2,4-dichlorophenyl)-5-(4-chlorophenyl)-4-methoxy-3-[(N',N'-dimethyl-hydrazino)carbonyl]-1H-pyrazole;

1-(2-chlorophenyl)-5-(4-chlorophenyl)-4-methoxy-3-(N-cyclopentyl-carbamoyl)-1H-pyrazole;

1-(2-chlorophenyl)-5-(4-chlorophenyl)-4-methoxy-3-(N-isopropylcarbamoyl)-1H-pyrazole;

1-(2,4-dichlorophenyl)-5-(4-chlorophenyl)-4-difluoromethoxy-3-[N-(1-pyrrolidinyl)carbamoyl]-1H-pyrazole;

1-(2-chloro-4-fluorophenyl)-5-(4-chlorophenyl)-4-methoxy-3-(N-morpholino-carbamoyl)-1H-pyrazole;

1-(2-chlorophenyl)-5-(4-trifluoromethylphenyl)-4-methoxy-3-[(N',N'-dimethylhydrazino)carbonyl]-1H-pyrazole;

1-(2-chlorophenyl)-5-(4-trifluoromethylphenyl)-4-methoxy-3-[N-(1-pyrrolidinyl)carbamoyl]-1H-pyrazole;

1-(2-chlorophenyl)-5-(4-trifluoromethylphenyl)-4-methoxy-3-(N-morpholino-carbamoyl)-1H-pyrazole;

1-(2-chlorophenyl)-5-(4-trifluoromethylphenyl)-4-methoxy-3-[N-(4-tetrahydropyranyl)carbamoyl]-1H-pyrazole;

1-(2-chlorophenyl)-5-(4-chlorophenyl)-4-methoxy-3-[N-[1-(4-fluorobenzoyl)-piperazin-4-yl]carbamoyl]-1H-pyrazole;

1-(2-chlorophenyl)-5-(4-trifluoromethylphenyl)-4-difluoromethoxy-3-[(N',N'-dimethylhydrazino)carbonyl]-1H-pyrazole;

1-(2-chlorophenyl)-5-(4-trifluoromethylphenyl)-4-difluoromethoxy-3-[N-(4-tetrahydropyranyl)carbamoyl]-1H-pyrazole;

1-(2-chlorophenyl)-5-(4-trifluoromethylphenyl)-4-difluoromethoxy-3-[N-(1-pyrrolidinyl)carbamoyl]-1H-pyrazole;

1-(2-chlorophenyl)-5-(4-chlorophenyl)-4-methoxy-3-[N-(1-pyrrolidinyl)-carbamoyl]-1H-pyrazole;

1-(2-chlorophenyl)-5-(4-chlorophenyl)-4-methoxy-3-[N-(cis-2,6-dimethyl-morpholino)carbamoyl]-1H-pyrazole;

1-(2-chlorophenyl)-5-(4-chlorophenyl)-4-methoxy-3-[N-(4,4-difluoro-piperidino)carbamoyl]-1H-pyrazole;

1-(2-chlorophenyl)-5-(4-chlorophenyl)-4-methoxy-3-[N-(4-trifluoromethyl-piperidino)carbamoyl]-1H-pyrazole;

1-(2-chlorophenyl)-5-(4-chlorophenyl)-4-methoxy-3-[(N',N'-dimethyl-hydrazino)carbonyl]-1H-pyrazole;

1-(2-chlorophenyl)-5-(4-chlorophenyl)-4-ethoxy-3-[N-(4-tetrahydropyranyl)-carbamoyl]-1H-pyrazole;

1-(2-chlorophenyl)-5-(4-trifluoromethylphenyl)-4-ethoxy-3-[(N',N'-dimethyl-hydrazino)carbonyl]-1H-pyrazole;

1-(2-chlorophenyl)-5-(4-chlorophenyl)-4-(2-methoxyethoxy)-3-[N-(4-tetrahydropyranyl)carbamoyl]-1H-pyrazole;

1-(2-chlorophenyl)-5-(4-trifluoromethylphenyl)-4-(2-methoxyethoxy)-3-[N-(1-pyrrolidinyl)carbamoyl]-1H-pyrazole;

1-(2-chlorophenyl)-5-(4-trifluoromethylphenyl)-4-(2-methoxyethoxy)-3-(N-morpholinocarbamoyl)-1H-pyrazole;

1-(2-chlorophenyl)-5-(4-chlorophenyl)-4-methoxy-3-[N-(1,1-dioxo-thiomorpholin-4-yl)carbamoyl]-1H-pyrazole;

1-(2-chlorophenyl)-5-(4-chlorophenyl)-4-methoxy-3-[N-(tetrahydrofuran-3-yl)-carbamoyl]-1H-pyrazole;

1-(2-chlorophenyl)-5-(4-chlorophenyl)-4-methoxy-3-[N-(4-benzoylpiperazin-1-yl)carbamoyl]-1H-pyrazole;

1-(2-chlorophenyl)-5-(4-chlorophenyl)-4-(n-propoxy)-3-[(N',N'-dimethyl-hydrazino)carbonyl]-1H-pyrazole;

1-(2-chlorophenyl)-5-(4-chlorophenyl)-4-methoxy-3-[N-[4-(4-chlorobenzoyl)-piperazin-1-yl]carbamoyl]-1H-pyrazole;

1-(2-chlorophenyl)-5-(4-chlorophenyl)-4-methoxy-3-[N-[4-(4-trifluoromethyl-benzoyl)piperazin-1-yl]carbamoyl]-1H-pyrazole;

1-(2-chlorophenyl)-5-(4-chlorophenyl)-4-methoxy-3-[N-[4-(3-fluorobenzoyl)-piperazin-1-yl]carbamoyl]-1H-pyrazole;

1-(2-chlorophenyl)-5-(4-chlorophenyl)-4-methoxy-3-[(1,1-dioxo-thiomorpholin-4-yl)acetyl]-1H-pyrazole;

1-(2-chlorophenyl)-5-(4-chlorophenyl)-4-difluoromethoxy-3-[N-(1-pyrrolidinyl)carbamoyl]-1H-pyrazole;

1-(2-chlorophenyl)-5-(4-chlorophenyl)-4-difluoromethoxy-3-[(N',N'-dimethyl-hydrazino)carbonyl]-1H-pyrazole;

1-(2-chlorophenyl)-5-(4-chlorophenyl)-4-difluoromethoxy-3-[N-(4-tetrahydropyranyl)carbamoyl]-1H-pyrazole;

1-(2-chlorophenyl)-5-(4-chlorophenyl)-4-ethoxy-3-[N-[4-(4-fluorobenzoyl)-piperazin-1-yl]carbamoyl]-1H-pyrazole;

1-(2-chlorophenyl)-5-(4-trifluoromethylphenyl)-4-ethoxy-3-[N-[4-(4-fluoro-benzoyl)-piperazin-1-yl]carbamoyl]-1H-pyrazole;

1-(2-chlorophenyl)-5-(4-chlorophenyl)-4-difluoromethoxy-3-[N-(1,1-dioxo-thiomorpholin-4-yl)carbamoyl]-1H-pyrazole;

1-(2-chlorophenyl)-5-(4-chlorophenyl)-4-methoxy-3-[N-[4-(3-chlorobenzoyl)-piperazin-1-yl]carbamoyl]-1H-pyrazole;

1-(2-chlorophenyl)-5-(4-chlorophenyl)-4-methoxy-3-[N-[4-(2-chlorobenzoyl)-piperazin-1-yl]carbamoyl]-1H-pyrazole;

1-(2-chlorophenyl)-5-(4-chlorophenyl)-4-methoxy-3-[N-[4-(3,4-difluoro-benzoyl)piperazin-1-yl]carbamoyl]-1H-pyrazole;

1-(2-chlorophenyl)-5-(4-chlorophenyl)-4-methoxy-3-[N-[4-(2,4-difluoro-benzoyl)piperazin-1-yl]carbamoyl]-1H-pyrazole;

1-(2-chlorophenyl)-5-(4-chlorophenyl)-4-methoxy-3-[N-[4-(3,5-difluoro-benzoyl)piperazin-1-yl]carbamoyl]-1H-pyrazole;

1-(2-chlorophenyl)-5-(4-chlorophenyl)-4-methoxy-3-[2-(1-methylsulfonyl-piperidin-4-yl)-1,3,4-oxadiazol-5-yl]-1H-pyrazole;

1-(2,4-dichlorophenyl)-5-(4-chlorophenyl)-4-methoxy-3-[N-(4-fluorophenyl)-carbamoyl]-1H-pyrazole;

1-(2-chlorophenyl)-5-(4-chlorophenyl)-4-methoxy-3-[N-[4-(4-fluorophenyl)-piperazin-1-yl]carbamoyl]-1H-pyrazole;

1-(2-chlorophenyl)-5-(4-chlorophenyl)-4-methoxy-3-[N-(3-trifluoromethyl-pyrrolidin-1-yl)carbamoyl]-1H-pyrazole;

1-(2,4-dichlorophenyl)-5-(4-trifluoromethylphenyl)-4-methoxy-3-[N',N'-dimethylhydrazino)carbonyl]-1H-pyrazole;

1-(2,4-dichlorophenyl)-5-(4-trifluoromethylphenyl)-4-methoxy-3-[N-(morpholino)carbamoyl]-1H-pyrazole;

1-(2,4-dichlorophenyl)-5-(4-trifluoromethylphenyl)-4-methoxy-3-[N-(1,1-dioxo-2-tetrahydrothienyl)carbamoyl]-1H-pyrazole;

1-(2-chloro-4-fluorophenyl)-5-(4-trifluoromethylphenyl)-4-methoxy-3-[N-(4-tetrahydropyranyl)carbamoyl]-1H-pyrazole;

1-(2-chloro-4-fluorophenyl)-5-(4-trifluoromethylphenyl)-4-methoxy-3-[N-(morpholino)carbamoyl]-1H-pyrazole;

1-(2-chlorophenyl)-5-(4-trifluormethylphenyl)-4-methoxy-3-[N-(1,1-dioxothio-morpholino)carbamoyl]-1H-pyrazole;

1-(2-chlorophenyl)-5-(4-chlorophenyl)-4-methoxy-3-[N-(4-fluoropiperidino)-carbamoyl]-1H-pyrazole;

1-(2,4-dichlorophenyl)-5-(4-chlorophenyl)-4-methoxy-3-[N-(4-benzoyl-piperazin-1-yl)carbamoyl]-1H-pyrazole;

1-(2,4-dichlorophenyl)-5-(4-chlorophenyl)-4-methoxy-3-[N-[4-(2,4-difluoro-benzoyl)piperazin-1-yl]carbamoyl]-1H-pyrazole;

5-(4-chlorophenyl)-1-(2-fluorophenyl)-4-methoxy-3-[N-(4,4-difluoro-piperidino)carbamoyl]-1H-pyrazole;

1-(2-chlorophenyl)-5-(4-trifluoromethylphenyl)-4-methoxy-3-[N-(4,4-difluoro-piperidino)carbamoyl]-1H-pyrazole;

1-(2,4-dichlorophenyl)-5-(4-trifluoromethylphenyl)-4-methoxy-3-[N-(4,4-difluoropiperidino)carbamoyl]-1H-pyrazole;

5-(4-chlorophenyl)-1-(2-fluorophenyl)-4-methoxy-3-[N-[3-(trifluoromethyl)-pyrrolidin-1-yl]carbamoyl]-1H-pyrazole;

1-(2-chlorophenyl)-5-(4-chlorophenyl)-4-methoxy-3-[N-[4-(5-cyanopyridin-2-yl)piperazin-1-yl]carbamoyl]-1H-pyrazole;

1-(2-chlorophenyl)-5-(4-chlorophenyl)-4-methoxy-3-[N-[4-[5-(difluoromethyl) pyridin-2-yl]piperazin-1-yl]carbamoyl]-1H-pyrazole;

1-(2-chlorophenyl)-5-(4-chlorophenyl)-4-difluoromethoxy-3-[N-(4,4-difluoro-piperidino)carbamoyl]-1H-pyrazole;

1-(2-chlorophenyl)-5-(4-trifluoromethylphenyl)-4-methoxy-3-[5-(2,2,2-trifluoroethyl)-1,3,4-oxadiazol-2-yl]-1H-pyrazole;

5-(4-chlorophenyl)-1-(2-fluorophenyl)-4-methoxy-3-[N-[4-(4-chlorophenyl)-piperazin-1-yl]carbamoyl]-1H-pyrazole;

5-(4-chlorophenyl)-1-(2-fluorophenyl)-4-methoxy-3-[N-[4-(4-fluorophenyl)-piperazin-1-yl]carbamoyl]-1H-pyrazole;

4-carbamoylmethoxy-1-(2-chlorophenyl)-5-(4-chlorophenyl)-3-[N-(4-carbamoyl-4-phenylpiperidino)carbamoyl]-1H-pyrazole;

4-(2-aminoethoxy)methoxy-1-(2-chlorophenyl)-5-(4-chlorophenyl)-3-[N-(pyrrolidin-1-yl)carbamoyl]-1H-pyrazole;

4-[2-(acetylamino)ethoxy]-1-(2-chlorophenyl)-5-(4-chlorophenyl)-3-[N-(pyrrolidin-1-yl)carbamoyl]-1H-pyrazole;

1-(2-chlorophenyl)-5-(4-chlorophenyl)-4-[2-(methylsulfonylamino)ethoxy]-3-[N-(pyrrolidin-1-yl)carbamoyl]-1H-pyrazole; and 1-(2-chlorophenyl)-5-(4-chlorophenyl)-4-[2-[(N,N-dimethylaminosulfonyl)-amino]ethoxy]-3-[N-(pyrrolidin-1-yl)carbamoyl]-1H-pyrazole;

or a pharmaceutically acceptable salt thereof.

When the compound [I] of the present invention has an asymmetric carbon atom(s) in its molecule, it may exist in the form of a stereoisomer thereof (diastereoisomers, optical isomers) owing to said asymmetric carbon atom(s) thereof, and the present invention also includes one of the stereoisomers and a mixture thereof.

A compound [I] of the present invention shows a potent antagonistic activity against CB1 receptor and may be useful as an agent for prevention and/or treatment of a CB1 receptor-mediated diseases such as psychosis including schizophrenia, anxiety disorders, stress, depression, epilepsy, neurodegenerative disorders, spinocerebellar disorders, cognitive disorders, craniocerebral trauma, panic attack, peripheral neuropathy, glaucoma, migraine, Parkinson's disease, Alzheimer's disease, Huntington's disease, Raynaud's syndrome, tremor, obsessive-compulsive disorders, amnesia, geriatric dementia, thymic disorders, Tourette's syndrome, tardive dyskinesia, bipolar disorders, cancer, drug-induced dyskinesia, dystonia, septic shock, hemorrhagic shock, hypotension, insomnia, immunological diseases including inflammations, multiple screlosis, emesis, diarrhea, asthma, appetite disorders such as bulimarexia, anorexia and the like, obesity, non insulin-dependent diabetes mellitus (NIDDM), memory disorders, urinary disorders, cardiovascular disorders, infertility disorders, infections, demyelination-related diseases, neuroinflammation, viral encephalitis, cerebral vascular incidents, cirrhosis of the liver or gastrointestinal disorders including intestinal transit disorders.

In addition, a compound [I] of the present invention may be useful as an agent for withdrawal from a chronic treatment, alcohol dependence or drug abuse (e.g., an opioid, barbiturate, marijuana, cocaine, anphethamine, phencyclidine, a hallucinogenic agent, a benzodiazepine compound and the like).

Furthermore, a compound [I] of the present invention may be useful as an agent for enhancing analgesic activity of analgesic or narcotic drugs and the like; or an agent for smoking cessation (withdrawal from smoking or nicotine dependence).

Moreover, a compound [I] of the present invention can be useful for treatment of a condition relating to metabolic diseases including obesity, diabetes, impaired glucose tolerance, hyperinsulinemia, hyperlipidemia, hypercholesterolemia, hyper-triglyceridemia, lipid metabolism disorder, atherosclerosis, hypertension, cardiovascular disease, coronary heart disease, depression, anxiety, drug addiction, and substance addiction.

The compound [I] of the present invention can be clinically used either in the free form or in the form of a pharmaceutically acceptable salt thereof. The pharmaceutically acceptable salt of the compound [I] includes a salt with an inorganic acid such as hydrochloride, sulfate, phosphate or hydrobromide, or a salt with an organic acid such as acetate, fumarate, oxalate, citrate, methanesulfonate, benzenesulfonate, tosylate or maleate. Besides, when the compound [I] of the present invention has a carboxyl group(s) and the like in its molecule, examples of the pharmaceutically acceptable salt include, salts with a base such as alkaline metal (e.g., sodium salt, potassium salt) or alkaline earth metal (e.g., calcium salt).

The compound [I] or a pharmaceutically acceptable salt thereof includes either intramolecular salt or an additive thereof, and solvates or hydrates thereof.

The present compound [I] or a pharmaceutically acceptable salt thereof can be either orally or parenterally, and can be formulated into a conventional pharmaceutical preparation such as tablets, granules, capsules, powders, injections or inhalants.

The dose of the compound [I] of the present invention or a pharmaceutically acceptable salt thereof may vary in accordance with the administration routes, and the ages, weights and conditions of the patients. For example, when administered in an injection preparation, it is usually in the range of about 0.0001 to 1.0 mg/kg/day, preferably in the range of about 0.001 to 0.1 mg/kg/day. When administered in an oral preparation, it is usually in the range of about 0.001 to 100 mg/kg/day, preferably in the range of 0.01 to 10 mg/kg/day.

A compound [I] of the present invention may also be useful as adjunctive, add-on or supplementary therapy for the treatment of the above-mentioned diseases/disorders. Said adjunctive, add-on or supplementary therapy means the concomitant or sequential administration of a compound of the present invention to a patient who has already received administration of, who is receiving administration of, or who will receive administration of one or more additional therapeutic agents for the treatment of the indicated conditions, for example, one or more known anti-depressant, anti-psychotics or anxiolytic agents.

The compound [I] of the present invention can be prepared by the following methods but should not be construed to be limited thereto.

(Method A)

Among the compound [I] of the present invention, a compound in which E is a group of the formula (i), $Q^2$ is a single bond or an oxygen atom, namely having the following formula [I-A]:

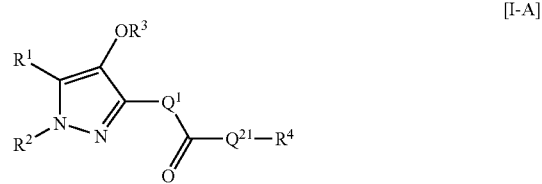

[I-A]

wherein $Q^{21}$ is a single bond or an oxygen atom and the other symbols are the same as defined above can be prepared by (1) reacting a compound of the formula [II-A]:

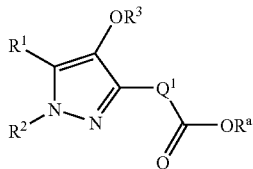

[II-A]

wherein $R^a$ is a hydrogen atom, an alkyl group or a benzyl group and the other symbols are the same as defined above with an alcohol compound of the following formula [III-a]:

[III-a]

wherein $R^{41}$ is a cycloalkyl group or an optionally substituted saturated or unsaturated heterocyclic group or (2) reacting the compound [II-A] with an amine or hydrazine compound of the following formula [III-b]:

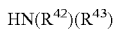

[III-b]

wherein one of $R^{42}$ and $R^{43}$ is a hydrogen atom or an alkyl group and the other is (a) an alkyl group optionally substituted by a group selected from a halogen atom, an amino group, an alkylthio group, an alkylsulfinyl group, an alkylsulfonyl group and an optionally substituted aryl group, (b) a cycloalkyl group, (c) a group of the formula: —N($R^8$)($R^9$), (d) an optionally substituted aryl group or (e) an optionally substituted saturated or unsaturated heterocyclic group, or both of $R^{42}$ and $R^{43}$ combine each other at their termini together with an adjacent nitrogen atom to form an optionally substituted saturated or unsaturated nitrogen-containing heterocyclic group, and the other symbols are the same as defined above or a salt thereof.

When $R^a$ is a hydrogen atom, the above-mentioned reaction (1) and (2) can be carried out in a solvent in the presence of a condensing agent, and in the presence or absence of an activating agent and a base. Examples of the solvent include any solvent which does not disturb the reaction, such as methylene chloride, chloroform, dimethylformaide, dimethylacetamide, tetrahydrofuran, dioxane, toluene, benzene, 1,2-dichloroethane, 1-methyl-pyrrolidinone, 1,2-dimethoxyethane and the like. The condensing agent may be, for example, dicyclohexylcarbodiimide (DCC), 1-ethyl-3-(3-dimethylaminopropyl)carbodiimide hydrochloride (WSC HCl), diphenylphosphoryl azide (DPPA), carbonyldiimidazole (CDI), diethylcyanophosphonate (DEPC), diisopropylcarbodiimide (DIPCI), benzotriazol-1-yloxytrispyrrolidinophosphonium hexafluorophosphate (PyBOP), carbonylditriazole, N-cyclohexylcarbodiimide-N'-propyloxymethyl-polystyrene (PS-carbodiimide), N-ethoxycarbonyl-2-ethoxy-1,2-dihydroquinoline (EEDQ), 2-(7-azabenzotriazol-1-yl)-1,1,3,3-tetramethyluronium hexafluorophosphate (HATU), 2-(1H-benzotriazol-1-yl-1,1,3,3-tetramethyluronium hexafluorophosphate (HBTU), bromotrispyrrolidinophosphonium hexafluorophosphate (PyBroP), 2-(1H-benzotriazol-1-yl)-1,1,3,3-tetramethyluronium tetrafluoroborate (TBTU), chloro-1,1,3,3-tetramethyl-uronium hexachloroantimonate (ACTU) and the like. Examples of the activating agent include 1-hydroxybenzotriazole (HOBt), 1-hydroxysuccinimide (HOSu), dimethylaminopyridine (DMAP), 1-hydroxy-7-azabenzotriazole (HOAt), hydroxy-phthalimide (HOPht), pentafluorophenol (Pfp-OH), 1-hydroxybenzotriazole-6-sulfonamidomethylpolystyrene (PS-HOBt) and the like. The base includes, for example, pyridine, triethylamine, diisopropylethylamine, 4-methylmorpholine, 1,8-diazabicyclo[5,4,0]-7-undecene (DBU) and the like.

In the above-mentioned process, the compound [II-A] can be used in an amount of 0.33 to 1.5 moles, preferably 0.5 to 1.2 moles per one mole of the compound [III-a] or compound [III-b]. The condensing agent can be used in an amount of 1.0 to 3.0 moles, preferably 1.0 to 1.2 moles per one mole of the compound [II-A], compound [III-a] or compound [III-b]. The base can be used in an amount of 1.0 to 3.0 moles, preferably 1.0 to 1.2 moles per one mole of the compound [II-A], compound [III-a] or compound [III-b]. The activating agent can be used in an amount of 0.01 to 2.0 moles, preferably 0.1 to 1.0 moles per one mole of the compound [II-A], [III-a] or [III-b]. The reaction can be carried out at 0 to 150° C., preferably 20 to 80° C.

When $R^a$ in the compound [II-A] is hydrogen atom, the compound [I-A] can be prepared by converting the compound [II-A] to a corresponding reactive derivative (e.g., an acid halide, a mixed acid anhydride) and reacting such reactive derivative with the compound [III-a] or compound [III-b] in the presence of the base in or without the solvent.

When $R^a$ in the compound [II-A] is an alkyl group or a benzyl group, the present process A can be also carried out by converting the compound [II-A] to a corresponding carboxylic acid compound of the following formula [II-Aa]:

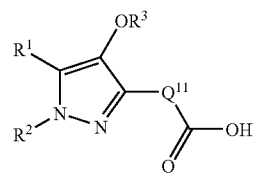

[II-Aa]

wherein the symbols are the same as defined above by a conventional manner such as hydrolysis, acidolysis with hydrochloric acid, formic acid, trifluoroacetic acid and the like or hydrogenation and then reacting the carboxylic acid compound [II-Aa] with the compound [III-a] or compound [III-b] in the same manner as described above.

(Method B)

Among the compounds [I] of the present invention, a compound in which E is a group of the formula (i), $Q^2$ is an alkylene group and $R^4$ is a group of the formula: —N($R^{42}$)($R^{43}$), namely a compound of the following formula [I-B]:

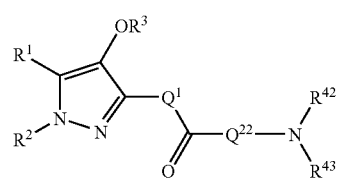

[I-B]

wherein $Q^{22}$ is an alkylene group and the other symbols are the same as defined above can be prepared by reacting a compound of the following formula [II-B]:

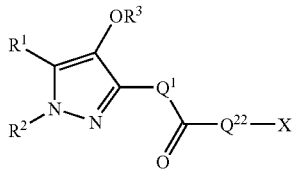

[II-B]

wherein X is a halogen atom and the other symbols are the same as defined above with the compound [III-b] or a salt thereof.

The reaction of the compound [II-B] with the compound [III-b] can be carried out in a solvent in the presence or absence of a base. Examples of the solvent include any solvent which does not disturb the reaction, such as methylene chloride, chloroform, dimethylformaide, dimethylacetamide, dimethylsulfoxide, tetrahydrofuran, dioxane, toluene, benzene, 1,2-dichloroethane, 1-methyl-pyrrolidinone, 1,2-dimethoxyethane and the like. The base includes, for example, pyridine, triethylamine, diisopropylethylamine, 4-methylmorpholine, 1,8-diazabicyclo[5,4,0]-7-undecene (DBU), potassium carbonate and the like.

In the above-mentioned process, the compound [III-b] can be used in an amount of 1.0 to 20 moles, preferably 1.0 to 3.0 moles per one mole of the compound [II-B]. The base can be used in an amount of 0 to 20 moles, preferably 1.0 to 3.0 moles per one mole of the compound [III-b] or [II-B]. The reaction can be carried out at −20 to 100° C., preferably 0 to 50° C.

(Method C)

(1) Among the compounds [I] of the present invention, a compound in which E is a group of the formula (i), $Q^1$ is a group of the formula: —N($R^7$)—, $Q^2$ is a single bond and $R^4$ is a group of the formula: —N($R^{42}$)($R^{43}$), namely, a compound of the following formula [I-C]:

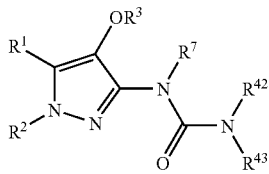

[I-C]

wherein the symbols are the same as defined above can be prepared by reacting a compound of the following formula [II-C]:

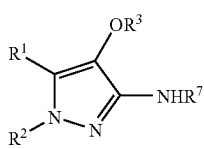

[II-C]

wherein the symbols are the same as defined above with the compound [III-b] in the presence of a compound of the formula [a]:

$$W^1\text{—CO—}W^2 \quad [a]$$

wherein $W^1$ and $W^2$ are the same or different and a removing group.

In the compound [a], examples of $W^1$ and $W^2$ include an imidazolyl group, a halogen atom or a phenoxy group. Concrete examples of such compound include 1,1'-carbonyldiimidazole, phosgene, triphosgene and the like. Examples of the solvent used in the reaction include any solvent which does not disturb the reaction, such as acetonitrile, dichloromethane, chloroform, 1,2-dichloroethane, tetrahydrofuran and the like. The compound [III-b] can be used in an amount of 1.0 to 5.0 moles, preferably 1.0 to 1.2 moles per one mole of the compound [II-C]. The compound [a] can be used in an amount of 1.0 to 5.0 moles, preferably 1.0 to 2.0 moles per one mole of the compound [II-C] or [III-b]. The reaction can be carried out at −20 to 100° C., preferably 0 to 50° C.

(2) Moreover, the compound [I-C] can be also prepared by reacting the compound [II-C] with the compound [a] to obtain a compound of the formula [IV]:

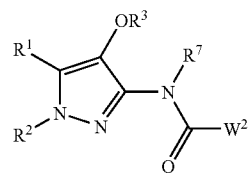

[IV]

wherein the symbols are the same as defined above and reacting the product or a reactive derivative thereof with the compound [III-b], or reacting the compound [III-b] with the compound [a] to obtain a compound of the formula [V]:

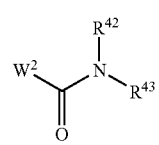

[V]

wherein the symbols are the same as defined above and reacting the product [V] or a reactive derivative thereof with the compound [II-C].

Examples of the reactive derivative of the compound [IV] or [V] include those in which $W^2$ is converted to a group of the formula:

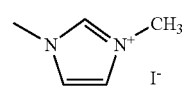

and such reactive derivative can be obtained by reacting a compound [V] in which $W^2$ is an imidazolyl group with methyl iodide.

The reaction of the compound [II-C] or the compound [II-b] with the compound [a] can be carried out in a solvent. Examples of the solvent include any solvent which does not disturb the reaction, such as acetonitrile, dichloromethane, 1,2-dichloroethane, benzene, toluene, tetrahydrofuran, 1,2-dimethoxyethane and the like. The compound [a] can be used in an amount of 1.0 to 3.0 moles, preferably 1.0 to 1.2 moles per one mole of the compound [II-C] or compound [III-b]. The present reaction can be conducted at 0 to 150° C., preferably at 20 to 80° C.

The reaction to convert the compound [IV] or [V] to its reactive derivative can be carried out by, for example, treating such compound [IV] or [V] with an alkyl halide such as methyl iodide in a solvent. The present reaction can be carried out at 0 to 150° C., preferably at 20 to 80° C.

The reaction of the compound [IV] (or its reactive derivative) with the compound [III-b] or the reaction of the compound [V] (or its reactive derivative) with the compound [II-C] can be conducted in a solvent in the presence of a base. Examples of the solvent include any solvent which does not disturb the reaction, such as methylene chloride, chloroform, dimethylformamide, dimethylacetamide, dimethyl-sulfoxide, tetrahydrofuran, dioxane, toluene, benzene, 1,2-dichloroethane, 1-methylpyrrolidinone, 1,2-dimethoxyethane and the like. Examples of the base include pyridine, triethylamine, diisopropylethylamine, 4-methylmorpholine, 1,8-diazabicyclo-[5,4,0]undecene and the like. Such reactive derivative can be used in an amount of 0.33 to 3.0 moles, preferably 0.5 to 1.2 moles per one mole of the compound [1'-b] or [II-C]. The present reaction can be conducted at −30 to 100° C., preferably at 0 to 50° C.

(3) Furthermore, among the compound [1-C], a compound in which $R^7$ is a hydrogen atom, namely a compound of the following formula [I-Ca]:

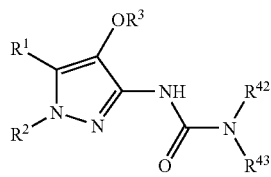

[I-Ca]

wherein the symbols are the same as defined above can be prepared by reacting an isocyanate compound of the following formula [XXIV]:

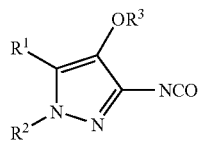

[XXIV]

wherein the symbols are the same as defined above with the compound [III-b] or a salt thereof.

The present reaction can be carried out in a solvent in the presence of a base and in the presence or absence of an activating agent. Examples of the solvent include any solvent which does not disturb the reaction, such as toluene, tetrahydrofuran, dioxane, chloroform, methylene chloride, 1,2-dimethoxyethane, acetonitrile and the like. Examples of the base include triethylamine, diisopropylethylamine, N-methyl-morpholine and the like. The activating agent may be 4-dimethylaminopyridine, 4-pyrrolidinopyridine and the like. The compound [II-b] or a salt thereof can be used in an amount of 1.0 to 5.0 moles, preferably 1.0 to 2.0 moles per one mole of the compound [XXIV]. The present reaction can be conducted at −50 to 50° C., preferably at −10 to 30° C.

(Method D)

Among the compound [I] of the present invention, a compound in which E is a group of the formula (i) and $Q^2$ is a single bond or an oxygen atom, namely, a compound of the following formula [I-D]:

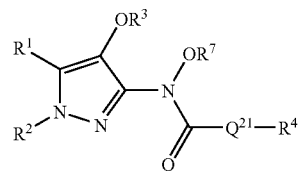

[I-D]

wherein the symbols are the same as defined above, can be prepared by reacting a compound [II-C] with a carboxylic acid compound [i]:

$$R^4\text{-}Q^{21}\text{-COOH}$$ [i]

wherein the symbols are the same as defined above or a reactive derivative thereof. The present reaction can be conducted in the same manner as described in Method A.

(Method E)

Method E-(i):

Among the compound [I] of the present invention, a compound in which E is a group of the formula (ii), namely, a compound of the following formula [I-E]:

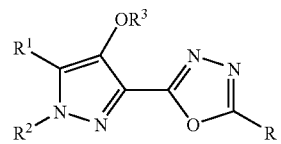

[I-E]

wherein the symbols are the same as defined above, can be prepared by treating a compound of the formula [I-Ea]:

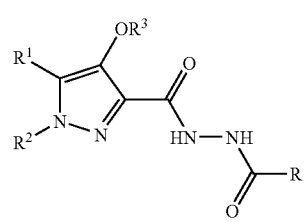

[I-Ea]

wherein the symbols are the same as defined above with a dehydrating agent in a solvent in the presence of a base. Examples of the solvent include any solvent which does not disturb the reaction, such as methylene chloride, chloroform, tetrahydrofuran, dichloroethene, toluene, acetonitrile and the like. Examples of the base include triethylamine, diisopropylethylamine, dimethylaminopyridine and the like. The dehydrating agent may be 2-chloro-1,3-dimethylimidazolinium chloride, phosphorus pentachloride, polyphospholic acid, phosphorus oxychloride, thionyl chloride and the like. The present reaction can be conducted at −10 to 80° C., preferably at 10 to 50° C.

Method E-(ii):

Among the compound [I] of the present invention, a compound in which $Q^1$ and $Q^2$ are a single bond and E is a group of the formula (iii) can be prepared, for example, in accordance with the following reaction scheme E-(ii).

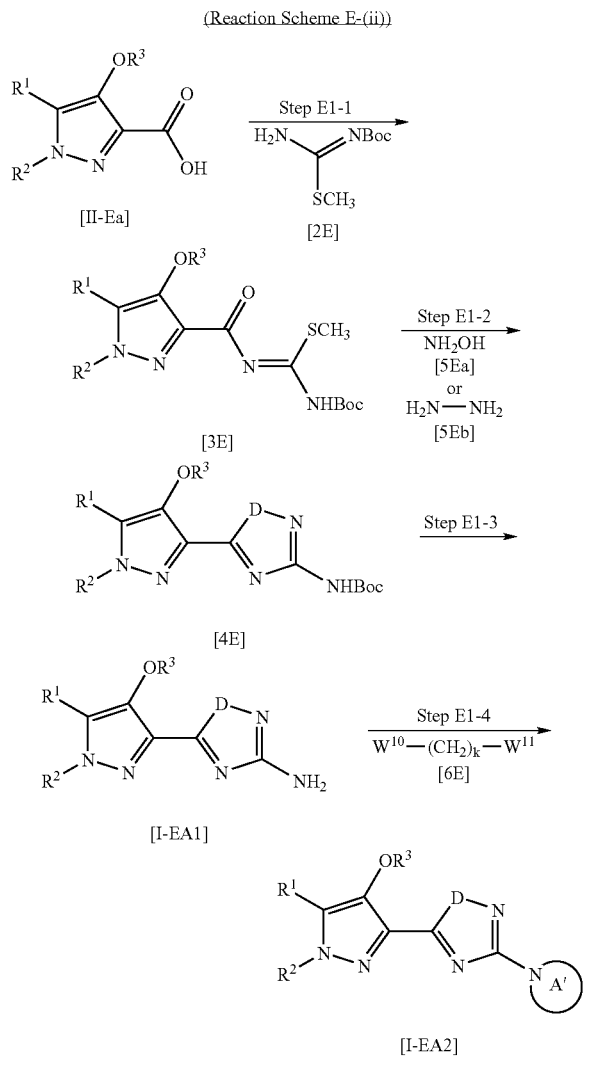

In the above reaction scheme, Boc is a tert-butoxycarbonyl group, $W^{10}$ and $W^{11}$ are a halogen atom, Ring A' is a 4- to 6-membered nitrogen-containing heterocyclic group, and the other symbols are the same as defined above.

Reaction Step E1-1:

The reaction of the compound [II-Ea] with the compound [2E] can be conducted in the same manner as described in Method A.

Reaction Step E1-2:

The reaction of the compound [3E] with the compound [5Ea] or a salt thereof can be carried out in a solvent in the presence of a base. Examples of the salt of the compound [5Ea] include hydrochloride and the like. Examples of the solvent include any solvent which does not disturb the reaction, such as methanol, ethanol, isopropanol, tetrahydrofuran, dioxane, N,N-dimethylformamide, dimethylsulfoxide, dichloromethane, chloroform, benzene, toluene and the like. Examples of the base include potassium carbonate, sodium hydrogencarbonate, sodium carbonate, sodium hydrogenphosphate, sodium methoxide, sodium ethoxide, potassium tert-butoxide, triethylamine, pyridine and the like. Besides, the reaction of the compound [3E] with the compound [5Eb] can be conducted in the same manner as described above.

Reaction Step E1-3:

The removal of a Boc group from the compound [4E] can be carried out in accordance with a conventional manner (e.g., treatment with an acid).

Reaction Step E1-4:

The reaction of the compound [I-EA1] with the compound [6E] can be carried out in a solvent in the presence of a base. Examples of the solvent include any solvent which does not disturb the reaction, such as acetonitrile, N,N-dimethylformamide, tetrahydrofuran, dichloromethane, chloroform, dichloroethane, dioxane, dimethoxyethane and the like. Examples of the base include potassium carbonate, sodium hydrogencarbonate, sodium carbonate, sodium hydrogenphosphate, triethylamine, pyridine and the like.

Method E-(iii):

Among the compound [I] of the present invention, a compound in which $Q^1$ and $Q^2$ are a single bond and E is a group of the formula (iv) can be prepared, for example, in accordance with the following reaction scheme E-(iii).

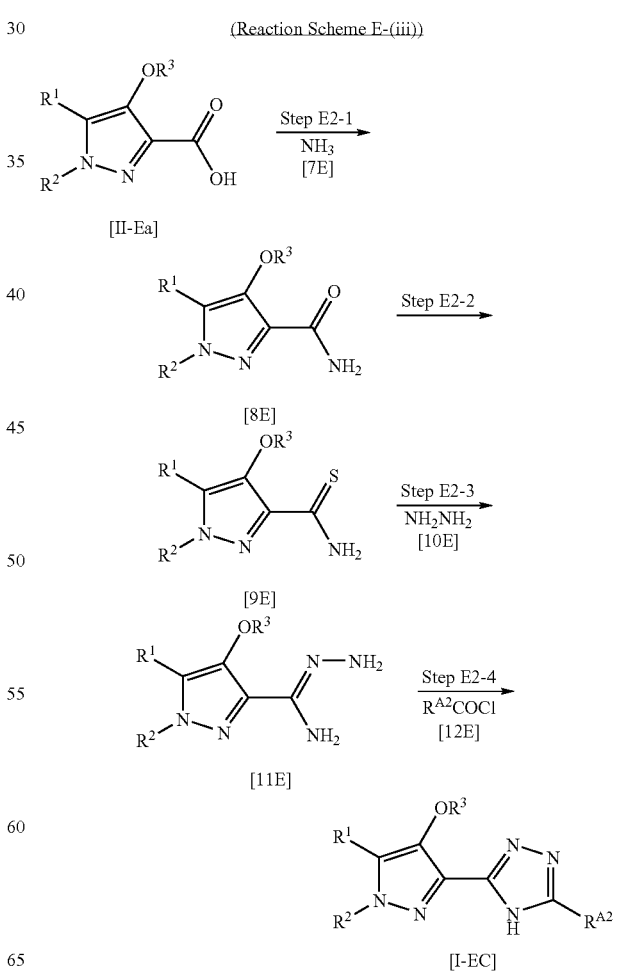

In the above reaction scheme, the symbols are the same as defined above.

Reaction Step E2-1:

The reaction of the compound [II-Ea] with the compound [7E] can be conducted in the same manner as described in Method A.

Reaction Step E2-2:

The conversion of the compound [8E] to the compound [9E] can be conducted in a solvent in the presence of a thionation reagent. Examples of the solvent include any solvent which does not disturb the reaction, such as toluene, benzene, xylene, tetrahydrofuran, dioxane, dichloromethane, chloroform and the like. Examples of the thionation reagent include Lawesson's reagent, diphosphorus pentasulfide and the like.

Reaction Step E2-3:

The reaction of the compound [9E] with the compound [10E] or a salt thereof can be carried out in a solvent in the presence of a base. The salt of the compound [10E] may be a hydrochloride and the like. Examples of the solvent include any solvent which does not disturb the reaction, such as ethanol, methanol, isopropanol, tetrahydrofuran, dioxane, dimethylformamide, dimethylsulfoxide, dichloromethane, chloroform, benzene, toluene and the like. Examples of the base include potassium carbonate, sodium hydrogencarbonate, sodium carbonate, sodium hydrogenphosphate, sodium methoxide, sodium ethoxide, potassium t-butoxide, triethylamine, pyridine and the like.

Reaction Step E2-4:

The reaction of the compound [11E] with the compound [12E] can be carried out in a solvent in the presence of a base. Examples of the solvent include any solvent which does not disturb the reaction, such as dichloromethane, dimethylformamide, tetrahydrofuran, dichloroethane, dioxane, dimethoxyethane and the like. Examples of the base include triethylamine, pyridine, potassium carbonate, sodium hydrogencarbonate, sodium carbonate, sodium hydrogenphosphate and the like.

(Method F)

Among the compound [I] of the present invention, a compound in which E is a group of the formula (i) and $Q^2$ is ethylene group, namely, a compound of the following formula [I-F]:

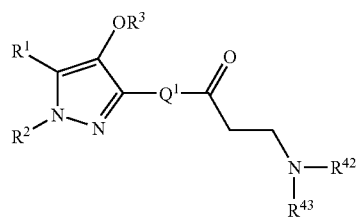

[I-F]

wherein the symbols are the same as defined above, can be prepared by, for example, reacting a compound of the following formula [II-F]:

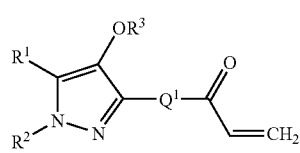

[II-F]

wherein the symbols are the same as defined above with a compound [III-b] or a salt thereof. The present reaction can be carried out in a solvent in the presence of a base. Examples of the solvent include any solvent which does not disturb the reaction, such as ethanol, isopropanol, tetrahydrofuran, dioxane, N,N-dimethylformamide, dimethylsulfoxide and the like. Examples of the base include triethylamine, diisopropylethylamine, N-methylmorpholine and the like. The compound [III-b] or a salt thereof can be used in an amount of 1.0 to 3.0 moles, preferably 1.1 to 1.5 moles per one mole of the compound [II-F]. The present reaction can be conducted at 20 to 200° C., preferably at 50 to 100° C.

(Method G)

Among the compound [I] of the present invention, a compound in which E is a group of the formula (i), $Q^2$ is a single bond and $R^4$ is a saturated 5- to 7-membered nitrogen-containing heteromonocyclic group substituted by an oxo group, namely, a compound of the following formula [I-G]:

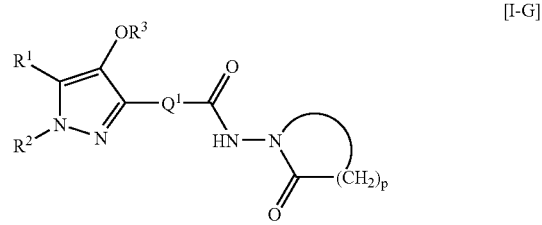

[I-G]

wherein p is an integer of 3 to 5 and the other symbols are the same as defined above, can be prepared by, for example, reacting a compound of the following formula [II-G]:

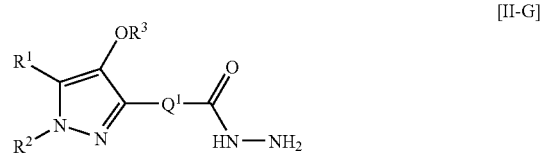

[II-G]

wherein the symbols are the same as defined above with a compound of the following formula [10]:

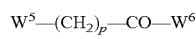

$$W^5—(CH_2)_p—CO—W^6$$ [10]

wherein $W^5$ and $W^6$ are a halogen atom and the other symbol is the same as defined above.

The present reaction can be carried out in a solvent in the presence of a base. Examples of the solvent include any solvent which does not disturb the reaction, such as methylene chloride, chloroform, acetonitrile, tetrahydrofuran, dioxane, N,N-dimethylformamide, ethanol and the like. Examples of the base include triethylamine, diisopropylethylamine, N-methylmorpholine and the like. The compound [10] can be used in an amount of 1.0 to 3.0 moles, preferably 1.1 to 2.0 moles per one mole of the compound [II-G]. The present reaction can be conducted at −10 to 120° C., preferably at 30 to 80° C.

(Method H)

Among the compound [I] of the present invention, a compound in which E is a group of the formula (i), $Q^2$ is a single bond and $R^4$ is a 1,1-dioxo-thiomorpholino group, namely, a compound of the following formula [1-H]:

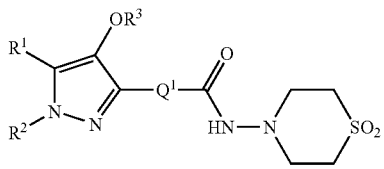

wherein the other symbols are the same as defined above, can be prepared by, for example, reacting a compound [II-G] mentioned above with divinylsulfone in a solvent in the presence of a base. Examples of the solvent include any solvent which does not disturb the reaction, such as ethanol, isopropanol, dioxane, toluene, N,N-dimethylformamide, dimethylsulfoxide and the like. Examples of the base include triethylamine, diisopropylethylamine, N-methylmorpholine, dimethylamino-pyridine and the like. The divinylsulfone can be used in an amount of 1.0 to 3.0 moles, preferably 1.2 to 1.5 moles per one mole of the compound [II-G]. The present reaction can be conducted at 60 to 200° C., preferably at 80 to 160° C.

(Method I)

Among the compound [I] of the present invention, a compound in which E is a group of the formula (i), $Q^2$ is a single bond and $R^4$ is an amino group substituted by a saturated 5- to 7-membered nitrogen-containing heteromonocyclic group substituted by an oxo group, namely, a compound of the following formula [I-I]:

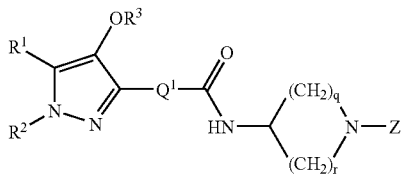

wherein Z is an acyl group, q is an integer of 2 to 3, r is an integer of 1 to 2 and the other symbols are the same as defined above, can be prepared by, for example, subjecting a compound of the following formula [I-Ia]:

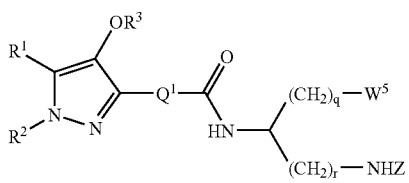

wherein the symbols are the same as defined above to intramolecular cyclization reaction. The present reaction can be conducted in a solvent in the presence of a base. Examples of the solvent include any solvent which does not disturb the reaction, such as methylene chloride, dimethylsulfoxide, dimethylimidazolidone, acetonitrile, tetrahydrofuran, 1,2-dimethoxyethane, 1,2-dichloroethene and the like. Examples of the base include sodium hydride, potassium hydride, potassium carbonate, cesium carbonate, sodium ethoxide and the like. The base can be used in an amount of 1.0 to 5.0 moles, preferably 1.1 to 1.5 moles per one mole of the compound [I-Ia]. The present reaction can be conducted at 40 to 200° C., preferably at 80 to 120° C.

(Method J)

Among the compound [I] of the present invention, a compound of the following formula [I-J]:

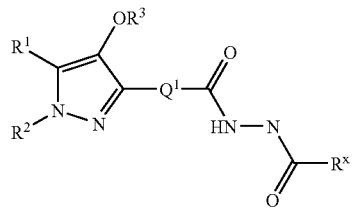

wherein the symbols are the same as defined above, can be prepared by, for example, reacting a compound [II-G] with a carboxylic acid compound of the following formula:

$$R^x\text{---COOH} \quad [Ac\text{-}1]$$

wherein the symbol is the same as defined above or a reactive derivative thereof (e.g., a corresponding acid halide, a corresponding acid anhydride). The present reaction can be conducted in the same manner as described in the above Method A.

(Method K)

Among the compound [I] of the present invention, a compound of the following formula [I-K]:

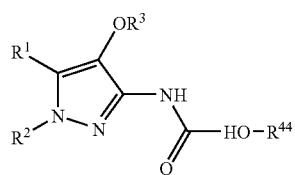

wherein $R^{44}$ is an optionally substituted saturated or unsaturated heteromonocyclic group and the other symbols are the same as defined above, can be prepared by, for example, reacting a compound [IV] ($R^7$=H) or a reactive derivative thereof with an alcohol compound of the following formula:

$$R^{44}\text{---OH} \quad [11]$$

wherein the symbol is the same as defined above. The present reaction can be conducted in the same manner as described in the above Method C (2). The objective compound [I] of the present invention can be also prepared by, for example, intramolecularly converting the substituent(s) in $R^1/R^2$ and the like of such a compound [I] as obtained above to the other desired substituent(s). The intramolecular conversion processes can be selected according to the kinds of the objective substituents, and may be carried out, for example, in the following methods (a) to (f).

Method (a): A compound [I] in which the substituent(s) in $R^1/R^2$ is a cyano group (or a group containing a cyano group) can be obtained by reacting a corresponding compound [I] in which $R^1/R^2$ is a halogen atom (or a halogen-containing group) with cyanide compound (e.g., zinc cyanide, copper cyanide, trimethylsilyl cyanide, potassium cyanide and the like) in the presence or absence of a catalyst, a base and an additive. Examples of the base include triethylamine, N-methylpiperidine, diisopropylethylamine and the like. Examples of said catalyst include a palladium catalyst such as palladium acetate, tris(dibenzylideneacetone)dipalladium, trans-dichlorobis-(tricyclohexylphosphine)palladium, tetrakis(triphenylphosphine)palladium and the like or a nickel catalyst such as dibromobis-(triphenylphosphine)nickel and the like. Examples of the additive include a phosphine compound such as 1,1'-bis-(diphenylphosphino)ferrocene, racemic 2,2'-bis(diphenylphosphino)-1,1'-binaphthyl, 2-di-tert-butylphosphino)biphenyl, 2-(dicyclohexylphosphino)biphenyl, 2-dicyclohexylphosphino-2-(N,N'-dimethyl-amino)biphenyl, tri-tert-butylphospine and the like. Examples of the additive include a phosphine compound such as triphenylphosiphine, 1,1'-bis(diphenylphosphino)ferrocene, racemic 2,2'-bis(diphenyl-phosphino)-1,1'-binaphthyl, 2-(di-tert-butylphosphino)biphenyl, 2-(dicyclohexyl-phosphino)biphenyl, 2-dicyclohexylphosphino-2'-(N,N'-dimethylamino)biphenyl or tri-tert-butylphosphine and the like.

Method (b): A compound [I] having an alkylamino group or a cycloalkyl-amino group (or a group containing an alkylamino group or a cycloalkylamino group) can be obtained by reacting a corresponding compound [I] having a halogen atom with a mono- or di-alkylamine or a cycloalkylamine in the presence of a catalyst, an additive and a base. Examples of the catalyst may be the palladium compounds and the copper compounds used in Method (a) and the like. Examples of the additive may be the phosphine compounds used in Method (a) and the like. Examples of the base include potassium acetate, potassium carbonate, cesium carbonate, potassium tert-butoxide and the like.

Method (c): A compound [I] having an alkyloxy group (or a group containing an alkyloxy group) can be obtained by reacting a corresponding compound [I] having a hydroxyl group (or a group containing hydroxyl group) with an alkyl halide in a solvent, or reacting a corresponding compound [I] having a hydroxyl group (or a group containing an alkyloxy group) with an alkanol in a solvent in the presence of a base (e.g., potassium carbonate, cesium carbonate, sodium hydride and the like) or an activating agent (e.g., diethyl azodicarboxylate and the like) and in the presence of a tri-substituted phosphine.

Method (d): A compound [I] having an alkylsulfinyl or alkylsulfonyl group (or a group containing an alkylsulfinyl or alkylsulfonyl group) can be obtained by treating a corresponding compound [I] having an alkylthio group (or a group containing an alkylthio group) with an oxidizing agent such as m-chloroperbenzoic acid in a solvent.

Method (e): A compound [I] having an acylamino group (or a group containing an acylamino group) can be obtained by reacting a corresponding compound [I] having an amino group (or a group containing an amino group) with an acylating agent such as a carboxylic acid compound [Ac-1] or a reactive derivative (e.g., a corresponding acid halide, a corresponding acid anhydride). The present reaction can be conducted in a solvent in the presence of a base (e.g., triethylamine) or a condensing agent (e.g., water-soluble carbodiimide) and in the presence or absence of an activating agent (e.g., 1-hydroxybenzotriazole).

Method (f): A compound [I] having a carbamoyl group (or a group containing carbamoyl group) can be obtained by treating a corresponding compound [I] having an alkyloxycarbonyl group (or a group containing an alkyloxycarbonyl group) with ammonia in a solvent.

If necessary, the compounds [I] of the present invention obtained in the aforementioned Processes can be converted to a pharmaceutically acceptable salt thereof by a conventional manner.

[Preparation of Intermediate compound]

i) Among the intermediate compounds of the present invention, compound [II-A] in which Q1 is a single bond or an alkylene group can be prepared in a manner as described in the following reaction scheme A1, A2 or A3

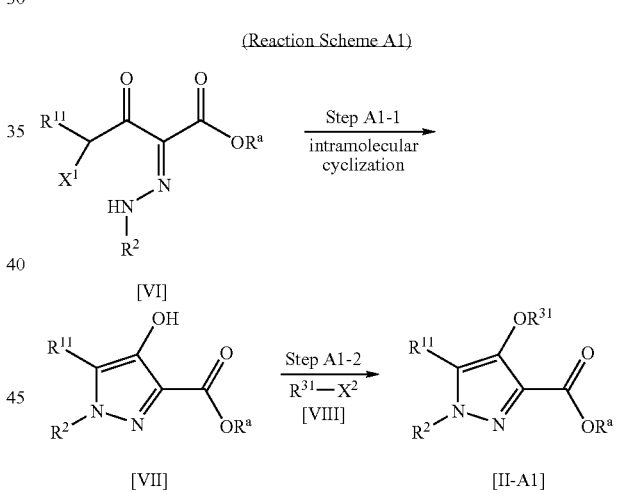

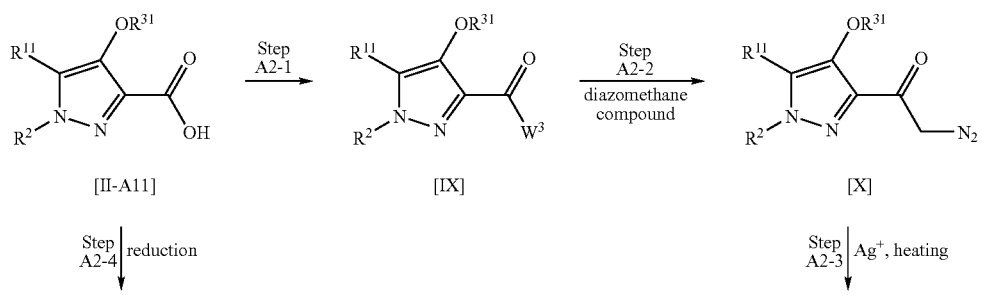

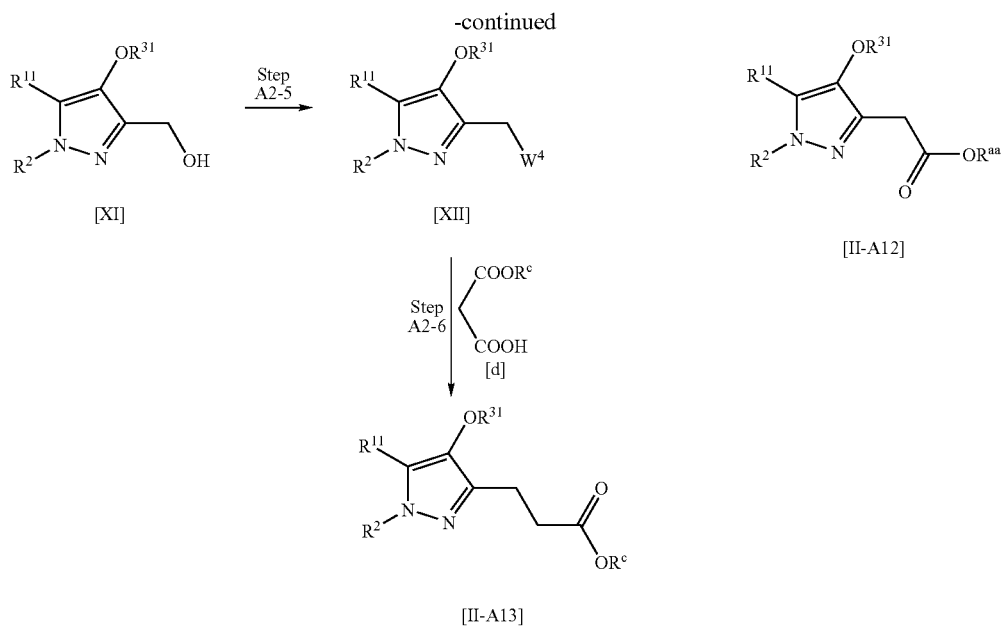

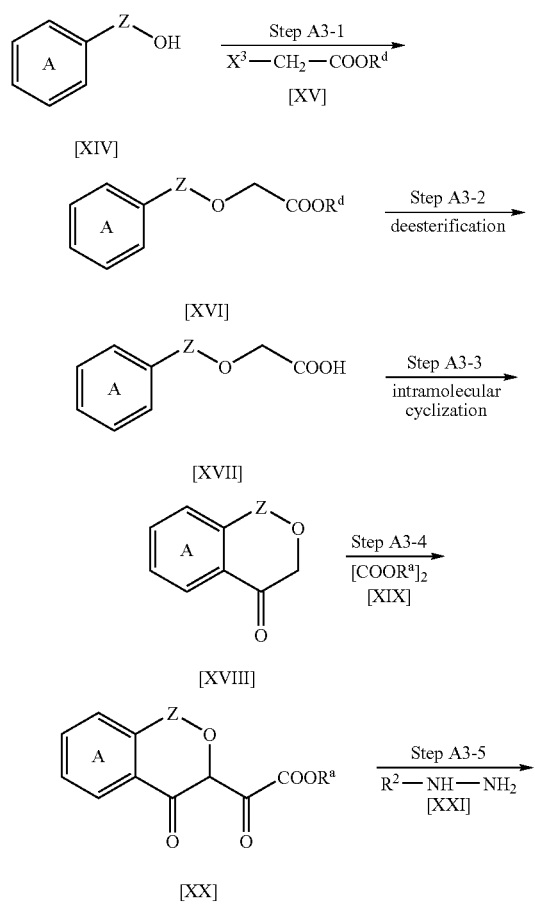

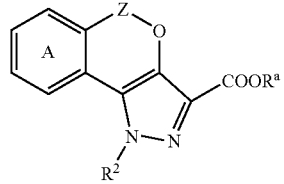

In the above-mentioned reaction scheme $A^1$, $A^2$ and $A^3$, $R^{11}$ is an optionally substituted aryl group or an optionally substituted heteroaryl group, $R^{31}$ is an alkyl group optionally substituted by a group selected from a halogen atom, an amino group, a monoalkylamino group and a dialkylamino group, $R^{11}$ is a hydrogen atom or an alkyl group, $R^c$ is an alkyl group, $R^d$ is an alkyl group or a benzyl group, $X^1$, $X^2$ and $X^3$ are a halogen atom, $W^3$ is a reactive residue, $W^4$ is a reactive residue, and the other symbols are the same as defined above.

Reaction Step A1-1:

The reaction to obtain the compound [VII] from the compound [VI] can be carried out in a solvent in the presence of a base. Examples of the base include sodium acetate, potassium acetate, sodium carbonate, potassium carbonate, sodium hydrogencarbonate, potassium hydrogencarbonate, sodium methoxide, sodium ethoxide and the like. Examples of the solvent include any solvent which does not disturb the reaction, such as water, ethanol, methanol, dioxane, dimethylformamide, dimethylacetamide and the like. The base can be used in an amount of 1.0 to 20 moles, preferably 1.0 to 3.0 moles per one mole of the compound [VI]. The reaction can be carried out at 30 to 200° C., preferably 60 to 100° C.

Reaction Step A 1-2:

The reaction of the compound [VII] with the compound [VIII] can be conducted in a solvent in the presence of a base. Examples of the base include sodium hydride, potassium hydride, sodium azide, lithium diisopropylamide, lithium hexamethyldisilazide, potassium carbonate, sodium methoxide, sodium ethoxide and the like. Examples of the solvent include any solvent which does not disturb the reaction, such as methylene chloride, benzene, toluene, tetrahydrofuran, dimethoxyethane, dioxane, dimethylformamide, dimethylsulfoxide and the like. The compound [VIII] can be used in an amount of 1.0 to 10 moles, preferably 1.0 to 3.0 moles per one mole of the compound [VII]. The base can be used in an amount of 1.0 to 20 moles, preferably 1.0 to 5.0 moles per one mole of the compound [VII]. The reaction can be carried out at −30 to 100° C., preferably 20 to 60° C.

Meanwhile, the compound [II-A1] can be also prepared by reacting the compound [VII] with an alcohol compound [VIII-a]:

$$R^{31}—OH \quad\quad [\text{VIII-a}]$$

wherein the symbol is the same as defined above in a solvent in the presence of an activating agent (e.g., diethyl azodicarboxylate and the like). Examples of the solvent include any solvent which does not disturb the reaction, such as methylene chloride, chloroform, dimethylformamide, dimethylacetamide, dimethylsulfoxide, tetrahydro-furan, dioxane, toluene, benzene, 1,2-dichloroethane, 1-methylpyrrolidinone, 1,2-dimethoxyethane and the like.

Reaction Step A2-1:

The conversion of the compound [II-A11] to a corresponding reactive derivative (compound [IX]) can be carried out in a conventional manner. Examples of such reactive derivative include a corresponding acid halide (a compound [IX] in which $W^3$ is a halogen atom) or a corresponding mixed acid anhydride (a compound [IX] in which $W^3$ is an alkyloxycarbonyloxy group and the like). The corresponding acid halide can be prepared by, for example, reacting the compound [II-A11] with a halogenating agent (e.g., thionyl chloride, phosphorus oxychloride, phosphorus pentachloride, oxalyl chloride and the like) in or without a solvent in the presence or absence of a catalytic amount of dimethylformamide. Besides, the corresponding mixed acid anhydride can be prepared by, for example, reacting the compound [II-A11] with an alky chloroformate (e.g., ethyl chloroformate and the like) in the presence of a base (e.g., triethylamine, diisopupylethylamine and the like). Examples of the solvent include any solvent which does not disturb the reaction, such as methylene chloride, chloroform, tetrahydrofuran, benzene, toluene and the like. The present reaction can be conducted at 40 to 100° C., preferably 40 to 80° C.

Reaction Step A2-2:

The conversion of the compound [IX] to the compound [α] can be carried out in a solvent in the presence of a diazomethane compound (e.g., diazomethane, trimethylsilyl diazomethane and the like). Examples of the solvent include any solvent which does not disturb the reaction, such as diethylether, dioxane, benzene, toluene and the like). The diazomethane compound can be used in an amount of 1.0 to 10 moles, preferably 1.0 to 3.0 moles per one mole of the compound [IX]. The reaction can be carried out at −50 to 80° C., preferably −10 to 50° C.

Reaction Step A2-3:

The conversion of the compound [α] to the compound [II-A12] can be carried out in a solvent in the presence or absence of a silver salt under heating. Examples of the solvent include any solvent which does not disturb the reaction, such as water, an alkanol (e.g., methanol, ethanol) and the like. Examples of the silver salt include silver oxide, silver benzoate and the like. The silver salt can be used in an amount of 1.0 to 20 moles, preferably 1.0 to 5.0 moles per one mole of the compound [X]. The reaction can be carried out at 50 to 200° C., preferably 80 to 150° C.

Reaction Step A2-4:

The reaction to obtain the compound [X] by reducing the compound [II-A11] can be carried out in a solvent in the presence of a reducing agent (e.g., lithium aluminum hydride and the like). Examples of the solvent include any solvent which does not disturb the reaction, such as diethylether, tetrahydrofuran and the like. The reducing agent can be used in an amount of 1.0 to 20 moles, preferably 2.0 to 5.0 moles per one mole of the compound [II-A11]. The reaction can be carried out at −50 to 100° C., preferably −10 to 40° C.

The compound [XI] can be also prepared by reducing a compound [II-A1] in which $R^a$ is an alkyl group. The present reaction can be conducted in a solvent in the presence of a reducing agent such as sodium borohydride and the like. Examples of the solvent include any solvent which does not disturb the reaction, such as a mixture of tetrahydrofuran and methanol and the like. The reducing agent can be used in an amount of 1.0 to 20 moles, preferably 2.0 to 5.0 moles per one mole of the compound [II-A1]. The reaction can be carried out at 30 to 100° C., preferably 50 to 80° C.

Reaction Step A2-5:

The conversion of the compound [XI] to a corresponding reactive derivative (compound [XII]) can be carried out in a conventional manner. For example, a compound [XII] in which $W^4$ is a halogen atom or an alkylsulfonyloxy group can be prepared by treating the compound [XI] with a thionyl halide such as thionyl chloride or an alkylsulfonylhalide such as methanesulfonylchloride, respectively.

Reaction Step A2-6:

The reaction of the compound [XII] with the compound [d] or a salt thereof can be carried out in a solvent in the presence of a base. Examples of the salt of the compound [d] include a metal salt such as potassium salt. Examples of the solvent include any solvent which does not disturb the reaction, such as diethylether, tetrahydrofuran, benzene, dimethylformamide, dimethylacetamide, methanol, ethanol and the like. Examples of the base include sodium hydride, potassium hydride, sodium methoxide, sodium ethoxide, lithium diisopropylamide, lithium hexamethyl-disilazide and the like. The compound [d] or a salt thereof can be used in an amount of 1.0 to 10.0 moles, preferably 1.5 to 3.0 moles per one mole of the compound [XII]. The base can be used in an amount of 1.0 to 10.0 moles, preferably 1.5 to 3.0 moles per one mole of the compound [XII]. The reaction can be carried out at −20 to 200° C., preferably 20 to 100° C.

A compound [II-A] in which $Q^1$ is a $C_{3-6}$ alkylene group can be obtained by, for example, if required, converting an objective compound obtained in the above Step A2-3 (or Step A2-6) to a corresponding carboxylic acid compound by deesterification and then subjecting such carboxylic acid compound to a serial reaction process of Step A2-1, A2-2 and A2-3 (or Step A2-4, A2-5 and A2-6), repeatedly in desired times.

A compound [II-A] in which $Q^1$ is a group of the formula: —$N(R^7)$— can be prepared by, for example, subjecting a compound [II-Ae] or compound [II-Af] (cf., the Reaction Step C1-4 bellow) to conventional deesterfication.

Reaction Step A3-1:

The reaction of the compound [XIV] with the compound [XV] can be carried out in a solvent in the presence of a base. Examples of the base include sodium carbonate, potassium carbonate, sodium hydrogencarbonate, potassium hydrogencarbonate, sodium hydride, potassium hydride, lithium diisopropylamide, lithium hexamethyldisilazide, cesium carbonate and the like. Examples of the solvent include any solvent which does not disturb the reaction, such as methylene chloride, chloroform, dimethylformamide, dimethylacetamide, dimethylsulfoxide, tetrahydrofuran, dioxane, toluene, benzene, 1,2-dichloroethane, 1-methylpyrrolidinone, 1,2-dimethoxyethane and the like. The compound [XV] or a salt thereof can be used in an amount of 1.0 to 5.0 moles, preferably 1.1 to 2.0 moles per one mole of the compound [XIV]. The base can be used in an amount of 1.0 to 5.0 moles, preferably 1.1 to 2.0 moles per one mole of the compound [XIV]. The reaction can be carried out at −10 to 100° C., preferably 20 to 80° C.

Reaction Step A3-2:

Deesterification of the compound [XVI] can be carried out by subjecting such compound to a conventional hydrolysis.

Reaction Step A3-3:

Intramolecular cyclization of the compound [XVII] can be carried out in a solvent in the presence of a halogenating agent and in the presence or absence of an activating agent. Examples of the halogenating agent include thionyl chloride, phosphorus oxychloride, phosphorus pentachloride, oxalyl chloride and the like. Examples of the activating agent include aluminum chloride, iron(III) chloride, borane trichloride, borane trifluoride, titanium tetrachloride, tin tetrachloride and the like. Examples of the solvent include any solvent which does not disturb the reaction, such as carbon disulfide, dichloromethane, nitromethane, chloroform, tetrahydrofuran, dioxane, toluene, benzene, nitrobenzene, 1,2-dichloroethane, 1,2-dimethoxyethane and the like. The halogenating agent can be used in an amount of 1.0 to 5.0 moles, preferably 1.1 to 2.0 moles per one mole of the compound [XVII]. The reaction can be carried out at 30 to 200° C., preferably 80 to 150° C.

Reaction Step A34:

The reaction of the compound [XVIII] with the compound [XIX] can be carried out in a solvent in the presence of a base. Examples of the base include an alkali metal alkoxide such as sodium methoxide, alkali metal amide such as lithium diisopropylamide, an alkali metal hydride such as sodium hydride and the like. Examples of the solvent include any solvent which does not disturb the reaction, such as ethanol, methanol, tetrahydrofuran, dioxane, toluene, benzene, 1,2-dimethoxyethane and the like. The compound [XIX] can be used in an amount of 1.0 to 3.0 moles, preferably 1.0 to 1.5 moles per one mole of the compound [XVIII]. The base can be used in an amount of 1.0 to 5.0 moles, preferably 1.1 to 3.0 moles per one mole of the compound [XVIII]. The reaction can be carried out at −70 to 150° C., preferably −50 to 50° C.

Reaction Step A3-5:

The reaction of the compound [XX] with the compound [XXI] can be carried out in a solvent in the presence or absence of a base. Examples of the base include pyridine, triethylamine, diisopropylethylamine, 4-methylmorpholine, 1,8-diazabicyclo-[5,4,0]undecene and the like. Examples of the solvent include any solvent which does not disturb the reaction, such as ethanol, methanol, tetrahydrofuran, dioxane, toluene, benzene, 1,2-dimethoxyethane and the like. The compound [XXI] can be used in an amount of 1.0 to 3.0 moles, preferably 1.1 to 1.5 moles per one mole of the compound [XX]. The reaction can be carried out at −10 to 100° C., preferably 20 to 60° C.

ii) The compound [II-B] can be prepared by, for example, using a compound [II-Aa] or a corresponding dialkylamide compound or a corresponding N-alkyl-N-alkyloxyamide compound in accordance with the reaction scheme B mentioned bellow.

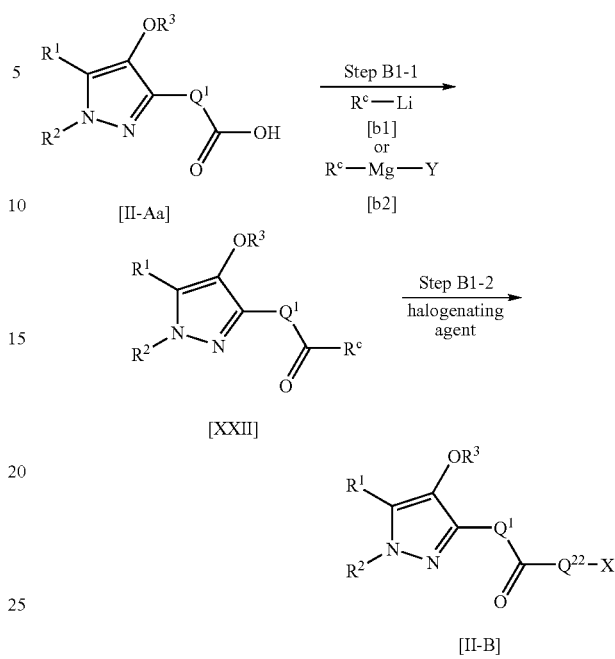

In the above reaction scheme, $R^cC$ is an alkyl group, Y is a halogen atom and the other symbols are the same as defined above.

Reaction Step B1-1:

The reaction of the compound [II-Aa] with the compound [b1] or compound [b2] can be carried out in a solvent. Examples of the solvent include any solvent which does not disturb the reaction, such as diethylether, tetrahydrofuran, dioxane, dimethoxyethane, benzene, toluene and the like. The compound [b1] or compound [b2] can be used in an amount of 2.0 to 3.0 moles, preferably 2.0 to 2.5 moles per one mole of the compound [II-Aa]. The reaction can be carried out at −50 to 80° C., preferably −10 to 40° C.

Reaction Step B1-2:

The halogenation of the compound [XXII] can be carried out in a solvent. Examples of the halogenating agent include bromine, N-bromosuccinimide, bis(dimethylacetamide)dibromobromate and the like. Examples of the solvent include any solvent which does not disturb the reaction, such as diethylether, dichloromethane, 1,2-dichloroethane, chloroform, carbon tetrachloride and the like. The halogenating agent can be used in an amount of 1.0 to 3.0 moles, preferably 1.0 to 2.0 moles per one mole of the compound [XXII]. The reaction can be carried out at −10 to 50° C., preferably 0 to 30° C.

iii) The compound [II-C] can be prepared, for example, in a manner as described in the following reaction scheme C1.

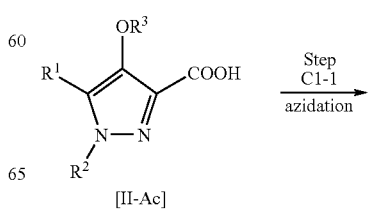

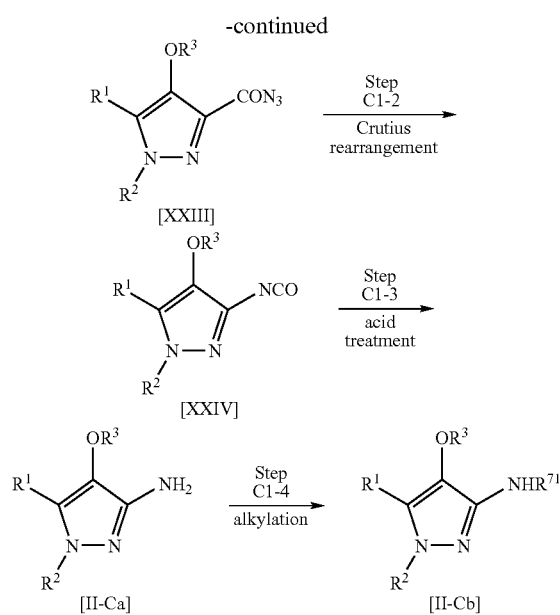

In the above Scheme, $R^{71}$ is an alkyl group and the other symbols are the same as defined above.

Reaction Step C1-1:

The reaction of the compound [II-Ac] with azidating agent can be carried out in a solvent in the presence of a base. Examples of the solvent include any solvent which does not disturb the reaction, such as acetone, benzene, toluene, tetrahydrofuran, diethylether and the like. Examples of the azidating agent include diphenyl-phosphorylazide, sodium azide and the like. Examples of the base include pyridine, triethylamine, diisopropylethylamine, 4-methylmorpholine, 1,8-diazabicyclo[5,4,0]-undecene and the like. The azidating agent can be used in an amount of 1.0 to 5.0 moles, preferably 1.1 to 2.0 moles per one mole of the compound [II-Ac]. The base can be used in an amount of 1.0 to 10.0 moles, preferably 1.1 to 3.0 moles per one mole of the compound [II-Ac]. The reaction can be carried out at −30 to 50° C., preferably −10 to 10° C.

Reaction Step C1-2:

The preparation of the compound [XXIV] by Crutius rearrangement reaction can be carried out in a solvent under heating. Examples of the solvent include any solvent which does not disturb the reaction, such as benzene, toluene, dioxane, chloroform and the like. The reaction can be carried out at 40 to 200° C., preferably 60 to 120° C.

Reaction Step C1-3:

The treatment of the compound [XXIV] with an acid can be carried out in or without a solvent. Examples of the solvent include any solvent which does not disturb the reaction, such as water and the like. Examples of the acid include a strong acid such as sulfuric acid, hydrochloric acid, nitric acid, trifluoroacetic acid, hydrobromic acid and the like. The acid can be used in an amount of 2.0 to 10.0 moles, preferably 3.0 to 5.0 moles per one mole of the compound [XXIV]. The reaction can be carried out at 0 to 200° C., preferably 40 to 120° C.

Reaction Step C1-4:

The alkylation of the compound [II-Ca] can be carried out in a solvent by, for example, 1) in the presence of a base (e.g., sodium hydride, potassium carbonate, pyridine, triethylamine, diisopropylethylamine, 4-methylmorpholine, 1,8-diazabicyclo-[5,4,0]undecene and the like) and an alkylhalide of the formula [XXV]:

$$R^{72}\text{-}X^4 \quad [XXV]$$

wherein $R^{72}$ is an alkyl group and $X^4$ is a halogen atom; or 2) in the presence of a reducing agent (e.g., lithium aluminum hydride, sodium borohydride, sodium cyanoborohydride, sodium triacetoxyborohydride and the like), an acid (e.g., acetic acid, formic acid and the like) and an aldehyde compound [XXVI]:

$$R^{73}\text{—CHO} \quad [XXVI]$$

wherein $R^{73}$ is an alkyl group; or 3) in the presence of an activating agent (e.g., diethyl azodicarboxylate and the like), a tri-substituted phosphine (e.g., triphenylphosphine, tributylphosphine and the like) and an alkanol compound of the formula [XXVII]:

$$R^{74}\text{—OH} \quad [XXVII]$$

wherein $R^{74}$ is an alkyl group. Examples of the solvent include any solvent which does not disturb the reaction, such as methylene chloride, chloroform, dimethylformamide, dimethylacetamide, dimethylsulfoxide, tetrahydrofuran, dioxane, toluene, benzene, 1,2-dichloroethane, 1-methylpyrrolidinone, 1,2-dimethoxyethane and the like. The reaction can be carried out at −20 to 100° C., preferably 0 to 40° C.

Meanwhile, if required, an appropriate protecting group (e.g., an alkyloxycarbonyl group such tert-butoxycarbonyl group, an arylalkyloxycarbonyl group such as benzyloxycarbonyl group and the like) may be introduced to 3-amino group in the compound [II-Ca] prior to the alkylation thereof. Such protecting group can be introduced or removed by a conventional manner depending on the kind of said protecting group.

The compound [II-Cb] can be also prepared by conducting the above Crutius rearrangement reaction (reaction Step C1-2) in an alkanol of the formula [e]:

$$R^e\text{—OH} \quad [e]$$

wherein $R^e$ is tert-butyl group or benzyl group to obtain a compound of the following formula [II-Ae]:

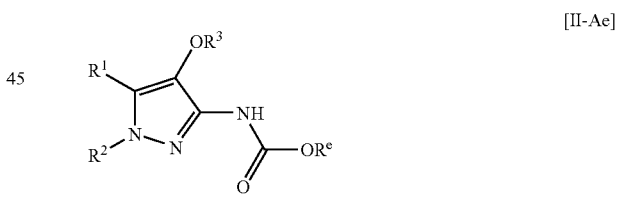

reacting such compound [II-Ae] with the alkylhalide compound [XXV] or the alkanol compound [XXVII] to give a compound of the formula [II-Af]:

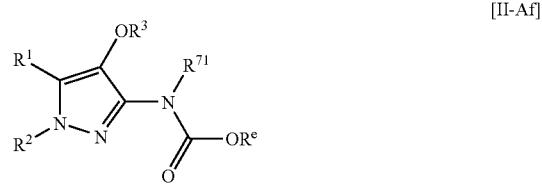

wherein the symbols are the same as defined above, and then removing the acyl moiety of the formula: $R^eOCO\text{—}$. The removal of the acyl moiety can be conducted by (1) treatment with an acid such as hydrochloric acid, trifluoroacetic acid, hydrobromic acid and the like; or (2) heating at about 150° C.; or (3) catalytic hydrogenation.

The compound [II-F] can be prepared by reacting a compound [II-Aa] with a compound [b1] (e.g., an alkyl lithium such as methyl lithium) in a solvent such as tetrahydrofuran and then reacting the product with a compound [b2] in which $R^c$ is a vinyl group (e.g., vinyl magnesium bromide).

The compound [II-G] can be obtained by reacting a compound [II-Aa] with a hydrazine compound of the formula [12]:

wherein Z is an acyl group or a salt thereof in the same manner as described in the Method A and then removing the acyl group (Z) from the product.

Throughout the present description and claims, the "halogen atom" means fluorine, chlorine, iodine or bromine atom. The "alkyl group" means a straight or branched chain alkyl group having 1 to 6 carbon atoms, preferably 1 to 4 carbon atoms. The "cycloalkyl group" means a cycloalkyl group having 3 to 8 carbon atoms, preferably 5 to 7 carbon atoms. The "alkylene group" means a straight or branched chain alkylene group having 1 to 6 carbon atoms, preferably 1 to 3 carbon atoms.

EXAMPLES

The compounds of the present invention are illustrated in more detail by the following Examples but should not be construed to be limited thereto.

Example 1

To a solution of 3-carboxy-1-(2-chlorophenyl)-5-(4-chlorophenyl)-4-methoxy-1H-pyrazole (3.5 g, compound obtained in Reference Example 1(6)) in methylene chloride (100 mL) was added N-aminomorpholine (1.47 g, water-soluble carbodiimide HCl (2.76 g) and 1-hydroxybenzotriazole hydrate (2.21 g), and the mixture was stirred at room temperature overnight. To the reaction mixture was added an aqueous sodium hydrogencarbonate solution and the mixture was stirred and extracted with chloroform. The organic layer was dried over magnesium sulfate and filtered. The filtrate was concentrated in vacuo and the crude product was purified by column chromatography on silica gel (solvent: hexane/ethyl acetate=40/60 to 20/80) to obtain 1-(2-chloro-phenyl)-5-(4-chlorophenyl)-4-methoxy-3-(N-morpholinocarbamoyl)-1H-pyrazole (3.49 g; yield: 81%) as a powder.

MS (APCI) m/z; 447/449[M+H]$^+$

Example 2

To a solution of the compound obtained in Reference Example 1(6) (73 mg) in methylene chloride (2 mL) was added oxalyl chloride (21 μL) and a drop of dimethylformamide at room temperature, and the mixture was stirred at the same temperature for 1 hour. The reaction mixture was concentrated and the residue was diluted with tetrahydrofuran (2 mL). Thereto was added N-aminopyrrolidine HCl (123 mg) and triethylamine (279 μL) and the mixture was stirred at room temperature for 2 hours. To the reaction mixture was added 1N HCl solution (800 μL) and the mixture was stirred. Thereto was added ethyl acetate and the organic layer was extracted by diatomaceous earth column (CHEM ELUTE, VARIAN Inc.). The extract was concentrated in vacuo and the resultant crude product was purified by column chromatography on silica gel (Chromatorex NH silica gel, Fuji Silicia Chem., Co., Ltd., solvent: hexane/ethyl acetate=50/50 to 30/70) to obtain 1-(2-chlorophenyl)-5-(4-chlorophenyl)-4-methoxy-3-[N-(1-pyrrolidinyl)carbamoyl]-1H-pyrazole (43 mg; yield: 50%) as a powder.

MS (APCI) m/z; 431/433[M+H]$^+$

Example 3

(1) To a solution of the compound obtained in Reference Example 1(6) (2.5 g) in tetrahydrofuran (100 mL) was gradually added dropwise methyl lithium (1.04 M ether solution, 13.9 mL) under nitrogen gas atmosphere at 0° C. and the mixture was stirred at the same temperature for 30 minutes and at room temperature for 3 hours. To the reaction mixture was added water and ethyl acetate under ice-cooling and the mixture was stirred. The organic layer was washed with an aqueous sodium hydrogencarbonate solution, dried over magnesium sulfate and filtered. The filtrate was concentrated in vacuo and the resultant crude product was purified by column chromatography on silica gel (solvent: hexane/ethyl acetate=90/10 to 85/15) to obtain 3-acetyl-1-(2-chlorophenyl)-5-(4-chlorophenyl)-4-methoxy-1H-pyrazole (1.1 g, yield: 43%) as a solid.

MS (APCI) m/z; 361/363[M+H]$^+$ (2) To a solution of the compound obtained in the above step (1) (60 mg) in chloroform (3 mL) was added dropwise bromine (8.5 μL) and the mixture was stirred at room temperature for 3 hours. The reaction mixture was concentrated and the residue was diluted with dimethylformamide (3 mL). Thereto was added morpholine (146 μL) and the mixture was stirred at room temperature for 2 hours. To the reaction mixture was added water and ethyl acetate and the mixture was stirred. The organic layer was extracted by diatomaceous earth column (CHEM ELUTE, VARIAN Inc.). The extract was concentrated in vacuo and the resultant crude product was purified by column chromatography on silica gel (Chromatorex NH silica gel, Fuji Silicia Chem., Co., Ltd., solvent: hexane/ethyl acetate=80/20 to 65/35) and the eluted fraction was concentrated in vacuo. The resultant product was dissolved in tert-buthanol and then lyophilized to obtain 3-(1-morpholinoacetyl)-1-(2-chlorophenyl)-5-(4-chlorophenyl)-4-methoxy-1H-pyrazole (26.8 mg, yield: 36%) as a powder.

MS (APCI) m/z; 446/448[M+H]$^+$

Examples 4 to 13

The corresponding starting materials were treated in the same manner as described in either one of Examples 1 to 3 to obtain the compounds as shown in the following Table 1.

TABLE 1

(No. 1)

| Ex. Nos. | $R^3$ | —N($R^5$)($R^6$) | Physicochemical properties etc. |
|---|---|---|---|
| 4 | $CH_3$ | H, CF$_3$ (N-ethyl-CF$_3$) | solid MS(APCI): 444/446 [M + H]$^+$ |

TABLE 1-continued

| Ex. Nos. | R³ | —N(R⁵)(R⁶) | Physicochemical properties etc. |
|---|---|---|---|
| 5 | CH₃ | HN—N(piperidine) | solid MS(APCI): 445/447 [M + H]⁺ |
| 6 | CH₃ | HN—cyclohexyl | solid MS(ESI): 444 [M + H]⁺ |
| 7 | C₂H₅ | HN—N(piperidine) | solid MS(APCI): 459/461 [M + H]⁺ |
| 8 | CH₃O(CH₂)₂— | HN—N(piperidine) | solid MS(APCI): 489/491 [M + H]⁺ |
| 9 | C₂H₅ | HN—N(morpholine) | solid MS(APCI): 461/463 [M + H]⁺ |

(No. 2)

[Structure: 5-(4-chlorophenyl)-1-(2-chlorophenyl)-pyrazole with OR³ at 4-position and C(=O)N(R⁵)(R⁶) at 3-position]

| Ex. Nos. | R³ | —N(R⁵)(R⁶) | Physicochemical properties etc. |
|---|---|---|---|
| 10 | CH₃ | HN—tetrahydropyran-4-yl | solid MS(APCI): 446/448 [M + H]⁺ |
| 11 | CH₃ | HN—azepane | solid MS(APCI): 459/461 [M + H]⁺ |
| 12 | CH₃ | HN—N(CH₃)₂ | solid MS(APCI): 405/407 [M + H]⁺ |

TABLE 1-continued (No. 3)

[Structure: 5-(4-chlorophenyl)-1-(2-chlorophenyl)-4-methoxy-pyrazole with C(=O)CH₂N(R⁵)(R⁶) at 3-position]

| Ex. Nos. | —N(R⁵)(R⁶) | Physicochemical properties etc. |
|---|---|---|
| 13 | —N(piperidine) | solid MS(APCI): 444/446 [M + H]⁺ |

Example 14

To a solution of 3-carboxyl-1-(2-chlorophenyl)-5-(4-chlorophenyl)-4-methoxy-1H-pyrazole 290 mg, compound obtained in Reference Example 1(6)) in methylene chloride/dimethylformamide (6 mL/0.5 mL) was added 4-tetrahydrothiopyranylamine (140 mg, compound obtained in Reference Example 12(2)), water-soluble carbodiimide HCl (230 mg) and 1-hydroxybenzotriazole hydrate (184 mg), and the mixture was stirred at room temperature overnight. To the reaction mixture was added an aqueous sodium hydrogencarbonate solution and the mixture was stirred and extracted with chloroform. The extract was concentrated in vacuo and the crude product was purified by column chromatography on silica gel (solvent: hexane/ethyl acetate=85/15 to 70/30) to obtain 1-(2-chlorophenyl)-5-(4-chlorophenyl)-4-methoxy-3-[N-(4-tetrahydrothiopyranyl)carbamoyl]-1H-pyrazole (323 mg; yield: 87%) as a colorless solid.

MS (APCI) m/z; 462/464 [M+H]⁺

Example 15

To a solution of the compound obtained in Example 14 (116 mg) in methylene chloride (4 mL) was added trifluoroacetic acid (77 µL) at 0° C. and the mixture was stirred at room temperature for 30 minutes. To the reaction mixture was added 3-chloroperbenzoic acid (58 mg, water content: 25%) and the mixture was stirred at the same temperature for 1 hour and at room temperature for 2 hours. To the reaction mixture was added an aqueous sodium hydrogencarbonate solution and the mixture was stirred and extracted with chloroform. The extract was concentrated in vacuo and the crude product was purified by column chromatography on silica gel (solvent: hexane/ethyl acetate=50/50 to 30/70→chloroform/methanol=100/0 to 95/5) to obtain 1-(2-chlorophenyl)-5-(4-chlorophenyl)-4-methoxy-3-[N-[4-(1-oxo-tetrahydrothiopyranyl)carbamoyl]-1H-pyrazole (28.5 mg; yield: 24%) as a colorless solid.

MS (APCI) m/z; 478/480 [M+H]⁺

Example 16

The compound obtained in Example 14 (116 mg) was treated in the same manner, except for using 115 mg of 3-chloroperbenzoic acid, as described in Example 15 to obtain 1-(2-chlorophenyl)-5-(4-chlorophenyl)-4-methoxy-3-[N-[4-(1,1-dioxo-tetrahydrothiopyranyl)carbamoyl]-1H-pyrazole (69 mg; yield: 56%) as a colorless solid.

MS (APCI) m/z; 494/496 [M+H]$^+$

Example 17

To a solution of the compound obtained in Reference Example 1(6) (73 mg) in methylene chloride (3 mL) was added 4 tetrahydrothiopyranol (61 mg) and 4-dimethylaminopyridine (20 mg) and the mixture was stirred. Thereto was added dicyclohexylcarbodiimide (45 mg) at 0° C. and the mixture was stirred at room temperature overnight. To the reaction mixture was added an aqueous sodium hydrogencarbonate solution and the mixture was stirred and extracted with chloroform. The extract was concentrated in vacuo and the crude product was purified by column chromatography 'on silica gel (solvent: hexane/ethyl acetate =77/23 to 53/47) to obtain 1-(2-chlorophenyl)-5-(4-chlorophenyl)-4-methoxy-3-(4-tetrahydrothiopyranyloxy)carbonyl)-1H-pyrazole (53 mg; yield: 59%) as a colorless solid.

MS (APCI) m/z; 447/449 [M+H]$^+$

Example 18

To a solution of the compound obtained in Reference Example 1(6) (73 mg) in toluene (3 mL) was added diphenylphosphorylazide (47 μL) and triethylamine (33 μL) at 0° C. under nitrogen-gas atmosphere and the mixture was stirred at 80° C. overnight. To the reaction mixture was added 4-tetrahydropyranylamine (36 mg) and 4-dimethyl-aminopyridine (2.4 mg) under ice-cooling and the mixture was stirred at 80° C. overnight. To the reaction mixture was added an aqueous sodium hydrogencarbonate solution. The mixture was stirred and extracted by diatomaceous earth column (CHEM ELUTE, VARIAN Inc.). The extract was concentrated in vacuo and the resultant crude product was purified by column chromatography on silica gel (solvent: hexane/ethyl acetate=60/40 to 20/80) to obtain 1-(2-chlorophenyl)-5-(4-chlorophenyl)-4-hydroxy-3-[N'-(4-tetrahydropyranyl)ureido]-1H-pyrazole (10 mg; yield: 11%) as a colorless solid.

MS (APCI) m/z; 461/463 [M+H]$^+$

Example 19

(1) The compound obtained in Reference Example 17 (513 mg) and 3-amino-1-tert-butoxycarbonylazetidine were treated in the same manner as described in Example 1 to obtain 1-(2,4-dichlorophenyl)-5-(4-chlorophenyl)-4-methoxy-3-[N-[3-(1-tert-butoxycarbonyl)azetidyl]carbamoyl]-1H-pyrazole (590 mg, yield: 83%) as a solid.

MS (APCI) m/z; 551/553 [M+H]$^+$ (2) To a solution of the compound obtained in the above step (1) (590 mg) in chloroform (5 mL) was added 4 N HCl-ethyl acetate (2 mL) and the mixture was stirred at room temperature overnight. The reaction mixture was concentrated in vacuo and to the residue was added ethyl acetate and an aqueous sodium hydrogencarbonate solution. The mixture was stirred and the organic layer was dried over magnesium sulfate and filtered. The filtrate was concentrated in vacuo and the residue was diluted with methylene chloride (2 mL). Thereto was added triethylamine (30 mL) and p-chlorobenzoyl chloride (35 mg) and the mixture was stirred at room temperature overnight. To the reaction mixture was added an aqueous citric acid solution and the mixture was stirred. The organic layer was washed with an aqueous saturated sodium hydrogencarbonate solution and a brine, dried over magnesium sulfate and filtered. The filtrate was concentrated in vacuo and the residue was diluted with dimethylformamide (1 mL). Thereto was added sodium hydride (4 mg) and the mixture was stirred at 80° C. for 2 days. After cooling to room temperature, to the reaction mixture was added water and ethyl acetate and the organic layer was extracted with ethyl acetate. The extract was concentrated in vacuo and the resultant crude product was purified by column chromatography on silica gel (solvent: hexane/ethyl acetate=0/100) to obtain 1-(2,4-dichlorophenyl)-5-(4-chlorophenyl)-4-hydroxy-3-[N-[3-(4-chlorobenzoyl)azetidyl]carbamoyl]-1H-pyrazole (30 mg; yield: 52%) as a powder.

MS (APCI) m/z; 589/591 [M+H]$^+$

Example 20

(1) To a solution of 3-carboxyl-1-(2-chlorophenyl)-5-(4-chlorophenyl)-4-methoxy-1H-pyrazole (363 mg, compound obtained in Reference Example 1(6)) in methylene chloride (5 mL) was added 1-tert-butoxycarbonyl-3-aminopyrrolidine (279 mg), water-soluble carbodiimide HCl (288 mg) and 1-hydroxybenzotriazole hydrate (230 mg), and the mixture was stirred at room temperature overnight. To the reaction mixture was added an aqueous sodium hydrogencarbonate solution and the mixture was stirred and extracted with chloroform. The extract was concentrated in vacuo and the crude product was purified by column chromatography on silica gel (solvent: hexane/ethyl acetate=75/25 to 55/45) and dissolved in tert-butyl alcohol. The solution was lyophilized to obtain 3-[N-[3-(1-tert-butoxycarbonyl)pyrrolidinyl]-carbamoyl]-1-(2-chlorophenyl)-5-(4-chlorophenyl)-4-methoxy-1H-pyrazole (516 mg; yield: 97%) as a colorless powder.

MS (APCI) m/z; 431/433 [M+H-Boc]$^+$ (Boc: tert-butoxycarbonyl)

(2) To a solution of the compound obtained in the above step (1) (425 mg) in dioxane (2 mL) was added 4N HCl-dioxane (3 mL) at 0° C. and the mixture was stirred at the same temperature for 2 hours and at room temperature for 2 hours. To the reaction mixture was added an aqueous hydrogencarbonate solution to basify. The mixture was stirred and extracted by diatomaceous earth column (CHEM ELUT, VARIAN Inc.). The extract was concentrated in vacuo to obtain 1-(2-chlorophenyl)-5-(4-chlorophenyl)-4-methoxy-3-[N-(3-pyrrolidinyl)carbamoyl]-1H-pyrazole (344 mg; yield: 100%) as a colorless viscosity.

MS (APCI) m/z; 431/433 [M+H]$^+$ (3) To a solution of the compound obtained in the above step (2) (86 mg) in methanol (3 mL) was added triethylamine (112 μL) and trifluoroacetic anhydride (56 μL) at 0° C. and the mixture was stirred at room temperature overnight. To the reaction mixture was added an aqueous hydrogencarbonate solution and the mixture was stirred and extracted by diatomaceous earth column (CHEM ELUTE, VARIAN Inc.). The extract was concentrated in vacuo to obtain 1-(2-chlorophenyl)-5-(4-chlorophenyl)-4-methoxy-3-[N-[3-(1-trifluoroacetyl)pyrrolidinyl]carbamoyl]-1H-pyrazole (90 mg; yield: 86%) as a colorless powder.

MS (APCI) m/z; 527/529 [M+H]$^+$

Example 21

(1) To a solution of 3-carboxyl-1-(2-chlorophenyl)-5-(4-chlorophenyl)-4-methoxy-1H-pyrazole (3.5 g, compound obtained in Reference Example 1(6)) in methylene chloride (20 mL) was added N-tert-butoxycarbonylhydrazine (297 mg), water-soluble carbodiimide HCl (431 mg) and 1-hydroxybenzotriazole hydrate (345 mg), and the mixture was stirred at room temperature for 4 hours. To the reaction mixture was added an aqueous sodium hydrogencarbonate solution and the mixture was stirred and extracted with chloroform. The extract was concentrated in vacuo and the crude product was purified by column chromatography on silica gel (solvent: hexane/ethyl acetate=80/20 to 60/40) and dissolved in tert-butyl alcohol. The solution was lyophilized to obtain 3-[[N'-(tert-butoxycarbonyl)hydrazino]carbonyl]-1-(2-chlorophenyl)-5-(4-chlorophenyl)-4-methoxy-1H-pyrazole (722 mg; yield: 100%) as a colorless powder.

MS (APCI) m/z; 477/479 [M+H]$^+$ (2) To a solution of the compound obtained in the above step (1) (3.43 g) in dioxane (10 mL) was added 4N HCl-dioxane (25 mL) at 0° C. and the mixture was stirred at 50° C. for 3 days. After cooling, to the reaction mixture was added an aqueous hydrogencarbonate solution and ethyl acetate. The mixture was stirred and extracted with ethyl acetate. The organic layer was dried over magnesium sulfate and filtered. The filtrate was concentrated in vacuo and the resultant crude product was dissolved in tert-butyl alcohol and lyophilized to obtain 3-hydrazinocarbonyl-1-(2-chlorophenyl)-5-(4-chlorophenyl)-4-methoxy-1H-pyrazole (2.64 g; yield: 100%) as a pale yellow powder.

MS (APCI) m/z; 377/379 [M+H]$^+$ (3) To a solution of the compound obtained in the above step (2) (76 mg) in methylene chloride (3 mL) was added 1-methanesulfonyl-piperidin-4-carboxylic acid (62 mg), water-soluble carbodiimide HCl (58 mg) and 1-hydroxybenzotriazole hydrate (46 mg) and the mixture was stirred at room temperature overnight. To the reaction mixture was added an aqueous hydrogencarbonate solution and the mixture was stirred and extracted with chloroform. The extract was concentrated in vacuo and the resultant crude product was purified by column chromatography on silica gel (solvent: hexane/ethyl acetate=98/2 to 90/10) to obtain 1-(2-chlorophenyl)-5-(4-chlorophenyl)-3-[[N'-[(1-methylsulfonylpiperidin-4-yl)carbonyl]hydrazino]carbonyl]-4-methoxy-1H-pyrazole (85.8 mg; yield: 76%) as a colorless powder.

MS (APCI) m/z; 566/568 [M+H]$^+$

Example 22

(1) To a solution of 3-carboxyl-1-(2-chlorophenyl)-5-(4-chlorophenyl)-4-methoxy-1H-pyrazole (1.96 g, compound obtained in Reference Example 1(6)) in methylene chloride (20 mL) was added 1-amino-4-tert-butoxycarbonylpiperazine (730 mg, compound obtained in Reference Example 16(2)), water-soluble carbodiimide HCl (1.0 g), 1-hydroxybenzotriazole hydrate (827 mg) and triethylamine (753 μL), and the mixture was stirred at room temperature overnight. To the reaction mixture was added an aqueous sodium hydrogencarbonate solution and the mixture was stirred and extracted with chloroform. The extract was concentrated in vacuo and the crude product was purified by column chromatography on silica gel (solvent: hexane/ethyl acetate=60/40 to 40/60) to obtain 3-[N-(4-tert-butoxycarbonylpiperazin-1-yl)-carbamoyl]-1-(2-chlorophenyl)-5-(4-chlorophenyl)-4-methoxy-1H-pyrazole (1.56 g; yield: 79%) as a colorless solid.

MS (APCI) m/z; 546/548 [M+H]$^+$ (2) To a solution of the compound obtained in the above step (1) (1.56 g) in dioxane (10 mL) was added 4N HCl-dioxane (20 mL) at room temperature and the mixture was stirred at 50° C. overnight. After cooling to room temperature, to the reaction mixture was added an aqueous hydrogencarbonate solution to basify. The mixture was stirred and extracted with chloroform. The extract was dried over magnesium sulfate and filtered. The filtrate was concentrated in vacuo to obtain 1-(2-chlorophenyl)-5-(4-chlorophenyl)-4-methoxy-3-[N-(piperazin-1-yl)carbamoyl]-1H-pyrazole (1.26 g; yield: 99%) as a colorless solid.

MS (APCI) m/z; 446/448 [M+H]$^+$ (3) To a solution of the compound obtained in the above step (3) (38 mg) in methylene chloride (1 mL) was added triethylamine (39 μL) and benzoyl chloride (16 μL) and the mixture was stirred at room temperature overnight. To the reaction mixture was added an aqueous hydrogencarbonate solution and the mixture was stirred and extracted with chloroform. The extract was concentrated in vacuo and the resultant crude product was purified by column chromatography on silica gel (solvent: hexane/ethyl acetate=40/60 to 0/100) to obtain 3-[N-(4-benzoylpiperazin-1-yl)-carbamoyl]-1-(2-chlorophenyl)-5-(4-chlorophenyl)-4-methoxy-1H-pyrazole (20 mg; yield: 53%) as a colorless solid.

MS (APCI) m/z; 550/552 [M+H]$^+$

Example 23

To a solution of the compound obtained in Example 21(1) (95 mg) in dioxane (5 mL) was added 4N HCl-dioxane (6 mL) at 0° C. and the mixture was stirred at 50° C. for 2 hours. After cooling, to the reaction mixture was added an aqueous hydrogencarbonate solution to basify. The organic layer was extracted by diatomaceous earth column (CHEM ELUTE, VARIAN Inc.) and the extract was concentrated in vacuo to obtain 3-hydrazinocarbonyl-1-(2-chlorophenyl)-5-(4-chlorophenyl)-4-methoxy-1H-pyrazole (1.26 g; yield: 99%) as a crude product. To the crude product was added ethanol (2 mL), triethylamine (28 μL) and divinylsulfone (24 μL) and the mixture was refluxed under heating and nitrogen-gas atmosphere for 5 hours. After cooling, to the reaction mixture was added water and the mixture was stirred. The organic layer was extracted by diatomaceous earth column (CHEM ELUT, VARIAN Inc.) and the extract was concentrated in vacuo. The resultant crude product was purified successively by column chromatography on silica gel (solvent: chloroform/methanol=100/0 to 96/4) and column chromatography on NH-silica gel (Chromatorex NH-silica gel, Fuji Silicia Chem., solvent: hexane/ethyl acetate=40/60 to 20/80) to obtain 1-(2-chlorophenyl)-5-(4-chlorophenyl)-3-[N-(1,1-dioxo-thiomorpholino)carbamoyl]-4-methoxy-1H-pyrazole (43 mg; yield: 50%) as a colorless solid.

MS (APCI) m/z; 495/497 [M+H]$^+$

Example 24A

To a solution of the compound obtained in Example 22(2) (67 mg) in methylene chloride (2 mL) was added water-soluble carbodiimide HCl (44 mg) and 1-hydroxybenzotriazole hydrate (35 mg) and the mixture was stirred at room temperature overnight. To the reaction mixture was added an aqueous sodium hydrogencarbonate solution and the mixture was stirred and extracted with chloroform. The extract was concentrated in vacuo and the crude product was purified by column chromatography on silica gel (solvent: hexane/ethyl acetate=40/60 to 0/100) to obtain 3-[N-[4-(5-bromo-2-thenoyl)piperazin-1-yl)carbamoyl]-1-(2-chlorophenyl)-5-(4-chloro phenyl)-4-methoxy-1H-pyrazole (79 mg; yield: 79%) as a solid.

MS (APCI) m/z; 634/636 [M+H]$^+$

Example 24B

To a solution of the compound obtained in Example 24A (49 mg) in dimethylformamide (1 mL) was added zinc cyanide (6 mg), tris(dibenzylideneacetone)-dipalladium (1.5 mg) and 1,1'-bis(diphenylphosphino)ferrocene (DPPF, 1.8 mg) and the mixture was stirred at 180° C. for 15 minutes in a microwave reactor. After cooling to room temperature, to the reaction mixture was added water and ethyl acetate. The mixture was stirred and the organic layer was extracted by diatomaceous earth column (CHEM ELUTE, VARIAN Inc.) and the extract was concentrated in vacuo. The extract was concentrated in vacuo and the crude product was purified by column chromatography on silica gel (solvent: hexane/ethyl acetate=30/70 to 0/100) to obtain 3-[N-[4-(5-cyano-2-thenoyl)piperazin-1-yl]carbamoyl]-1-(2-chlorophenyl)-5-(4-chloro-phenyl)-4-methoxy-1H-pyrazole (79 mg; yield: 83%) as a colorless solid.

MS (APCI) m/z; 581/583 [M+H]$^+$

Example 25

(1) To a solution of the compound obtained in Reference Example 7 (72 mg) in chloroform (3 mL) was dropwise added bromine (15 μL) and the mixture was stirred at room temperature for 1 hour. The reaction mixture was concentrated in vacuo and the residue was diluted with dimethylformamide (3 mL). Thereto was added morpholine (87 μL) and the mixture was stirred at room temperature for 2 hours. To the reaction mixture was added an aqueous sodium hydrogencarbonate solution. After stirring, the mixture was treated by diatomaceous earth column (CHEM ELUTE, VARIAN Inc.) to extract an organic layer. The extract was concentrated in vacuo and the resultant crude product was purified by column chromatography on silica gel (solvent: hexane/ethyl acetate=60/40 to 40/60) to obtain 1-(2-chlorophenyl)-5-(4-chlorophenyl)-4-methoxy-3-(2-morpholinoacetyl)-1H-pyrazole.

(2) To the compound obtained in the above step (1) was added dimethylformamide (3 mL) and thereto was added sodium hydride (8.8 mg) at 0° C. The mixture was stirred at room temperature under nitrogen-gas atmosphere for 1 hour. To the reaction mixture was added an aqueous sodium hydrogencarbonate solution. After stirring, the mixture was treated by the diatomaceous earth column mentioned above to extract an organic layer. The extract was concentrated in vacuo and the resultant crude product was purified successively by column chromatography on silica gel (solvent: hexane/ethyl acetate=60/40 to 40/60) and gel-permeation chromatography (column: JAIGEL-1H and 2H, mobile phase: chloroform) to obtain 1-(2-chloro-phenyl)-5-(4-chlorophenyl)-4-methoxy-3-(2-morpholino)propionyl]-1H-pyrazole (10.3 mg, Total yield through the step (1) to (2): 11%) as a colorless powder.

MS (APCI) m/z; 581/583 [M+H]$^+$

Example 26

The compound obtained in Reference Example 5(2) and 1-aminopyrrolidine were treated in the same manner as described in Example 1 to obtain 1-(2-chloro-phenyl)-5-(4-chlorophenyl)-4-methoxycarbonylmethoxy-3-[N-(1-pyrrolidinyl)carbamoyl]-1H-pyrazole (71.3 mg, yield: 73%) as a solid.

MS (APCI) m/z; 489/491 [M+H]$^+$

Example 27

To a solution of the compound obtained in Example 26 (50 mg) in methanol (5 mL) was added 6N-ammonia-methanol (1 mL) and the mixture was stirred at room temperature overnight. To the reaction mixture was added ethyl acetate and water and the mixture was stirred. The organic layer was separated and concentrated in vacuo. The resultant crude product was purified by column chromatography on silica gel (solvent: hexane/ethyl acetate=50/50 to 30/70) to obtain 4-carbamoylmethoxy-1-(2-chlorophenyl)-5-(4-chlorophenyl)-3-[N-(1-pyrrolidinyl)carbamoyl]-1H-pyrazole (10.2 mg, yield: 11%) as a pale yellow solid.

MS (APCI) m/z; 474/476 [M+H]$^+$

Example 28

To a solution of the compound obtained in Example 21(3) 884 mg) in methylene chloride (2 mL) was added 2-chloro-1,3-dimethylimidazolinium chloride (40 mg) and triethylamine (62 μL) and the mixture was stirred at room temperature overnight. To the reaction mixture was added an aqueous sodium hydrogencarbonate solution and the mixture was stirred and extracted with chloroform. The extract was concentrated in vacuo and the crude product was purified by column chromatography on silica gel (solvent: hexane/ethyl acetate=40/60 to 10/90) to obtain 1-(2-chlorophenyl)-5-(4-chlorophenyl)-4-methoxy-3-[2-(1-methylsulfonylpiperidin-4-yl)-1,3,4-oxadiazol-5-yl]-1H-pyrazole (21.8 mg; yield: 26%) as a colorless solid.

MS (APCI) m/z; 548/550 [M+H]$^+$

Example 29

3-Amino-1-(2-chlorophenyl)-5-(4-chlorophenyl)-4-methoxy-1H-pyrazole (33 mg, the compound obtained in Reference Example 6) and cyclohexanecarboxylic acid (12 mg) were treated in the same manner as described in Example 1 to obtain 1-(2-chlorophenyl)-5-(4-chlorophenyl)-3-cyclohexylcarbonylamino-4-methoxy-1H-pyrazole (28 mg, yield: 63%) as a solid.

MS (APCI) m/z; 444/446 [M+H]$^+$

Example 30

To a solution of the compound obtained in Reference Example 1(6) (73 mg) in toluene (3 mL) was added diphenylphosphorylazide (47 μL) and triethylamine (33 μL) at 0° C. under nitrogen-gas atmosphere and the mixture was stirred at the same temperature for 30 minutes, at room temperature for 1 hour and at 80° C. for 2 hours. To the reaction mixture was added 4-tetrahydropyranol (37 mg) and 4-dimethylaminopyridine (2.4 mg) under ice-cooling and the mixture was stirred at 80° C. overnight. To the reaction mixture was added an aqueous sodium hydrogencarbonate solution at 0° C. The mixture was stirred and extracted by diatomaceous earth column (CHEM ELUTE, VARIAN Inc.). The extract was concentrated in vacuo and the resultant crude product was purified by column chromatography on silica gel (solvent: hexane/ethyl acetate=70/30 to 60/40) to obtain 1-(2-chlorophenyl)-5-(4-chlorophenyl)-3-[[(tetrahydropyran-4-yloxy)carbonyl]amino]-4-methoxy-1H-pyrazole (16 mg; yield: 17%) as a colorless solid.

MS (APCI) m/z; 462/464 [M+H]$^+$

Example 31

The corresponding starting materials were treated in the same manner as described in Example 1 to obtain 1,5-bis(4-chlorophenyl)-4-methoxy-3-[N-(pyrrolidinyl)carbamoyl]-1H-pyrazole (32 mg, yield: 74%) as a powder.

MS (ESI) m/z; 431.05 [M+H]$^+$

Example 32

To a solution of the compound obtained in Example 20(2) (86 mg) in methylene chloride (3 mL) was added triethylamine (112 µL) and acetyl chloride (28 □L) and the mixture was stirred at room temperature overnight. To the reaction mixture was added an aqueous sodium hydrogencarbonate solution at 0° C. The mixture was stirred and extracted by diatomaceous earth column (CHEM ELUTE, VARIAN Inc.). The extract was concentrated in vacuo and the resultant crude product was purified by column chromatography on silica gel (solvent: chloroform/methanol=100/0 to 94/6) to obtain 1-(2-chlorophenyl)-5-(4-chlorophenyl)-4-methoxy-3-[N-(1-acetyl-3-pyrrolidinyl)carbamoyl]-1H-pyrazole (86 mg; yield: 91%) as a powder.

MS (APCI) m/z; 473/475 [M+H]$^+$

Example 33

The compound obtained in Example 20 (2) (86 mg) and methanesulfonyl chloride were treated in the same manner as described in Example 32 to obtain 1-(2-chlorophenyl)-5-(4-chlorophenyl)-4-methoxy-3-[N-(1-methylsulfonyl-3-pyrrolidinyl)-carbamoyl]-1H-pyrazole (84 mg, yield: 83%) as a powder.

MS (APCI) m/z; 509/511 [M+H]$^+$

Example 34

The compound obtained in Example 20 (2) (86 mg) and N,N-dimethyl-sulfamoyl chloride were treated in the same manner as described in Example 32 to obtain 1-(2-chlorophenyl)-5-(4-chlorophenyl)-4-methoxy-3-[N-[1-(N,N-dimethyl-sulfamoyl)-3-pyrrolidinyl]carbamoyl]-1H-pyrazole (62 mg, yield: 57%) as a powder.

MS (APCI) m/z; 538/540 [M+H]$^+$

Example 35

The corresponding starting materials were treated in the same manner as described in Example 25 (1) to obtain 1-(2-chlorophenyl)-5-(4-chlorophenyl)-4-methoxy-3-[1-(cis-2,6-dimethylpiperidino)acetyl]-1H-pyrazole (46 mg, yield: 49%) as a solid.

MS (APCI) m/z; 472/474 [M+H]$^+$

Example 36

The corresponding starting materials were treated in the same manner as described in Example 25 (1) to obtain 1-(2-chlorophenyl)-5-(4-chlorophenyl)-4-methoxy-3-[1-(1,1-dioxothiomorpholino)acetyl]-1H-pyrazole (73 mg, yield: 74%) as a solid.

MS (APCI) m/z; 472/474 [M+H]$^+$

Example 37

To a solution of the compound obtained in Example 21 (1) (95 mg) in dioxane (1 mL) was added 4N HCl-dioxane (3 mL) at 0° C. and the mixture was stirred at 40° C. for 2 hours. After cooling to room temperature, to the reaction mixture was added an aqueous sodium hydrogencarbonate solution. The mixture was stirred and extracted by diatomaceous earth column (CHEM ELUTE, VARIAN Inc.). The extract was concentrated in vacuo and the resultant crude product was purified by column chromatography on silica gel (solvent: chloroform/methanol=19/1) to obtain 1-(2-chlorophenyl)-5-(4-chlorophenyl)-4-methoxy-3-[N-[1-(2-oxo)piperidyl]carbamoyl]-1H-pyrazole (57 mg; yield: 62%) as a colorless solid.

MS (APCI) m/z; 459/461 [M+H]$^+$

Example 38

To a solution of the compound obtained in Reference Example 8 (75 mg) in ethanol (2 mL) was added morpholine (21 µL) and triethylamine (28 µL) and the mixture was refluxed under heating for 2 hours. After cooling to room temperature, to the reaction mixture was added water and ethyl acetate and the mixture was stirred and extracted by diatomaceous earth column (CHEM ELUTE, VARIAN Inc.). The extract was concentrated in vacuo and the resultant crude product was purified by column chromatography on silica gel (solvent: chloroform/methanol=100/0 to 95/5) to obtain 1-(2-chlorophenyl)-5-(4-chlorophenyl)-4-methoxy-3-(3-morpholinopropionyl)-1H-pyrazole (80.5 mg; yield: 87%) as a colorless solid.

MS (APCI) m/z; 460/462 [M+H]$^+$

Example 39

To a solution of the compound obtained in Reference Example 9 (2) (50 mg) in 1,2-dichloroethane (3 mL) was added triethylamine (42 µL) and triphosgen (89 mg) at 0° C. and the mixture was stirred at 60° C. for 2.5 hours. The reaction mixture was cooled to 0° C. and thereto was added water. The mixture was stirred and extracted with chloroform. The extract was concentrated in vacuo and the residue was diluted with methylene chloride. Thereto was added thiomorpholin-1,1-dioxide (41 mg) and the mixture was stirred at room temperature for 4 hours. To the reaction mixture was added an aqueous sodium hydrogencarbonate solution. The mixture was stirred and extracted with chloroform. The extract was concentrated in vacuo and the resultant crude product was purified by column chromatography on silica gel (solvent: hexane/ethyl acetate=45/55 to 20/80) to obtain 1-(2-chlorophenyl)-5-(4-chloro-phenyl)-3-[N-[(1,1-dioxothiomorpholino)carbonyl]amino]-4-methoxy-1H-pyrazole (23.4 mg; yield: 31%) as a colorless solid.

MS (APCI) m/z; 495/497 [M+H]$^+$

Examples 40 to 192

The corresponding starting materials were treated in the same manner as described in either one of Examples 1 to 3 to obtain the compounds as shown in the following Table 2.

TABLE 2
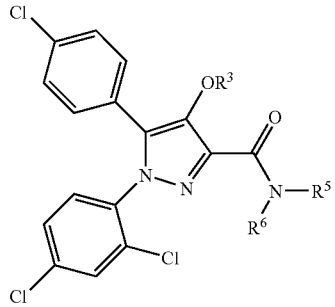
| Ex. Nos. | R³ | —N(R⁵)(R⁶) | Physicochemical properties etc. |
|---|---|---|---|
| (No. 1) | | | |
| 40 | CH₃— | 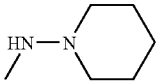 | powder MS (APCI): 479/481 [M + H]⁺ |
| 41 | CH₃— | 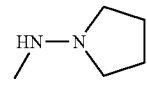 | powder MS (APCI): 465/467 [M + H]⁺ |
| 42 | CH₃— | 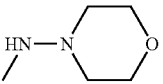 | powder MS (APCI): 481/483 [M + H]⁺ |
| 43 | CH₃— | 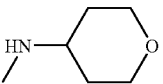 | powder MS (APCI): 480/482 [M + H]⁺ |
| 44 | CH₃— | —NH—N(CH₃)₂ | powder MS (APCI): 439/441 [M + H]⁺ |
| 45 | F₂CH— | 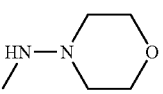 | powder MS (APCI): 517/519 [M + H]⁺ |
| 46 | F₂CH— | 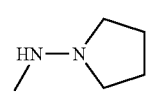 | powder MS (APCI): 501/503 [M + H]⁺ |
| (No. 2) | | | |
| 47 | CF₃CH₂— | 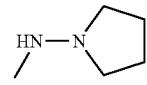 | powder MS (APCI): 533/535 [M + H]⁺ |
| 48 | CF₃CH₂— | 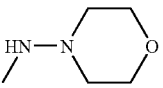 | powder MS (APCI): 549/551 [M + H]⁺ |
| 49 | CF₃CH₂— | 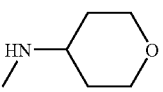 | powder MS (APCI): 548/550 [M + H]⁺ |
| 50 | CF₃CH₂— | 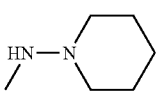 | powder MS (APCI): 547/549 [M + H]⁺ |

TABLE 2-continued

| Ex. Nos. | R³ | —N(R⁵)(R⁶) | Physicochemical properties etc. |
|---|---|---|---|
| 51 | CF₃CH₂— | —NH—N(CH₃)₂ | powder MS (APCI): 507/509 [M + H]⁺ |
| 52 | CH₃— | HN-C₆H₄-CF₃ (meta) with N-H | solid MS (APCI): 540/542 [M + H]⁺ |
| 53 | CH₃— | HN-pyridyl-CF₃ | solid MS (APCI): 541/543 [M + H]⁺ |
| 54 | CH₃— | HN-C₆H₄-CF₃ (para) | solid MS (APCI): 490/492 [M + H]⁺ |

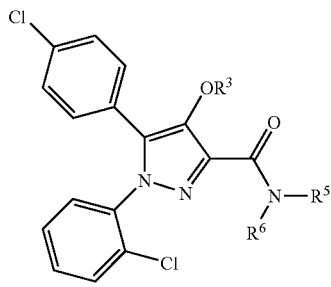

| Ex. Nos. | R³ | —N(R⁵)(R⁶) | Physicochemical properties etc. |
|---|---|---|---|
| (No. 3) | | | |
| 55 | CH₃— | HN-cyclopentyl | powder MS (APCI): 430/432 [M + H]⁺ |
| 56 | CH₃— | HN-cyclopropyl | powder MS (APCI): 402/404 [M + H]⁺ |
| 57 | CH₃— | HN-N(CH₃)-phenyl | powder MS (APCI): 467/469 [M + H]⁺ |
| 58 | CH₃— | HN-CH(CH₃)₂ | powder MS (APCI): 404/406 [M + H]⁺ |
| 59 | CH₃— | NH-CH₂-CH(CH₃)₂ | powder MS (APCI): 418/420 [M + H]⁺ |
| 60 | CH₃— | NH-CH₂-phenyl | powder MS (APCI): 452/454 [M + H]⁺ |
| 61 | 4-tetrahydropyranyl | HN-morpholino | powder MS (APCI): 517/519 [M + H]⁺ |

TABLE 2-continued

| Ex. No. | R³ (structure) | —N(R⁵)(R⁶) | Physicochemical properties etc. |
|---|---|---|---|
| 62 | 4-tetrahydropyranyl (via CH) | HN(CH₃)—N(pyrrolidinyl) | powder MS (APCI): 501/503 [M + H]⁺ |
| 63 | 4-tetrahydropyranyl (via CH) | HN(CH₃)—N(piperidinyl) | powder MS (APCI): 515/517 [M + H]⁺ |

Core structure: 1-(2-chlorophenyl)-5-(4-chlorophenyl)-4-(OR³)-pyrazole-3-carboxamide with N—R⁵/R⁶

Boc: tert-butoxycarbonyl group

| Ex. Nos. | R³ | —N(R⁵)(R⁶) | Physicochemical properties etc. |
|---|---|---|---|

(No. 4)

| Ex. No. | R³ | —N(R⁵)(R⁶) | Physicochemical properties etc. |
|---|---|---|---|
| 64 | —(CH₂)₂SCH₃ | HN(CH₃)—N(morpholinyl) | powder MS (APCI): 507/509 [M + H]⁺ |
| 65 | —(CH₂)₂—N(morpholinyl) | HN(CH₃)—N(morpholinyl) | powder MS (APCI): 546/548 [M + H]⁺ |
| 66 | —(CH₂)₂—N(morpholinyl) | HN(CH₃)—(4-tetrahydropyranyl) | powder MS (APCI): 545/547 [M + H]⁺ |
| 67 | —CH₃ | HN(CH₃)—N(4-methoxypiperidinyl) | powder MS (APCI): 475/477 [M + H]⁺ |
| 68 | —CH₃ | HN(CH₃)—N(3-methoxypyrrolidinyl) | powder MS (APCI): 461/463 [M + H]⁺ |
| 69 | —CH₃ | HN(CH₃)—N(piperidinyl-N-SO₂C₂H₅) | powder MS (APCI): 537/539 [M + H]⁺ |
| 70 | —CH₃ | HN(CH₃)—N(piperidinyl-N-SO₂N(CH₃)₂) | powder MS (APCI): 552/554 [M + H]⁺ |
| 71 | —CH₃ | HN(CH₃)—N(piperidinyl-N-Boc) | powder MS (APCI): 545/547 [M + H]⁺ |

TABLE 2-continued
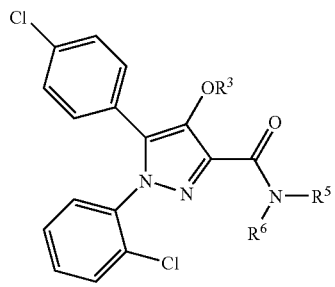
| Ex. Nos. | R³ | —N(R⁵)(R⁶) | Physicochemical properties etc. |
|---|---|---|---|
| (No. 5) | | | |
| 72 | CH₃ | 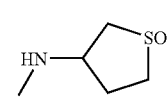 | powder MS (APCI): 480/482 [M + H]⁺ |
| 73 | CH₃ | 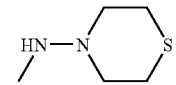 | powder MS (APCI): 463/465 [M + H]⁺ |
| 74 | CH₃ | 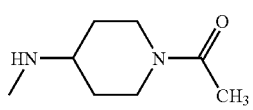 | powder MS (APCI): 487/489 [M + H]⁺ |
| 75 | CH₃ | 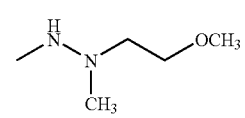 | viscidity MS (APCI): 449/451 [M + H]⁺ |
| 76 | CH₃ | 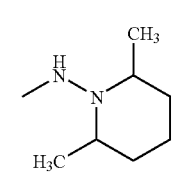 | powder MS (APCI): 473/475 [M + H]⁺ |
| 77 | 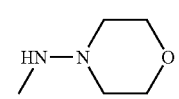 | 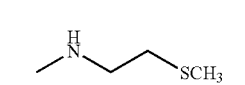 | powder MS (APCI): 533/535 [M + H]⁺ |
| 78 | CH₃ | 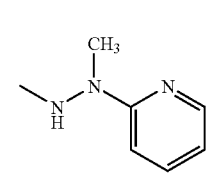 | viscidity MS (APCI): 436/438 [M + H]⁺ |
| 79 | CH₃— | 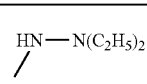 | solid MS (APCI): 468/470 [M + H]⁺ |
| (No. 6) | | | |
| 80 | CH₃— | HN—N(C₂H₅)₂ | powder MS (APCI): 433/435 [M + H]⁺ |

TABLE 2-continued

| | | | |
|---|---|---|---|
| 81 | CH$_3$— | 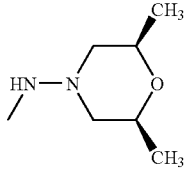 | powder MS (APCI): 475/477 [M + H]$^+$ |
| 82 | CH$_3$— | 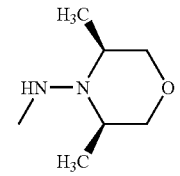 | powder MS (APCI): 473/475 [M + H]$^+$ |
| 83 | CH$_3$— | 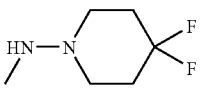 | powder MS (APCI): 481/483 [M + H]$^+$ |
| 84 | CH$_3$— |  | solid MS (APCI): 513/515 [M + H]$^+$ |
| 85 | C$_2$H$_5$— | 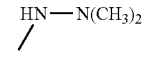 | solid MS (APCI): 419/421 [M + H]$^+$ |
| 86 | C$_2$H$_5$— | 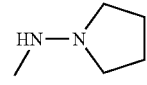 | solid MS (APCI): 445/447 [M + H]$^+$ |
| 87 | C$_2$H$_5$— | 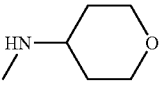 | solid MS (APCI): 460/462 [M + H]$^+$ |

(No. 7)

| | | | |
|---|---|---|---|
| 88 | CH$_3$O(CH$_2$)$_2$— | 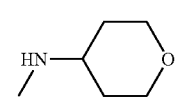 | solid MS (APCI): 490/492 [M + H]$^+$ |
| 89 | CH$_3$O(CH$_2$)$_2$— | 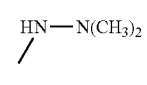 | powder MS (APCI): 449/451 [M + H]$^+$ |
| 90 | CH$_3$O(CH$_2$)$_2$— | 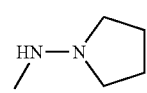 | powder MS (APCI): 475/477 [M + H]$^+$ |
| 91 | CH$_3$— | 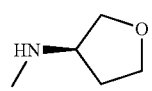 | solid MS (APCI): 432/434 [M + H]$^+$ |
| 92 | CH$_3$(CH$_2$)$_2$— | 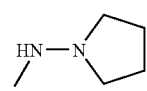 | solid MS (APCI): 459/461 [M + H]$^+$ |
| 93 | CH$_3$(CH$_2$)$_2$— | 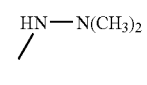 | solid MS (APCI): 433/435 [M + H]$^+$ |
| 94 | CH$_3$(CH$_2$)$_2$— | 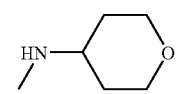 | solid MS (APCI): 474/476 [M + H]$^+$ |

TABLE 2-continued

| # | R | Structure | Properties |
|---|---|---|---|
| 95 | CH₃— | HN-N(piperazine)-N-phenyl | solid MS (APCI): 522/524 [M + H]⁺ |
| 96 | CH₃— | HN-N(piperazine)-N-(2-pyridyl) | solid MS (APCI): 523/525 [M + H]⁺ |

(No. 8)

| # | R | Structure | Properties |
|---|---|---|---|
| 97 | CH₃— | HN-N(pyrrolidine)-CH₂OCH₃ | solid MS (APCI): 475/477 [M + H]⁺ |
| 98 | CH₃— | HN-N(pyrrolidine)-CH₂OCH₃ | solid MS (APCI): 475/477 [M + H]⁺ |
| 99 | CH₃— | HN-N(piperazine)-N-(2-pyrimidinyl) | solid MS (APCI): 524/526 [M + H]⁺ |
| 100 | CH₃— | HN-N(piperazine)-N-(pyrazinyl) | solid MS (APCI): 524/526 [M + H]⁺ |
| 101 | CH₃(CH₂)₂— | HN-N(piperazine)-N-SO₂-phenyl | solid MS (APCI): 586/588 [M + H]⁺ |
| 102 | F₂CH— | HN-N(pyrrolidine) | solid MS (APCI): 467/469 [M + H]⁺ |
| 103 | F₂CH— | HN—N(CH₃)₂ | solid MS (APCI): 441/443 [M + H]⁺ |
| 104 | CH₃OCOCH₂— | HN—N(CH₃)₂ | solid MS (APCI): 463/465 [M + H]⁺ |
| 105 | F₂CH— | HN-(tetrahydropyran-4-yl) | solid MS (APCI): 482/484 [M + H]⁺ |

(No. 9)

| # | R | Structure | Properties |
|---|---|---|---|
| 106 | (CH₃)₂NSO₂— | HN-N(pyrrolidine) | solid MS (APCI): 524/526 [M + H]⁺ |
| 107 | (CH₃)₂NSO₂— | HN—N(CH₃)₂ | solid MS (APCI): 498/500 [M + H]⁺ |

TABLE 2-continued

| # | R | Amine | Properties |
|---|---|---|---|
| 108 | (CH₃)₂NSO₂— | HN-(4-tetrahydropyranyl)-N(CH₃) | solid MS (APCI): 539/541 [M + H]⁺ |
| 109 | CH₃— | HN-N(piperazinyl)-(2-fluorophenyl), N-CH₃ | solid MS (APCI): 540/542 [M + H]⁺ |
| 110 | CH₃— | HN-N(piperazinyl)-(4-fluorophenyl), N-CH₃ | solid MS (APCI): 540/542 [M + H]⁺ |
| 111 | CH₃— | HN-N(pyrrolidinyl-3-CF₃), N-CH₃ | solid MS (APCI): 499/501 [M + H]⁺ |
| 112 | 4-ethylthiazol-2-yl | HN-N(pyrrolidinyl), N-CH₃ | solid MS (APCI): 514/516 [M + H]⁺ |
| 113 | 4-ethylthiazol-2-yl | HN—N(CH₃)₂, N-CH₃ | solid MS (APCI): 488/490 [M + H]⁺ |
| 114 | 4-ethylthiazol-2-yl | HN-(4-tetrahydropyranyl)-N-CH₃ | solid MS (APCI): 529/531 [M + H]⁺ |

(No. 10)

| # | R | Amine | Properties |
|---|---|---|---|
| 115 | 3,5-dimethyl-4-ethylisoxazol-yl | HN-N(pyrrolidinyl), N-CH₃ | solid MS (APCI): 526/528 [M + H]⁺ |
| 116 | 3-ethyl-5-methylisoxazol-4-yl | HN-(4-tetrahydropyranyl)-N-CH₃ | solid MS (APCI): 527/529 [M + H]⁺ |
| 117 | 3,5-dimethyl-4-ethylisoxazol-yl | HN—N(CH₃)₂, N-CH₃ | solid MS (APCI): 500/502 [M + H]⁺ |
| 118 | CH₃— | HN-(pyridin-3-yl), N-CH₃ | solid MS (APCI): 439/441 [M + H]⁺ |
| 119 | CH₃— | HN-(pyridin-4-yl), N-CH₃ | solid MS (APCI): 439/441 [M + H]⁺ |

TABLE 2-continued

| 120 | CH₃— | 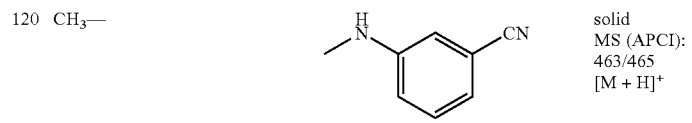 | solid<br>MS (APCI):<br>463/465<br>[M + H]⁺ |
| --- | --- | --- | --- |
| 121 | CH₃— | 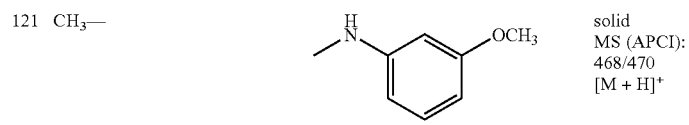 | solid<br>MS (APCI):<br>468/470<br>[M + H]⁺ |

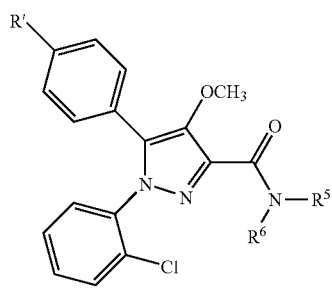

| Ex.<br>Nos. | R' | —N(R⁵)(R⁶) | Physicochemical<br>properties etc. |
| --- | --- | --- | --- |

(No. 11)

| 122 | F | 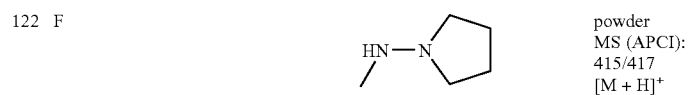 | powder<br>MS (APCI):<br>415/417<br>[M + H]⁺ |
| --- | --- | --- | --- |
| 123 | F | 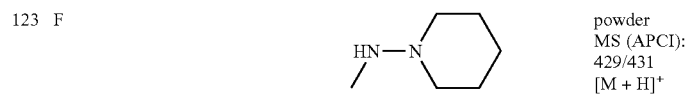 | powder<br>MS (APCI):<br>429/431<br>[M + H]⁺ |
| 124 | CH₃O— | 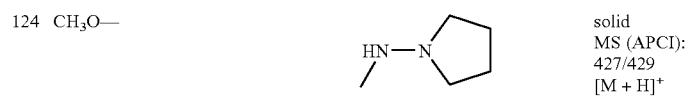 | solid<br>MS (APCI):<br>427/429<br>[M + H]⁺ |
| 125 | CH₃O— | 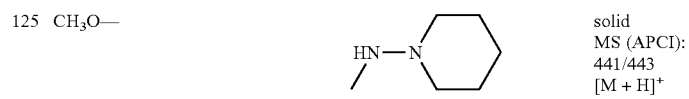 | solid<br>MS (APCI):<br>441/443<br>[M + H]⁺ |
| 126 | CH₃O— | 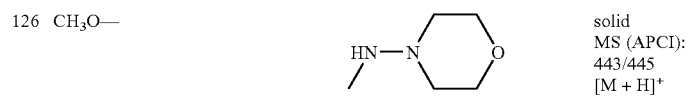 | solid<br>MS (APCI):<br>443/445<br>[M + H]⁺ |
| 127 | CH₃O— | 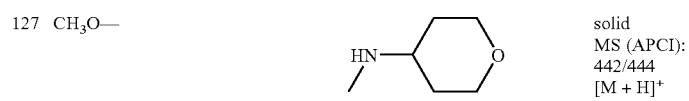 | solid<br>MS (APCI):<br>442/444<br>[M + H]⁺ |
| 128 | NC— | 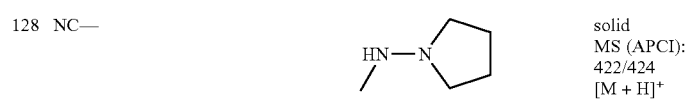 | solid<br>MS (APCI):<br>422/424<br>[M + H]⁺ |

TABLE 2-continued

[Structure: 5-(4-chlorophenyl)-1-(2-chloro-4-fluorophenyl)-4-methoxy-1H-pyrazole-3-carboxamide with N(R⁵)(R⁶)]

| Ex. Nos. | —N(R⁵)(R⁶) | Physicochemical properties etc. |
|---|---|---|
| (No. 12) | | |
| 129 | HN—N(CH₃)₂ | powder MS (APCI): 423/425 [M + H]⁺ |
| 130 | HN—N(pyrrolidine) | powder MS (APCI): 449/451 [M + H]⁺ |
| 131 | HN—N(piperidine) | powder MS (APCI): 463/465 [M + H]⁺ |
| 132 | HN—N(morpholine) | powder MS (APCI): 465/467 [M + H]⁺ |
| 133 | HN—(tetrahydropyran-4-yl) | powder MS (APCI): 464/466 [M + H]⁺ |

[Structure: 5-(4-trifluoromethylphenyl)-1-(2-chlorophenyl)-4-OR³-1H-pyrazole-3-carboxamide with N(R⁵)(R⁶)]

| Ex. Nos. | R³ | —N(R⁵)(R⁶) | Physicochemical properties etc. |
|---|---|---|---|
| (No. 13) | | | |
| 134 | CH₃— | HN—N(CH₃)₂ | solid MS (APCI): 439/441 [M + H]⁺ |
| 135 | CH₃— | HN—N(pyrrolidine) | solid MS (APCI): 465/467 [M + H]⁺ |
| 136 | CH₃— | HN—N(piperidine) | solid MS (APCI): 479/481 [M + H]⁺ |

TABLE 2-continued

| # | R | Amine | Form / MS |
|---|---|---|---|
| 137 | CH$_3$— | HN—N(morpholine, via N) | solid<br>MS (APCI): 481/483<br>[M + H]$^+$ |
| 138 | CH$_3$— | HN—(tetrahydropyran-4-yl) | solid<br>MS (APCI): 480/482<br>[M + H]$^+$ |
| 139 | F$_2$CH— | HN—N(CH$_3$)$_2$ | powder<br>MS (APCI): 475/477<br>[M + H]$^+$ |
| 140 | F$_2$CH— | HN—(tetrahydropyran-4-yl) | powder<br>MS (APCI): 516/518<br>[M + H]$^+$ |
| 141 | F$_2$CH— | HN—N(pyrrolidine) | powder<br>MS (APCI): 501/503<br>[M + H]$^+$ |
| 142 | C$_2$H$_5$— | HN—N(CH$_3$)$_2$ | solid<br>MS (APCI): 453/455<br>[M + H]$^+$ |

(No. 14)

| # | R | Amine | Form / MS |
|---|---|---|---|
| 143 | C$_2$H$_5$— | HN—N(pyrrolidine) | solid<br>MS (APCI): 479/481<br>[M + H]$^+$ |
| 144 | C$_2$H$_5$— | HN—N(piperidine) | solid<br>MS (APCI): 493/495<br>[M + H]$^+$ |
| 145 | C$_2$H$_5$— | HN—N(morpholine) | solid<br>MS (APCI): 495/497<br>[M + H]$^+$ |
| 146 | C$_2$H$_5$— | HN—(tetrahydropyran-4-yl) | solid<br>MS (APCI): 494/496<br>[M + H]$^+$ |
| 147 | CH$_3$O(CH$_2$)$_2$— | HN—N(CH$_3$)$_2$ | powder<br>MS (APCI): 483/485<br>[M + H]$^+$ |
| 148 | CH$_3$O(CH$_2$)$_2$— | HN—N(pyrrolidine) | solid<br>MS (APCI): 509/511<br>[M + H]$^+$ |
| 149 | CH$_3$O(CH$_2$)$_2$— | HN—N(piperidine) | solid<br>MS (APCI): 523/525<br>[M + H]$^+$ |
| 150 | CH$_3$O(CH$_2$)$_2$— | HN—N(morpholine) | solid<br>MS (APCI): 525/527<br>[M + H]$^+$ |

TABLE 2-continued
| 151 | CH₃O(CH₂)₂— | 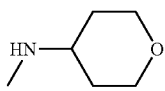 | powder MS (APCI): 524/526 [M + H]⁺ |
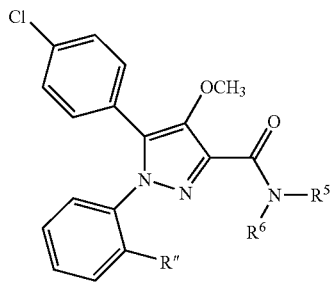
| Ex. Nos. | R″ | —N(R⁵)(R⁶) | Physicochemical properties etc. |
(No. 15)
| 152 | CF₃— | 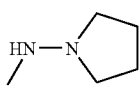 | solid MS (APCI): 465/467 [M + H]⁺ |
| 153 | CF₃— | 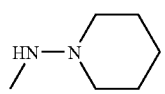 | solid MS (APCI): 479/481 [M + H]⁺ |
| 154 | CF₃— | 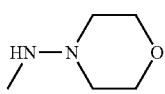 | solid MS (APCI): 481/483 [M + H]⁺ |
| 155 | CF₃— | 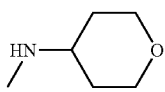 | solid MS (APCI): 480/482 [M + H]⁺ |
| 156 | NC— | 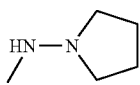 | powder MS (ESI): 422.10 [M + H]⁺ |
| 157 | F | HN—N(CH₃)₂ | powder MS (ESI): 389.09 [M + H]⁺ |
| 158 | F | 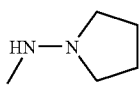 | powder MS (ESI): 415.11 [M + H]⁺ |
| 159 | F | 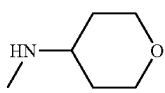 | powder MS (ESI): 430.10 [M + H]⁺ |

TABLE 2-continued
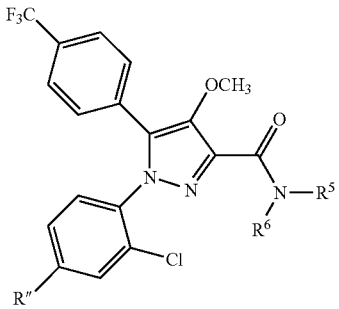
| Ex. Nos. | R" | —N(R⁵)(R⁶) | Physicochemical properties etc. |
|---|---|---|---|
| | | (No. 16) | |
| 160 | Cl | 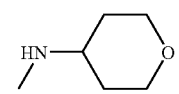 | powder MS (APCI): 514/516 [M + H]⁺ |
| 161 | Cl | HN—N(CH₃)₂ | powder MS (APCI): 473/475 [M + H]⁺ |
| 162 | Cl | 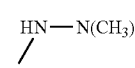 | powder MS (APCI): 515/517 [M + H]⁺ |
| 163 | Cl | 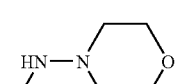 | powder MS (APCI): 548/550 [M + H]⁺ |
| 164 | Cl | 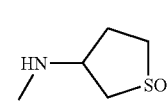 | powder MS (APCI): 536/538 [M + H]⁺ |
| 165 | F | 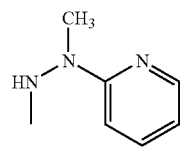 | powder MS (APCI): 498/500 [M + H]⁺ |
| 166 | F | HN—N(CH₃)₂ | powder MS (APCI): 457/459 [M + H]⁺ |
| 167 | F | 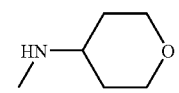 | powder MS (APCI): 499/501 [M + H]⁺ |
| 168 | F | 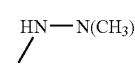 | powder MS (APCI): 532/534 [M + H]⁺ |
| 169 | F | 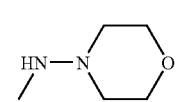 | powder MS (APCI): 520/522 [M + H]⁺ |

TABLE 2-continued

[Structure: pyrazole with 4-chlorophenyl, OR³, 2-chlorophenyl substituents, and C(O)N(R⁵)(R⁶) group]

| Ex. Nos. | R³ | —N(R⁵)(R⁶) | Physicochemical properties etc. |
|---|---|---|---|
| (No. 17) | | | |
| 170 | tetrahydropyran-4-yl | HN-(tetrahydropyran-4-yl) with methyl | powder MS (APCI): 516/518 [M + H]⁺ |
| 171 | CH₃ | HN—N(thiomorpholine-S-oxide) with methyl | powder MS (APCI): 479/481 [M + H]⁺ |
| 172 | tetrahydrothiopyran-4-yl | HN-(tetrahydropyran-4-yl) with methyl | powder MS (APCI): 532/534 [M + H]⁺ |
| 173 | CH₃ | 2,6-dimethyl-4-methylmorpholin-4-yl | powder MS (APCI): 460/462 [M + H]⁺ |
| 174 | CH₃ | 4,4-difluoropiperidin-1-yl | solid MS (APCI): 466/468 [M + H]⁺ |

[Structure: pyrazole with 4-R'-phenyl, OCH₃, and 2-chloro-4-R''-phenyl substituents, and C(O)N(R⁵)(R⁶) group]

| Ex. Nos. | R' | R'' | —N(R⁵)(R⁶) | Physicochemical properties etc. |
|---|---|---|---|---|
| (No. 18) | | | | |
| 175 | F | H | —NH—N(CH₃)₂ | powder MS (APCI): 389/391 [M + H]⁺ |
| 176 | F | H | HN—N(morpholin-4-yl) with methyl | powder MS (APCI): 431/433 [M + H]⁺ |

TABLE 2-continued

| Ex. No. | R' | R'' | —N(R⁵)(R⁶) | Physicochemical properties etc. |
|---|---|---|---|---|
| 177 | F | H | HN—[tetrahydropyran-4-yl] | powder MS (APCI): 430/432 [M + H]⁺ |
| 178 | CH₃O | H | —NH—N(CH₃)₂ | solid MS (APCI): 401/403 [M + H]⁺ |
| 179 | CH₃SO₂ | H | —NH—N(CH₃)₂ | solid MS (APCI): 449/451 [M + H]⁺ |
| 180 | CH₃SO₂ | H | HN—[pyrrolidin-1-yl] | solid MS (APCI): 475/477 [M + H]⁺ |
| 181 | CH₃SO₂ | H | HN—[tetrahydropyran-4-yl] | solid MS (APCI): 490/492 [M + H]⁺ |
| 182 | CN | H | —NH—N(CH₃)₂ | solid MS (APCI): 396/398 [M + H]⁺ |
| 183 | CN | H | HN—[tetrahydropyran-4-yl] | solid MS (APCI): 437/439 [M + H]⁺ |
| 184 | Cl | Cl | HN—[4-(CF₃)phenyl] | solid MS (APCI): 540/542 [M + H]⁺ |

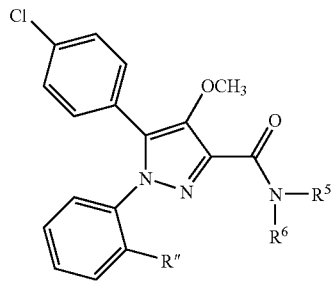

| Ex. Nos. | R'' | —N(R⁵)(R⁶) | Physicochemical properties etc. |
|---|---|---|---|
| (No. 19) | | | |
| 185 | CF₃ | —NH—N(CH₃)₂ | solid MS (APCI): 439/441 [M + H]⁺ |
| 186 | CH₃O | —NH—N(CH₃)₂ | powder MS (ESI): 401.09 [M + H]⁺ |
| 187 | CH₃O | HN—[pyrrolidin-1-yl] | powder MS (ESI): 427.13 [M + H]⁺ |
| 188 | CH₃O | HN—[tetrahydropyran-4-yl] | powder MS (ESI): 442.12 [M + H]⁺ |

TABLE 2-continued

| Ex. Nos. | —N(R⁵)(R⁶) | Physicochemical properties etc. |
|---|---|---|
| 189 CN | —NH—N(CH₃)₂ | powder MS (ESI): 396.09 [M + H]⁺ |
| 190 CN | 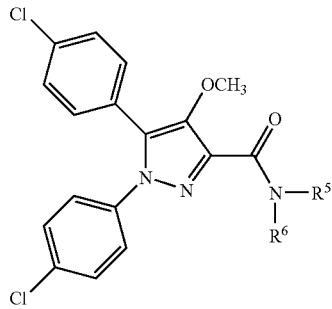 | powder MS (ESI): 437.10 [M + H]⁺ |

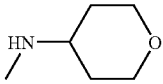

| Ex. Nos. | —N(R⁵)(R⁶) | Physicochemical properties etc. |
|---|---|---|
| (No. 20) | | |
| 191 | —NH—N(CH₃)₂ | powder MS (ESI): 405.03 [M + H]⁺ |
| 192 | 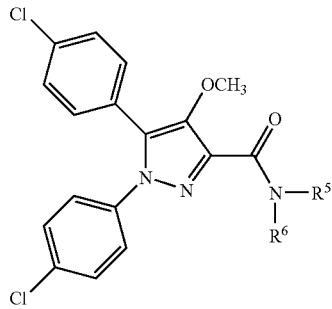 | powder MS (ESI): 446.04 [M + H]⁺ |

Examples 193 to 218

The corresponding starting materials were treated in the same manner as described in Example 22(3) to obtain the compounds as shown in the following Table 3.

TABLE 3

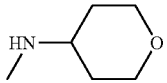

| Ex. Nos. | R''' | Physicochemical properties etc. |
|---|---|---|
| (No. 1) | | |
| 193 | 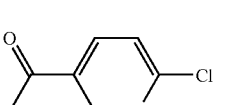 (4-F-phenyl carbonyl) | solid MS (APCI): 568/570 [M + H]⁺ |
| 194 | 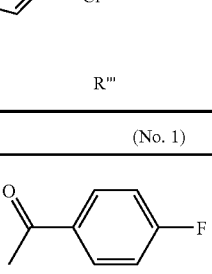 (6-CN-pyridin-3-yl carbonyl) | solid MS (APCI): 576/578 [M + H]⁺ |
| 195 | 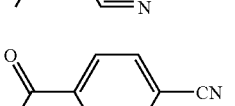 (6-Cl-pyridin-3-yl carbonyl) | solid MS (APCI): 585/587 [M + H]⁺ |
| 196 | 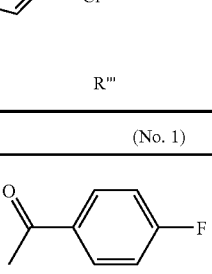 (4-CN-phenyl carbonyl) | solid MS (APCI): 575/577 [M + H]⁺ |
| 197 | 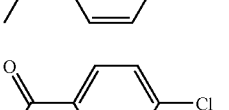 (4-Cl-phenyl carbonyl) | solid MS (ESI): 583.99 [M + H]⁺ |
| 198 | —COCH₃ | solid MS (ESI): 487.97 [M + H]⁺ |
| 199 | 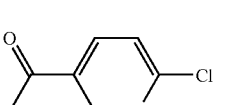 (4-CF₃-phenyl carbonyl) | solid MS (ESI): 618.03 [M + H]⁺ |

TABLE 3-continued

| | | | | |
|---|---|---|---|---|
| 200 | | 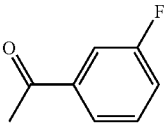 | | powder MS (ESI): 568.01 [M + H]$^+$ |
| 201 | | 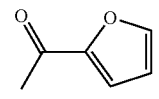 | | powder MS (ESI): 539.98 [M + H]$^+$ |
| 202 | | 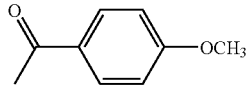 | | powder MS (ESI): 580.05 [M + H]$^+$ |

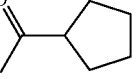

| Ex. Nos. | R' | R$^3$ | R''' | Physicochemical properties etc. |
|---|---|---|---|---|
| (No. 2) | | | | |
| 203 | Cl | CH$_3$ | 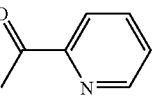 | powder MS (ESI): 524.04 [M + H]$^+$ |
| 204 | Cl | CH$_3$ | 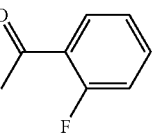 | powder MS (ESI): 551.00 [M + H]$^+$ |
| 205 | Cl | CH$_3$ | 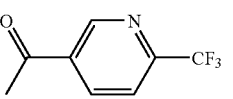 | solid MS (ESI): 568.01 [M + H]$^+$ |
| 206 | Cl | CH$_3$ | 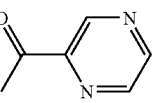 | solid MS (ESI): 618.99 [M + H]$^+$ |
| 207 | Cl | CH$_3$ | 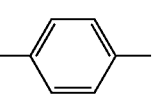 | solid MS (ESI): 552.01 [M + H]$^+$ |
| 208 | Cl | C$_2$H$_5$ | 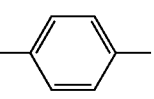 | solid MS (APCI): 582/584 [M + H]$^+$ |
| 209 | CF$_3$ | C$_2$H$_5$ | 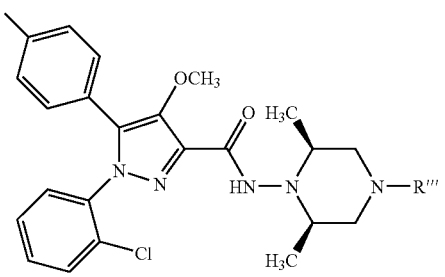 | solid MS (APCI): 616/618 [M + H]$^+$ |

TABLE 3-continued

| Ex. Nos. | R''' | Physicochemical properties etc. |
|---|---|---|
| (No. 3) | | |
| 210 | 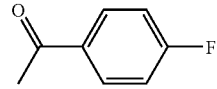 | solid MS (APCI): 578/580 [M + H]$^+$ |
| 211 | 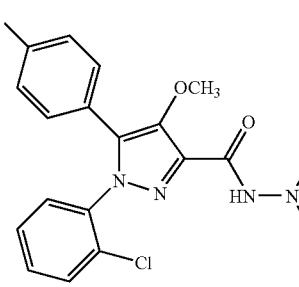 | solid MS (APCI): 596/598 [M + H]$^+$ |

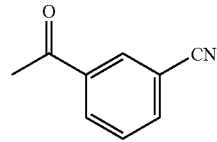

| Ex. Nos. | R''' | Physicochemical properties etc. |
|---|---|---|
| (No. 4) | | |
| 212 | 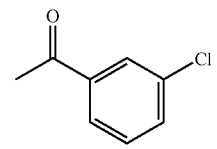 | solid MS (APCI): 575/577 [M + H]$^+$ |
| 213 | 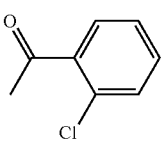 | solid MS (APCI): 584/586 [M + H]$^+$ |
| 214 | 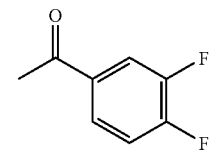 | solid MS (APCI): 584/586 [M + H]$^+$ |
| 215 | | solid MS (APCI): 586/588 [M + H]$^+$ |

TABLE 3-continued

| | | |
|---|---|---|
| 216 | [structure: acetyl-2,4-difluorophenyl] | solid<br>MS (APCI):<br>586/588<br>[M + H]⁺ |
| 217 | [structure: acetyl-3,5-difluorophenyl] | solid<br>MS (APCI):<br>586/588<br>[M + H]⁺ |
| 218 | [structure: acetyl-2-cyanophenyl] | solid<br>MS (APCI):<br>575/577<br>[M + H]⁺ |

Examples 219 to 224

The corresponding starting materials were treated in the same manner as described in Example 1 or 22(3) to obtain the compounds as shown in the following Table 4.

TABLE 4

[Core structure: 1-(2-chlorophenyl)-5-(4-chlorophenyl)-4-methoxy-pyrazole-3-carboxamide with HN—R⁶]

| Ex. Nos. | R⁶ | Physicochemical properties etc. |
|---|---|---|
| 219 | [4-methylpiperidinyl-benzoyl] | solid<br>MS (APCI):<br>549/551<br>[M + H]⁺ |
| 220 | [4-methylpiperidinyl-(4-fluorobenzoyl)] | solid<br>MS (APCI):<br>567/569<br>[M + H]⁺ |
| 221 | [3-methylpyrrolidinyl-benzoyl] | powder<br>MS (APCI):<br>535/537<br>[M + H]⁺ |

TABLE 4-continued

[Core structure: 1-(2-chlorophenyl)-5-(4-chlorophenyl)-4-methoxy-pyrazole-3-carboxamide with HN—R⁶]

| Ex. Nos. | R⁶ | Physicochemical properties etc. |
|---|---|---|
| 222 | [3-methylpyrrolidinyl-(3-fluorobenzoyl)] | powder<br>MS (APCI):<br>553/555<br>[M + H]⁺ |
| 223 | [3-methylpyrrolidinyl-(4-fluorobenzoyl)] | powder<br>MS (APCI):<br>553/555<br>[M + H]⁺ |
| 224 | [3-methylpyrrolidinyl-(4-chlorobenzoyl)] | powder<br>MS (APCI):<br>569/571<br>[M + H]⁺ |

Examples 225 to 231

The corresponding starting materials were treated in the same manner as described in Example 28 to obtain the compounds as shown in the following Table 5.

TABLE 5

[Core structure: 1-(2-chlorophenyl)-5-(4-chlorophenyl)-4-methoxy-3-(1,3,4-oxadiazol-2-yl)pyrazole with R''']

| Ex. Nos. | R''' | Physicochemical properties etc. |
|---|---|---|
| 225 | [cyclopentyl] | solid<br>MS (APCI):<br>455/457<br>[M + H]⁺ |

TABLE 5-continued

Structure: 5-(4-chlorophenyl)-1-(2-chlorophenyl)-4-methoxy-3-(5-R'''-1,3,4-oxadiazol-2-yl)-1H-pyrazole

| Ex. Nos. | R''' | Physicochemical properties etc. |
|---|---|---|
| 226 | —CH₂—CF₃ | solid<br>MS (APCI): 469/471 [M + H]⁺ |
| 227 | tetrahydropyran-4-yl | solid<br>MS (APCI): 471/473 [M + H]⁺ |
| 228 | 4-methyl-1-benzoylpiperidin-4-yl | solid<br>MS (APCI): 574/576 [M + H]⁺ |
| 229 | 4-methyl-1-(pyrimidin-2-yl)piperidin-4-yl | solid<br>MS (APCI): 548/550 [M + H]⁺ |
| 230 | 4-cyanophenyl-methyl (4-methylbenzonitrile) | solid<br>MS (APCI): 488/490 [M + H]⁺ |
| 231 | 4-methylphenyl | solid<br>MS (APCI): 463/465 [M + H]⁺ |

Examples 232 to 238

The corresponding starting materials were treated in the same manner as described in Example 19 to obtain the compounds as shown in the following Table 6.

TABLE 6

Structure: 5-(4-R'-phenyl)-1-(2-chloro-4-R''-phenyl)-4-methoxy-N-(1-R'''-azetidin-3-yl)-1H-pyrazole-3-carboxamide

| Ex. Nos. | R' | R'' | R''' | Physicochemical properties etc. |
|---|---|---|---|---|
| 232 | Cl | Cl | benzoyl | powder<br>MS(APCI): 555/557 [M + H]⁺ |
| 233 | Cl | Cl | 3-fluorobenzoyl | powder<br>MS(APCI): 573/575 [M + H]⁺ |
| 234 | Cl | Cl | 4-fluorobenzoyl | powder<br>MS(APCI): 573/575 [M + H]⁺ |
| 235 | CF₃ | H | benzoyl | powder<br>MS(APCI): 555/557 [M + H]⁺ |
| 236 | CF₃ | H | 3-fluorobenzoyl | powder<br>MS(APCI): 573/575 [M + H]⁺ |
| 237 | CF₃ | H | 4-fluorobenzoyl | powder<br>MS(APCI): 573/575 [M + H]⁺ |
| 238 | CF₃ | H | 4-chlorobenzoyl | powder<br>MS(APCI): 589/591 [M + H]⁺ |

Examples 239 to 248

The corresponding starting materials were treated in the same manner as described in Example 23 to obtain the compounds as shown in the following Table 7.

TABLE 7

| Ex. Nos. | R' | R" | R³ | Physicochemical properties etc. |
|---|---|---|---|---|
| 239 | Cl | H | —C₂H₅ | solid MS(APCI): 509/511 [M + H]⁺ |
| 240 | Cl | H | —(CH₂)₂OCH₃ | solid MS(APCI): 539/541 [M + H]⁺ |
| 241 | Cl | H | —CHF₂ | solid MS(APCI): 531/533 [M + H]⁺ |
| 242 | Cl | Cl | —CH₃ | solid MS(APCI): 529/531 [M + H]⁺ |
| 243 | CF₃ | H | —C₂H₅ | solid MS(APCI): 543/545 [M + H]⁺ |
| 244 | CF₃ | H | —(CH₂)₂OCH₃ | solid MS(APCI): 573/575 [M + H]⁺ |
| 245 | Cl | Cl | —CH₂—CF₃ | powder MS(APCI): 597/599 [M + H]⁺ |
| 246 | CF₃ | Cl | —CH₃ | powder MS(APCI): 563/565 [M + H]⁺ |
| 247 | CF₃ | F | —CH₃ | powder MS(APCI): 547/549 [M + H]⁺ |
| 248 | CF₃ | H | —CH₃ | powder MS(APCI): 529/531 [M + H]⁺ |

Examples 249 to 254

The corresponding starting materials were treated in the same manner as described in Example 30 to obtain the compounds as shown in the following Table 8.

TABLE 8

| Ex. Nos. | —N(R⁵)(R⁶) | Physicochemical properties etc. |
|---|---|---|
| 249 | CH₃—N(CH₃)—CH₂CH₂—OCH₃ | solid MS(APCI): 449/451 [M + H]⁺ |
| 250 | morpholino | solid MS(APCI): 447/449 [M + H]⁺ |

TABLE 8-continued

| Ex. Nos. | —N(R⁵)(R⁶) | Physicochemical properties etc. |
|---|---|---|
| 251 | piperidino | solid MS(APCI): 445/447 [M + H]⁺ |
| 252 | —N(CH₃)₂ | solid MS(APCI): 405/407 [M + H]⁺ |
| 253 | 1-methyl-4-(ethylamino)piperidine-4-carboxamide | solid MS(APCI): 531/533 [M + H]⁺ |
| 254 | thiomorpholine-1,1-dioxide | solid MS(APCI): 495/497 [M + H]⁺ |

Examples 255 to 260

The corresponding starting materials were treated in the same manner as described in Example 29 to obtain the compounds as shown in the following Table 9.

TABLE 9

| Ex. Nos. | R''' | Physicochemical properties etc. |
|---|---|---|
| 255 | phenyl | solid MS(APCI): 438/440 [M + H]⁺ |
| 256 | 4-cyanophenyl | solid MS(APCI): 463/465 [M + H]⁺ |

TABLE 9-continued

[Structure: 5-(4-chlorophenyl)-4-methoxy-1-(2-chlorophenyl)-1H-pyrazol-3-yl with NH-C(O)-R''']

| Ex. Nos. | R''' | Physicochemical properties etc. |
|---|---|---|
| 257 | 2-methylpyridin-5-yl | solid MS(APCI): 439/441 [M + H]+ |
| 258 | 2-cyano-4-methylpyridin-5-yl | solid MS(APCI): 464/466 [M + H]+ |
| 259 | 2-trifluoromethyl-4-methylpyridin-5-yl | solid MS(APCI): 507/509 [M + H]+ |
| 260 | 4-(methylsulfonyl)phenyl | solid MS(APCI): 516/518 [M + H]+ |

Examples 261 to 262

The corresponding starting materials were treated in the same manner as described in Example 37 to obtain the compounds as shown in the following Table 10.

TABLE 10

[Structure: 5-(4-chlorophenyl)-4-methoxy-1-(2-chlorophenyl)-1H-pyrazole-3-carboxamide with HN-N(R5)(R6)]

| Ex. Nos. | —N(R5)(R6) | Physicochemical properties etc. |
|---|---|---|
| 261 | 2-oxopyrrolidin-1-yl | solid MS(APCI): 445/447 [M + H]+ |
| 262 | N-methyl-N-(cyanoacetyl)amino | solid MS(APCI): 458/460 [M + H]+ |

Example 263

To a solution of the compound obtained in Example 64 (127 mg) in methylene chloride (2 mL) was added 3-chloroperbenzoic acid (90 mg, water content: 25%) at 0° C. and the mixture was stirred at the same temperature for 30 minutes. To the reaction mixture was added an aqueous sodium hydrogencarbonate solution and the mixture was stirred. The organic layer was separated and concentrated in vacuo. The resultant crude product was purified by column chromatography on silica gel (solvent: chloroform/methanol=100/0 to 95/5) to obtain 1-(2-chlorophenyl)-5-(4-chloro-phenyl)-4-[2-(methylsulfinyl)ethoxy]-3-[N-(1-pyrrolidinyl)carbamoyl]-1H-pyrazole (92 mg; yield: 70%) as a powder.

MS (APCI) m/z; 523/525 [M+H]+

Example 264

The compound obtained in Reference Example 9 (2) (33 mg) was treated in the same manner as described in Example 29 to obtain 1-(2-chlorophenyl)-5-(4-chloro-phenyl)-4-methoxy-3-[N-[(1-benzoylpiperidin-4-yl)carbonyl]amino]-1H-pyrazole (40 mg, yield: 74%) as a solid.

MS (APCI) m/z; 549/551 [M+H]+

Example 265

The compound obtained in Example 172 (160 mg) was treated in the same manner as described in Example 15 to obtain 1-(2-chlorophenyl)-5-(4-chloro-phenyl)-4-(1-oxo-4-tetrahydrothiopyranyl)oxy-3-[N-[(4-tetrahydropyranyl)carbamoyl]-1H-pyrazole (15 mg, yield: 10%) as a powder.

MS (APCI) m/z; 548/550 [M+H]+

Example 266

The compound obtained in Example 172 (160 mg) was treated in the same manner as described in Example 16 to obtain 1-(2-chlorophenyl)-5-(4-chlorophenyl)-4-(1,1-dioxo-4-tetrahydrothiopyranyl)oxy-3-[N-[(4-tetrahydropyranyl)carbamoyl]-1H-pyrazole (73 mg, yield: 45%) as a powder.

MS (APCI) m/z; 564/566 [M+H]+

Example 267

(1) The compound obtained in Reference Example 18 (155 mg) was treated in the same manner as described in Example 1 to obtain 1-(2-chlorophenyl)-5-(4-chloro-phenyl)-4-(4-tetrahydrothiopyranyl)oxy-3-[N-(morpholino)carbamoyl]-1H-pyrazole (170 mg, yield: 92%) as a powder.

MS (APCI) m/z; 533/535 [M+H]+

(2) The compound obtained in the above step (1) (152 mg) was treated in the same manner as described in Example 15 to obtain 1-(2-chlorophenyl)-5-(4-chloro-phenyl)-4-(1-oxo-4-tetrahydrothiopyranyl)oxy-3-[N-(morpholino)carbamoyl]-1H-pyrazole (97 mg, yield: 62%) as a powder.

MS (APCI) m/z; 549/551 [M+H]+

Example 268

The compound obtained in Example 78 (65 mg) was treated in the same manner as described in Example 15 to obtain 1-(2-chlorophenyl)-5-(4-chlorophenyl)-4-methoxy-3-[N-[2-(methylsulfinyl)ethyl]carbamoyl]-1H-pyrazole (62 mg, yield: 92%) as a powder.

MS (APCI) m/z; 452/454 [M+H]+

Example 269

The compound obtained in Example 78 (65 mg) was treated in the same manner as described in Example 16 to obtain 1-(2-chlorophenyl)-5-(4-chlorophenyl)-4-methoxy-3-[N-[2-(methylsulfonyl)ethyl]carbamoyl]-1H-pyrazole (68 mg, yield: 96%) as a powder.

MS (APCI) m/z; 468/470 [M+H]$^+$

Example 270

The corresponding starting materials were treated in the same manner as described in Example 29 to obtain 1-(2-chlorophenyl)-5-(4-chlorophenyl)-4-methoxy-3-[N-(2-pyridylacetyl)amino]-1H-pyrazole (31 mg, yield: 69%) as a powder.

MS (APCI) m/z; 453/455 [M+H]$^+$

Example 271

The corresponding starting materials were treated in the same manner as described in Example 27 to obtain 4-(carbamoyl)methoxy-1-(2-chlorophenyl)-5-(4-chlorophenyl)-3-[N',N'-dimethylhydrazino)carbonyl]-1H-pyrazole (26.7 mg, yield: 30%) as a powder.

MS (APCI) m/z; 448/451 [M+H]$^+$

Examples 272 to 273

The corresponding starting materials were treated in the same manner as described in Example 1 and then Reference Example 14 to obtain the compounds as shown in the following Table 11.

TABLE 11

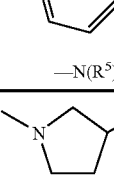

| Ex. Nos. | —N(R$^5$)(R$^6$) | Physicochemical properties etc. |
|---|---|---|
| 272 | 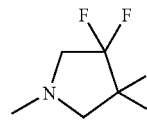 | powder<br>MS(APCI): 509/511 [M + H]$^+$ |
| 273 | | solid<br>MS(APCI): 503/505 [M + H]$^+$ |

Example 274

(1) The compound obtained in Reference Example 1(6) (109 mg) and the compound obtained in Reference Example 48 (105 mg) were treated in the same manner as described in Example 1 to obtain 1-(2-chlorophenyl)-5-(4-chlorophenyl)-4-methoxy-3-[N-(4-benzyl-4-ethoxycarbonylpiperidin-1-yl)carbamoyl]-1H-pyrazole (152 mg, Yield: 83%) as a colorless solid.

MS (APCI) m/z; 607/609 [M+H]$^+$ (2) To a solution of the compound obtained in the above step (1) (150 mg) in ethanol (3 mL) was added an aqueous 2N sodium hydroxide solution (250 μL) and the mixture was stirred at 60° C. overnight. To the reaction mixture was added an aqueous 2N sodium hydroxide solution (500 μL) and the mixture was stirred at 90° C. for 2 days. After cooling to room temperature, to the reaction mixture was added an aqueous 1N HCl solution and the mixture was stirred and extracted with chloroform. The extract was concentrated in vacuo and the resultant crude product was purified by column chromatography on silica gel (solvent: chloroform/methanol=98/2 to 95/5) and thin layer chromatography on silica gel (solvent; chloroform/methanol=95/5) to obtain 1-(2-chlorophenyl)-5-(4-chlorophenyl)-4-methoxy-3-[N-(4-benzyl-4-carboxypiperidin-1-yl)carbamoyl]-1H-pyrazole (55.5 mg, Yield: 38%) as a pale yellow solid.

MS (APCI) m/z; 579/581 [M+H]$^+$ (3) To a solution of the compound obtained in the above step (2) (29.4 mg) in dimethylformamide (1 mL) was added ammonium chloride (5.5 mg), water soluble carbodiimide hydrochloride (20 mg), 1-hydroxybenzotriazole hydrate (16 mg) and triethylamine (20 μL) and the mixture was stirred at room temperature overnight. To the reaction mixture was added an aqueous sodium hydrogencarbonate solution and the mixture was stirred and extracted with chloroform. The organic layer was washed with water and concentrated in vacuo. The resultant crude product was purified by column chromatography on NH-silica gel (Chromatorex NH-silica gel, solvent: hexane/ethyl acetate=35/65 to 0/100) to obtain 1-(2-chlorophenyl)-5-(4-chlorophenyl)-4-methoxy-3-[N-(4-benzyl-4-carbamoylpiperidin-1-yl)carbamoyl]-1H-pyrazole (23.6 mg, Yield: 80%) as a colorless solid.

MS (APCI) m/z; 578/580 [M+H]$^+$

Example 275

(1) The compound obtained in Reference Example 1(6) (545 mg) and the compound obtained in Reference Example 45(3) (292 mg) were treated in the same manner as described in Example 1 to obtain 1-(2-chlorophenyl)-5-(4-chlorophenyl)-4-methoxy-3-[N-(4-methoxycarbonyl-tetrahydrothiopyran-4-yl)carbamoyl]-1H-pyrazole (480 mg, Yield: 92%) as a colorless solid.

MS (APCI) m/z; 520/522 [M+H]$^+$ (2) To a solution of the compound obtained in the above step (1) (275 mg) in methylene chloride (5 mL) was added trifluoroacetic acid (163 μL) under ice-cooling and the mixture was stirred at room temperature for 30 minutes. To the reaction mixture was added m-chloroperbenzoic acid (244 mg) under ice-cooling and the mixture was stirred at room temperature for 1 hour. To the reaction mixture was further added m-chloroperbenzoic acid (61 mg) and the mixture was stirred at room temperature for 30 minutes. The reaction mixture was extracted and purified in the same manner as described in Example 15 to obtain 1-(2-chlorophenyl)-5-(4-chlorophenyl)-4-methoxy-3-[N-(4-methoxycarbonyl-1,1-dioxo-tetrahydrothiopyran-4-yl)carbamoyl]-1H-pyrazole (272.1 mg, Yield: 93%) as a pale yellow solid.

MS (APCI) m/z; 552/554 [M+H]$^+$ (3) To a solution of the compound obtained in the above step (2) (270 mg) in ethanol (3 mL) was added an aqueous 2N sodium hydroxide solution (490 μL) and the mixture was stirred at room temperature overnight. To the reaction mixture was added an aqueous 2N HCl solution (500 μL) and the mixture was stirred and extracted with chloroform. The extract was concentrated in vacuo and the resultant crude product was purified by column chromatography on silica gel (solvent: chloroform/methanol=99/1 to 90/10) to obtain 1-(2-chlorophenyl)-5-(4-chlorophenyl)-4-methoxy-3-[N-(4-carboxy-1,1-dioxo-tetrahydrothiopyran-4-yl)carbamoyl]-1H-pyrazole (224.7 mg, Yield: 85%) as a pale yellow solid.

MS (APCI) m/z; 538/540 [M+H]$^+$ (4) To a solution of the compound obtained in the above step (3) (38 mg) in dimethylformamide (1 mL) was added ammonium chloride (7.5 mg), water soluble carbodiimide hydrochloride (28 mg), 1-hydroxybenzotriazole hydrate (21 mg) and triethylamine (29 μL) and the mixture was stirred at room temperature for 2 days. To the reaction mixture was added an aqueous sodium hydrogencarbonate solution and the mixture was stirred and extracted with chloroform. The organic layer was washed with water and concentrated in vacuo. The resultant crude product was purified by column chromatography on NH-silica gel (Chromatorex NH-silica gel, solvent: hexane/ethyl acetate=20/80 to 0/100) to obtain 1-(2-chlorophenyl)-5-(4-chlorophenyl)-4-methoxy-3-[N-(4-carbamoyl-1,1-dioxo-tetrahydrothiopyran-4-yl)carbamoyl]-1H-pyrazole (33.9 mg, Yield: 85%) as a colorless solid.

MS (APCI) m/z; 537/539 [M+H]$^+$

Example 276

(1) The compound obtained in Reference Example 5(2) (168 mg) and the compound obtained in Reference Example 47(2) (70 mg) were treated in the same manner as described in Example 1 to obtain 1-(2-chlorophenyl)-5-(4-chlorophenyl)-4-methoxycarbonylmethoxy-3-[N-(4-methoxycarbonyl-4-phenylpiperidin-1-yl)carbamoyl]-1H-pyrazole (108.1 mg, Yield: 57%) as a colorless solid.

MS (APCI) m/z; 637/639 [M+H]$^+$ (2) To a solution of the compound obtained in the above step (1) (107 mg) in ethanol (2 mL) was added an aqueous 2N sodium hydroxide solution (336 μL) and the mixture was stirred at 80° C. for 2 hours. To the reaction mixture was added an aqueous 2N sodium hydroxide solution (168 μL) and the mixture was stirred at 100° C. for 1 hour. To the reaction mixture was added tetrahydrofuran (1 mL) and the mixture was stirred at 100° C. for 3 days. After cooling to room temperature, to the reaction mixture was added an aqueous 2N HCl (500 μL) and the mixture was stirred and extracted with chloroform. The extract was concentrated in vacuo and the residue was diluted with dimethylformamide (2 mL). Thereto was added ammonium chloride (27 mg), water soluble carbodiimide hydrochloride (97 mg), 1-hydroxybenzotriazole hydrate (77 mg) and triethylamine (140 μL) and the mixture was stirred at room temperature for 4 hours. To the reaction mixture was added an aqueous sodium hydrogencarbonate solution and the mixture was stirred and extracted with chloroform. The organic layer was washed with water and concentrated in vacuo. The resultant crude product was purified by column chromatography on NH-silica gel (Chromatorex NH-silica gel, solvent: hexane/ethyl acetate=20/80 to 0/100) to obtain 1-(2-chlorophenyl)-5-(4-chloro-phenyl)-4-carbamoylmethoxy-3-[N-(4-carbamoyl-4-phenylpiperidin-1-yl)carbamoyl]-1H-pyrazole (59.2 mg, Yield: 58%) as a colorless solid.

MS (APCI) m/z; 607/609 [M+H]$^+$

Example 277

(1) To a solution of S-methylthiourea sulfate (15.31 g) and potassium carbonate (30.4 g) in water (300 mL) was added dropwise a solution of ditert-butyl dicarboxylate (21.82 g) in tetrahydrofuran (100 mL) under ice-cooling and the mixture was stirred at room temperature overnight. The reaction mixture was extracted with ethyl acetate and the extract was dried over magnesium sulfate and concentrated in vacuo to obtain N-tert-butoxycarbonyl-5-methylthiourea (18.85 g, Yield: 99%) as a white solid.

MS (APCI) m/z; 191 [M+H]$^+$ (2) To a solution of the compound obtained in Reference Example 1(6) (3.63 g), the compound obtained in the above step (1) (2.85 g), 1-hydroxybenzotriazole (2.28 g) and triethylamine (1.51 g) in N,N-dimethylformamide (100 mL) was added water-soluble carbodiimide hydrochloride (2.86 g) at room temperature and the mixture was stirred overnight. To the reaction mixture was added water and the resultant precipitates were collected by filtration and dissolved in chloroform. The solution was washed with water, dried over magnesium sulfate and concentrated in vacuo to obtain 1-(2-chlorophenyl)-5-(4-chlorophenyl)-4-methoxy-3-[N-{(tert-butoxycarbonylamino) (methylthio) methylidene}carbamoyl]-1H-pyrazole (5.20 g, Yield: 97%) as a white solid.

MS (APCI) m/z; 535/537 [M+H]$^+$ (3) To a suspension of the compound obtained in the above step (2) (1.07 g) and potassium carbonate (6.91 g) in methanol (20 mL) was added hydrazine hydrochloride (6.85 g) at room temperature and the mixture was stirred at 80° C. overnight. After cooling, to the reaction mixture was added water and the mixture was extracted with chloroform. The extract was dried over magnesium sulfate and concentrated in vacuo. The resultant crude product was purified by column chromatography on silica gel (solvent: hexane/ethyl acetate=65/35 to 45/55) to obtain 1-(2-chlorophenyl)-5-(4-chlorophenyl)-4-methoxy-3-[5-(tert-butoxycarbonylamino)-1,2,4-triazol-3-yl]-1H-pyrazole (814 mg, Yield: 81%) as a white solid.

MS (APCI) m/z; 501/503 [M+H]$^+$ (4) To a solution of the compound obtained in the above step (3) (0.80 g) in methanol (10 mL) was added 4N HCl-dioxane (2.0 mL) at room temperature and the mixture was stirred overnight. To the reaction mixture was added an aqueous sodium hydrogencarbonate solution and the mixture was extracted with chloroform. The extract was dried over magnesium sulfate and concentrated in vacuo to obtain 1-(2-chlorophenyl)-5-(4-chlorophenyl)-4-methoxy-3-(5-amino-1,2,4-triazol-3-yl]-1H-pyrazole (390 mg, Yield: 61%) as a white solid.

MS (APCI) m/z; 401/403 [M+H]$^+$ (5) To a suspension of the compound obtained in the above step (4) (100 mg) and potassium carbonate (276 mg) in acetonitrile (3 mL) was added 1,4-dibromobutane (215 mg) at room temperature and the mixture was stirred at 140° C. in a microwave reactor for 90 minutes. To the reaction mixture was added water and the mixture was extracted with ethyl acetate. The extract was dried over magnesium sulfate and concentrated in vacuo. The resultant crude product was purified by column chromatography on silica gel (solvent: chloroform/methanol=100/0 to 92/8) to obtain 1-(2-chlorophenyl)-5-(4-chlorophenyl)-4-methoxy-3-[5-(1-pyrrolidinyl)-1,2,4-triazol-3-yl]-1H-pyrazole (33.4 mg, Yield: 29%) as a yellow solid.

MS (APCI) m/z; 455/457 [M+H]$^+$

Example 278

(1) To a suspension of the compound obtained in Example 277(2) (1.07 g) and potassium carbonate (6.91 g) in methanol (20 mL) was added hydroxylamine hydrochloride (6.95 g) at room temperature and the mixture was stirred at 80° C. overnight. After cooling, to the reaction mixture was added water and the mixture was extracted with chloroform. The extract was dried over magnesium sulfate and concentrated in vacuo. The resultant crude product was purified by column chromatography on silica gel (solvent: hexane/ethyl acetate=80/20 to 60/40) to obtain 1-(2-chlorophenyl)-5-(4-chlorophenyl)-4-methoxy-3-[3-(tert-butoxycarbonylamino)-1,2,4-oxadiazol-5-yl]-1HH-pyrazole (194 mg, Yield: 19%) as a white solid.

MS (APCI) m/z; 502/504 [M+H]$^+$ (2) To a solution of the compound obtained in the above step (1) (0.17 g) in methanol (5 mL) was added 4N HCl-dioxane (1.0 mL) at room temperature and the mixture was stirred overnight. To the reaction mixture was added an aqueous sodium hydrogencarbonate solution and the mixture was extracted with chloroform. The extract was dried over magnesium sulfate and concentrated in vacuo to obtain 1-(2-chlorophenyl)-5-(4-chlorophenyl)-4-methoxy-3-(3-amino-1,2,4-oxadiazol-5-yl)-1H-pyrazole (104 mg, Yield: 76%) as a white solid.

MS (APCI) m/z; 402/404 [M+H]$^+$ (3) To a suspension of the compound obtained in the above step (2) (80 mg) and potassium carbonate (276 mg) in acetonitrile (3 mL) was added 1,4-dibromobutane (1 mL) at room temperature and the mixture was stirred at 140° C. in a microwave reactor for 210 minutes. To the reaction mixture was added water and the mixture was extracted with ethyl acetate. The extract was dried over magnesium sulfate and concentrated in vacuo. The resultant crude product was purified by column chromatography on silica gel (solvent: hexane/ethyl acetate=95/5 to 0/100) to obtain 1-(2-chlorophenyl)-5-(4-chlorophenyl)-4-methoxy-3-[3-(1-pyrrolidinyl)-1,2,4-oxadiazol-5-yl]-1H-pyrazole (8.1 mg, Yield: 9%) as a white solid.

MS (APCI) m/z; 456/458 [M+H]$^+$

Example 279

(1) To a solution of the compound obtained in Reference Example 1(4) (3.77 g) in ethanol (30 mL) was added an aqueous 2N sodium hydroxide solution (10 mL) and the mixture was stirred at room temperature for 5 hours. To the reaction mixture was further added an aqueous 2N sodium hydroxide solution (5 mL) and the mixture was stirred at 60° C. overnight. After cooling to room temperature, to the reaction mixture was added an aqueous 2N HCl (20 mL) and the mixture was stirred. To the mixture was added water and the mixture was further stirred. The resultant precipitates were collected by filtration and dried to obtain 3-carboxy-1-(2-chlorophenyl)-5-(4-chlorophenyl)-4-hydroxy-1H-pyrazole (3.07 g, Yield: 88%) as a colorless solid.

MS (APCI) m/z; 349/351 [M+H]$^+$ (2) The compound obtained in the above step (1) (52 mg) and the compound obtained in Reference Example 53(3) (34 mg) were treated in the same manner as described in Example 1 to obtain 1-(2-chlorophenyl)-5-(4-chlorophenyl)-4-hydroxy-3-[[4-carbamoyl-4-(ethylamino)piperidino]carbonyl]-1H-pyrazole (33.7 mg, Yield: 45%) as a pale yellow solid.

MS (APCI) m/z; 502/504 [M+H]$^+$

Example 280

(1) The compound obtained in Reference Example 1(6) (145 mg) and the compound obtained in Reference Example 44 (77 mg) were treated in the same manner as described in Example 1 to obtain 1-(2-chlorophenyl)-5-(4-chlorophenyl)-4-methoxy-3-[N-(1-methoxycarbonylcyclohexan-1-yl)carbamoyl]-1H-pyrazole (175 mg, Yield: 87%) as a colorless powder.

MS (APCI) m/z; 502/504 [M+H]$^+$ (2) The compound obtained in the above step (1) (174 mg) were treated in the same manner as described in Example 275(3) to obtain 1-(2-chlorophenyl)-5-(4-chlorophenyl)-4-methoxy-3-[N-(1-carboxycyclohexan-1-yl)carbamoyl]-1H-pyrazole (171 mg, Yield: 100%) as a colorless solid.

MS (APCI) m/z; 488/490 [M+H]$^+$ (3) The compound obtained in the above step (2) (34 mg) were treated in the same manner as described in Example 275(4) to obtain 1-(2-chlorophenyl)-5-(4-chlorophenyl)-4-methoxy-3-[N-(1-carbamoylcyclohexan-1-yl)carbamoyl]-1H-pyrazole (26.1 mg, Yield: 77%) as a colorless solid.

MS (APCI) m/z; 487/489 [M+H]$^+$

Example 281

(1) The compound obtained in Reference Example 1(6) (145 mg) and the compound obtained in Reference Example 46 (78 mg) were treated in the same manner as described in Example 1 to obtain 1-(2-chlorophenyl)-5-(4-chlorophenyl)-4-methoxy-3-[N-(4-methoxycarbonyl-tetrahydropyran-4-yl)carbamoyl]-1H-pyrazole (150 mg, Yield: 74%) as a colorless solid.

MS (APCI) m/z; 504/506 [M+H]$^+$ (2) The compound obtained in the above step (1) (150 mg) was treated in the same manner as described in Example 275(3) to obtain 1-(2-chlorophenyl)-5-(4-chlorophenyl)-4-methoxy-3-[N-(4-carboxy-tetrahydropyran-4-yl)carbamoyl]-1H-pyrazole (137.3 mg, Yield: 93%) as a colorless solid.

MS (APCI) m/z; 490/492 [M+H]$^+$ (3) The compound obtained in the above step (2) (34 mg) was treated in the same manner as described in Example 275(4) to obtain 1-(2-chlorophenyl)-5-(4-chlorophenyl)-4-methoxy-3-[N-(4-carbamoyl-tetrahydropyran-4-yl)carbamoyl]-1H-pyrazole (31 mg, Yield: 90%) as a solid.

MS (APCI) m/z; 489/491 [M+H]$^+$

Example 282

(1) The compound obtained in Example 275(1) (200 mg) was treated in the same manner as described in Example 275(3) to obtain 1-(2-chlorophenyl)-5-(4-chlorophenyl)-4-methoxy-3-[N-(4-carboxy-tetrahydrothiopyran-4-yl)carbamoyl]-1H-pyrazole (146 mg, Yield: 76%) as a colorless solid.

MS (APCI) m/z; 506/508 [M+H]$^+$ (2) The compound obtained in the above step (1) (35 mg) was treated in the same manner as described in Example 275(4) to obtain 1-(2-chlorophenyl)-5-(4-chlorophenyl)-4-methoxy-3-[N-(4-carbamoyl-tetrahydrothiopyran-4-yl)carbamoyl]-1 H-pyrazole (31.1 mg, Yield: 88%) as a solid.

MS (APCI) m/z; 505/507 [M+H]$^+$

Example 283

(1) The compound obtained in Reference Example 1(6) (109 mg) and the compound obtained in Reference Example 47 (94 mg) were treated in the same manner as described in Example 1 to obtain 1-(2-chlorophenyl)-5-(4-chlorophenyl)-4-methoxy-3-[N-(4-methoxycarbonyl-4-phenylpiperidin-1-yl)carbamoyl]-1H-pyrazole (142.8 mg, Yield: 82%) as a colorless solid.

MS (APCI) m/z; 579/581 [M+H]$^+$ (2) To a solution of the compound obtained in the above step (1) (140 mg) in ethanol (3 mL) was added an aqueous 2N sodium hydroxide solution (250 µL) and the mixture was stirred at 50° C. for 2 hours. To the reaction mixture was added tetrahydrofuran (2 mL) and the mixture was stirred at 80° C. for 2 days. After cooling to room temperature, to the reaction mixture was added an aqueous 2N HCl (250 µL) and the mixture was stirred and extracted with chloroform. The extract was dried over magnesium sulfate and filtered. The filtrate was concentrated in vacuo and the residue was diluted with dimethylformamide (2 mL). Thereto was added ammonium chloride (18 mg), water soluble carbodiimide hydrochloride (65 mg), 1-hydroxybenzotriazole hydrate (52 mg) and triethylamine (95 µL) and the mixture was stirred at room temperature overnight. To the reaction mixture was added an aqueous saturated sodium hydrogencarbonate solution and the mixture was stirred and extracted with chloroform. The organic layer was washed with water and concentrated. The resultant crude product was washed with diisopropylether to obtain 1-(2-chlorophenyl)-5-(4-chlorophenyl)-4-methoxy-3-[N-(4-carbamoyl-4-phenylpiperidin-1-yl)carbamoyl]-1H-pyrazole (25.5 mg, Yield: 19%) as a colorless solid.

MS (APCI) m/z; 564/566 [M+H]$^+$

Example 284

(1) To a solution of the compound obtained in Reference Example 1(4) (3.77 g), tert-butyl N-(2-hydroxyethyl)carbamate (1.61 g) and triphenylphosphine (2.62 g) in tetrahydrofuran (100 mL) was added dropwise 2.2N diethyl azodicarboxylate-toluene solution (4.5 mL) under ice-cooling and the mixture was stirred at room temperature overnight. To the reaction mixture was added water and the mixture was extracted with ethyl acetate. The extract was dried over magnesium sulfate and concentrated in vacuo. The resultant crude product was purified by column chromatography on silica gel (solvent: hexane/ethyl acetate=80/20 to 60/40) to obtain 4-[2-(tert-butoxycarbonyl-amino)ethoxy-1-(2-chlorophenyl)-5-(4-chlorophenyl)-3-ethoxycarbonyl-1H-pyrazole (3.37 g, Yield: 65%) as a solid.

MS (APCI) m/z; 520/522 [M+H]$^+$ (2) To a solution of the compound obtained in the above step (1) (2.60 g) in ethanol (20 mL) was added an aqueous 1N sodium hydroxide solution (15 mL) and the mixture was stirred at room temperature overnight. The resultant precipitates were collected by filtration, washed with water-ethanol and dried to obtain 4-[2-(tert-butoxy-carbonylamino)ethoxy-3-carboxy-1-(2-chlorophenyl)-5-(4-chlorophenyl)-1H-pyrazole (2.47 g, Yield: 99%) as a solid.

MS (APCI) m/z; 490/492 [M+H]$^+$ (3) To a solution of the compound obtained in the above step (2) (2.47 g), 1-hydroxybenzotriazole (1.53 g) and triethylamine (2.02 g) in N,N-dimethylformamide (50 mL) was added water-soluble carbodiimide hydrochloride (1.92 g) at room temperature and the mixture was stirred overnight. To the reaction mixture was added water and the mixture was extracted with ethyl acetate. The extract was dried over magnesium sulfate and concentrated in vacuo. The resultant crude product was purified by column chromatography on silica gel (solvent: hexane/ethyl acetate=65/35 to 45/55) to obtain 4-[2-(tert-butoxycarbonylamino)ethoxy-1-(2-chlorophenyl)-5-(4-chlorophenyl)-3-[N-(1-pyrrolidinyl)carbamoyl]-1H-pyrazole (2.07 g, Yield: 74%) as a solid.

MS (APCI) m/z; 560/562 [M+H]$^+$ (4) To a solution of the compound obtained in the above step (3) (1.68 g) in dioxane (4 mL) was added 4N HCl-dioxane at room temperature and the mixture was stirred overnight. The reaction mixture was concentrated in vacuo and the residue was washed with ether-ethanol and dried to obtain 4-(2-aminoethoxy)-1-(2-chlorophenyl)-5-(4-chlorophenyl)-3-[N-(1-pyrrolidinyl)carbamoyl]-1H-pyrazole hydrochloride (1.55 g, Yield: 97%) as a solid.

MS (APCI) m/z; 460/462 [M+H]$^+$ (5) The compound obtained in the above step (4) (100 mg) was treated by column chromatography on NH-silica gel (solvent; chloroform/methanol=100/0 to 94/6) to obtain 4-(2-aminoethoxy)-1-(2-chlorophenyl)-5-(4-chlorophenyl)-3-[N-(1-pyrrolidinyl)carbamoyl]-1H-pyrazole (57 mg, Yield: 66%) as a powder.

MS (APCI) m/z; 460/462 [M+H]$^+$

Example 285

To a solution of the compound obtained in Example 284(4) (99 mg) in methylene chloride (2 mL) was added acetyl chloride (79 mg) and triethylamine (151 mg) and the mixture was stirred overnight. To the reaction mixture was added an aqueous saturated sodium hydrogencarbonate solution and the mixture was extracted with chloroform. The extract was dried over magnesium sulfate and concentrated in vacuo. The resultant crude product was purified by column chromatography on silica gel (solvent: chloroform/methanol=100/0 to 94/6) to obtain 4-[2-(acetylamino)ethoxy]-1-(2-chlorophenyl)-5-(4-chlorophenyl)-3-[N-(1-pyrrolidinyl)carbamoyl]-1H-pyrazole (20 mg, Yield: 20%) as a powder.

MS (APCI) m/z; 502/504 [M+H]$^+$

Example 286

The compound obtained in Example 284(4) (99 mg) and methanesulfonyl chloride (115 mg) were treated in the same manner as described in Example 285 to obtain 1-(2-chlorophenyl)-5-(4-chlorophenyl)-4-[2-(methylsulfonylamino)ethoxy]-3-[N-(1-pyrrolidinyl)carbamoyl]-1H-pyrazole (83 mg, Yield: 77%) as a powder.

MS (APCI) m/z; 538/540 [M+H]$^+$

Example 287

The compound obtained in Example 284(4) (99 mg) and dimethylsulfamoyl chloride (144 mg) were treated in the same manner as described in Example 285 to obtain 1-(2-chlorophenyl)-5-(4-chlorophenyl)-4-[2-(dimethylaminosulfonyl)ethoxy]-3-[N-(1-pyrrolidinyl)carbamoyl]-1H-pyrazole (71 mg, Yield: 63%) as a powder.

MS (APCI) m/z; 567/569 [M+H]$^+$

Example 288

The compound obtained in Example 284(4) (99 mg) and ethyl isocyanate (71 mg) were treated in the same manner as described in Example 285 to obtain 1-(2-chlorophenyl)-5-(4-chlorophenyl)-4-[2-(N'-ethylureido)ethoxy]-3-[N-(1-pyrrolidin yl)carbamoyl]-1H-pyrazole (79 mg, Yield: 74%) as a powder.

MS (APCI) m/z; 531/533 [M+H]$^+$

Example 289

(1) To a solution of the compound obtained in Reference Example 1(6) (3.63 g), 7N ammonia-methanol (6 mL), 1-hydroxybenzotriazole (3.06 g) and triethylamine (1.01 g) in N,N-dimethylformamide (100 mL) was added water-soluble carbodiimide hydrochloride (3.83 g) at room temperature and the mixture was stirred overnight. To the reaction mixture was added an aqueous saturated sodium hydrogencarbonate solution and the mixture was extracted with chloroform. The extract was dried over magnesium sulfate and concentrated in vacuo. The resultant crude product was washed with ether and dried to give 1-(2-chlorophenyl)-5-(4-chlorophenyl)-4-methoxy-3-carbamoyl-1H-pyrazole (2.04 g, Yield: 56%) as a solid.

MS (APCI) m/z; 362/364 [M+H]$^+$ (2) A solution of the compound obtained in the above step (1) (1.81 g) and Lawesson's reagent (2.02 g) in toluene (10 mL) was refluxed under heating and stirring for 2 hours. After cooling, to the reaction mixture was added NH-silica gel (2 g) and the mixture was filtered. The filtrate was concentrated in vacuo and the resultant crude product was purified by column chromatography on silica gel (solvent: hexane/ethyl acetate=85/15 to 65/35) to obtain 1-(2-chlorophenyl)-5-(4-chlorophenyl)-4-methoxy-3-thiocarbamoyl-1H-pyrazole (0.69 g, Yield: 37%) as a solid.

MS (APCI) m/z; 378/380 [M+H]$^+$ (3) A solution of the compound obtained in the above step (2) (70 mg) and hydrazine hydrate (125 mg) in ethanol (2.5 mL) was refluxed under heating and stirring for 2 hours. After cooling, the reaction mixture was concentrated in vacuo and to the residue was added water. The mixture was extracted with chloroform and the extract was dried over magnesium sulfate and concentrated in vacuo. To a solution of the resultant crude product and triethylamine (151 mg) in methylene chloride (2.5 mL) was added 1-[4-(trifluoromethyl)pyrimidin-2-yl]piperidin-4-carbonyl chloride (293 mg) and the mixture was stirred at room temperature overnight. To the reaction mixture was added an aqueous saturated sodium hydrogencarbonate solution and the mixture was extracted with chloroform. The extract was dried over magnesium sulfate and concentrated in vacuo. The resultant crude product was purified by column chromatography on silica gel (solvent: hexane/ethyl acetate=50/50 to 30/70) to obtain 1-(2-chlorophenyl)-5-(4-chlorophenyl)-4-methoxy-3-[5-[1-(4-trifluoromethylpyrimidin-2-yl)pyrrolidin-4-yl]-1,2,4-triazol-3-yl]-1H-pyrazole (19 mg, Yield: 12%) as a solid.

MS (APCI) m/z; 615/617 [M+H]$^+$

Examples 290 to 308

The corresponding materials were treated in the same manner as described in Example 1 to obtain the compounds as shown in the following Table 12.

TABLE 12

(No. 1)

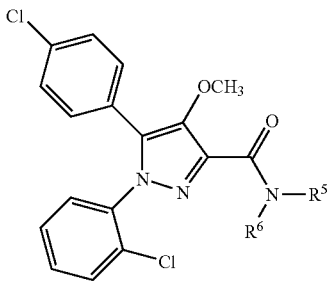

| Example Nos. | —N(R$^5$)(R$^6$) | Physicochemical properties etc. |
|---|---|---|
| 290 | HN-N piperidine with two F | powder<br>MS(APCI): 481/483 [M + H]$^+$ |
| 291 | HN-N piperidine with F | powder<br>MS(APCI): 463/465 [M + H]$^+$ |
| 292 | HN-N piperidine-4-F | powder<br>MS(APCI): 463/465 [M + H]$^+$ |
| 293 | HN-pyrimidin-2-yl | powder<br>MS(APCI): 440/442 [M + H]$^+$ |

TABLE 12-continued
| 294 | 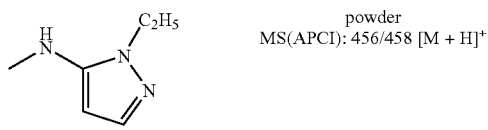 | powder MS(APCI): 456/458 [M + H]+ |
| 295 |  | powder MS(APCI): 454/456 [M + H]+ |
(No. 2)
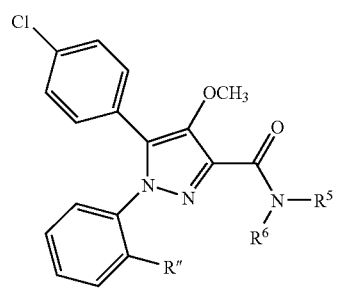
| Example Nos. | R″ | —N(R⁵)(R⁶) | Physicochemical properties etc. |
|---|---|---|---|
| 296 | Cl | 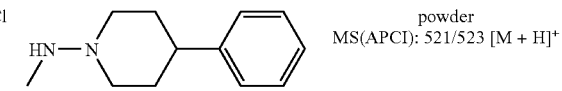 | powder MS(APCI): 521/523 [M + H]+ |
| 297 | Cl | 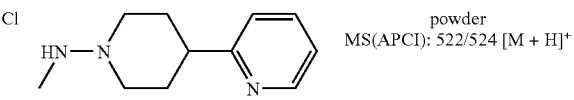 | powder MS(APCI): 522/524 [M + H]+ |
| 298 | Cl | 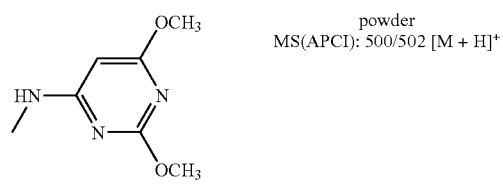 | powder MS(APCI): 500/502 [M + H]+ |
| 299 | Cl | 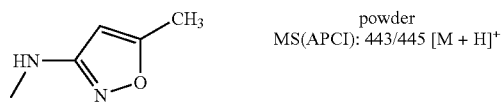 | powder MS(APCI): 443/445 [M + H]+ |
| 300 | F | 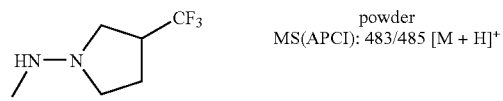 | powder MS(APCI): 483/485 [M + H]+ |
| 301 | F |  | solid MS(APCI): 465/467 [M + H]+ |

TABLE 12-continued (No. 3)

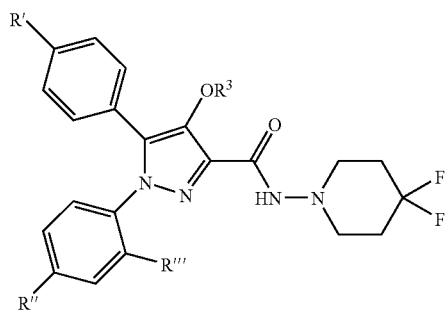

| Example Nos. | R' | R'' | R''' | R³ | Physicochemical properties etc. |
|---|---|---|---|---|---|
| 302 | CF₃ | H | Cl | CH₃ | solid<br>MS(APCI): 515/517 [M + H]⁺ |
| 303 | CF₃ | F | Cl | CH₃ | solid<br>MS(APCI): 533/535 [M + H]⁺ |
| 304 | CF₃ | Cl | Cl | CH₃ | solid<br>MS(APCI): 549/551 [M + H]⁺ |
| 305 | CF₃ | H | Cl | CHF₂ | solid<br>MS(APCI): 551/553 [M + H]⁺ |
| 306 | CF₃ | F | Cl | CHF₂ | solid<br>MS(APCI): 569/571 [M + H]⁺ |
| 307 | Cl | H | Cl | CHF₂ | solid<br>MS(APCI): 517/519 [M + H]⁺ |
| 308 | CF₃ | Cl | Cl | CHF₂ | solid<br>MS(APCI): 585/587 [M + H]⁺ |

Examples 309 to 324

The corresponding materials were treated in the same manner as described in Example 22(3) to obtain the compounds as shown in the following Table 13.

TABLE 13

(No. 1)

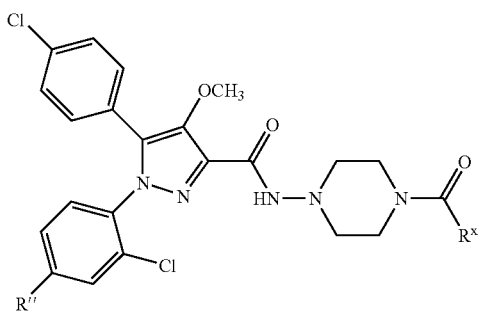

| Example Nos. | R'' | Rˣ | Physicochemical properties etc. |
|---|---|---|---|
| 309 | H | ⌒CF₃ | powder<br>MS(APCI): 556/558 [M + H]⁺ |
| 310 | H | ⌒OCH₃ | powder<br>MS(APCI): 518/520 [M + H]⁺ |
| 311 | H | ⌒CN | powder<br>MS(APCI): 513/515 [M + H]⁺ |

TABLE 13-continued

| 312 | Cl | 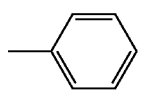 | powder<br>MS(APCI): 584/586 [M + H]⁺ |
|---|---|---|---|
| 313 | Cl | 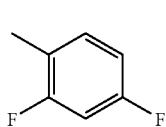 | powder<br>MS(APCI): 620/622 [M + H]⁺ |
| 314 | Cl | 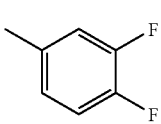 | powder<br>MS(APCI): 620/622 [M + H]⁺ |
| 315 | Cl | 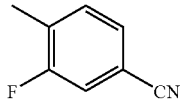 | powder<br>MS(APCI): 627/629 [M + H]⁺ |
| 316 | Cl | CF₃ | powder<br>MS(APCI): 576/578 [M + H]⁺ |
| 317 | Cl | 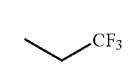 | powder<br>MS(APCI): 590/592 [M + H]⁺ |

TABLE 13-continued (No. 2)

[Structure: 5-(4-chlorophenyl)-4-methoxy-1-(2-fluorophenyl)-1H-pyrazole-3-carboxamide linked via HN to piperazine with N-C(=O)-R^x]

| Example Nos. | R^x | Physicochemical properties etc. |
|---|---|---|
| 318 | 4-Cl-C6H4- | powder<br>MS(APCI): 568/570 [M + H]+ |
| 319 | 3-Cl-C6H4- | powder<br>MS(APCI): 568/570 [M + H]+ |
| 320 | 2-Cl-C6H4- | powder<br>MS(APCI): 568/570 [M + H]+ |
| 321 | 4-F-C6H4- | powder<br>MS(APCI): 552/554 [M + H]+ |
| 322 | 4-CF3-C6H4- | powder<br>MS(APCI): 602/604 [M + H]+ |
| 323 | 4-CN-C6H4- | powder<br>MS(APCI): 559/561 [M + H]+ |
| 324 | 4-OCH3-C6H4- | powder<br>MS(APCI): 564/566 [M + H]+ |

Examples 325 to 335

The corresponding materials were treated in the same manner as described in Example 21 and then the resultant product was treated in the same manner as described in Example 28 to obtain the compound as shown in the following Table 14.

TABLE 14

(No. 1)

[Structure: 5-(4-chlorophenyl)-4-methoxy-1-(2-chlorophenyl)-3-(5-R-1,3,4-oxadiazol-2-yl)-1H-pyrazole]

| Example Nos. | R | Physicochemical properties etc. |
|---|---|---|
| 325 | -CH(CH3)2 | solid<br>MS(APCI): 429/431 [M + H]+ |
| 326 | -CH2CH2OCH3 | solid<br>MS(APCI): 431/433 [M + H]+ |
| 327 | CF3 | powder<br>MS(APCI): 455/457 [M + H]+ |
| 328 | 1-methylcyclopropyl | solid<br>MS(APCI): 503/505 [M + H]+ |
| 329 | 1-hydroxycyclopropylmethyl | solid<br>MS(APCI): 443/445 [M + H]+ |
| 330 | -C(CH3)2Cl | solid<br>MS(APCI): 463/465 [M + H]+ |
| 331 | -CH2CH2SCH3 | solid<br>MS(APCI): 433/435 [M + H]+ |

(No. 2)

[Structure: 5-(4-R'-phenyl)-4-methoxy-1-(2-chloro-4-R''-phenyl)-3-(5-(2,2,2-trifluoroethyl)-1,3,4-oxadiazol-2-yl)-1H-pyrazole]

| Example Nos. | R' | R'' | Physicochemical properties etc. |
|---|---|---|---|
| 332 | Cl | Cl | solid<br>MS(APCI): 503/505 [M + H]+ |
| 333 | CF3 | H | powder<br>MS(APCI): 503/505 [M + H]+ |
| 334 | CF3 | F | powder<br>MS(APCI): 521/523 [M + H]+ |
| 335 | CF3 | Cl | powder<br>MS(APCI): 537/539 [M + H]+ |

Example 336

(1) A solution of oxalyl chloride (1.92 mL) in methylene chloride (70 mL) was cooled to −74° C. under nitrogen-gas atmosphere and thereto was added dropwise dimethylsulfoxide (3.22 mL) over a period of 15 minutes. The mixture was stirred at the same temperature for 20 minutes and thereto was added dropwise a solution of 1-benzhydryl-3-hydroxyazetidine (5 g) in methylene chloride (25 mL) over a period of 45 minutes. The mixture was stirred at the same temperature for 75 minutes. Thereto was added dropwise triethylamine (11.6 mL) over a period of 20 minutes and the mixture was stirred at the same temperature for 150 minutes. The reaction mixture was warmed to 0° C. and thereto was added dropwise an aqueous 1N HCl solution (64 mL). The mixture was stirred at room temperature and the aqueous layer was separated. To the organic layer was added an aqueous 1N HCl solution. The mixture was stirred and the aqueous layer was separated (said extraction procedure was repeated three times). The combined aqueous layer was neutralized (pH 9) with an aqueous 2N sodium hydroxide solution under stirring and extracted with ethyl acetate. The extract was washed with a brine, dried over magnesium sulfate and filtered. The filtrate was concentrated in vacuo and the resultant crude product was purified by column chromatography on silica gel (solvent: hexane/ethyl acetate=100/0 to 90/10) to obtain 1-benzhydrylazetidin-3-one (4.57 g, Yield: 92%) as a white solid.

MS (APCI) m/z; 238 [M+H]$^+$ (2) To a solution of the compound obtained in the above step (1) (10.76 g) in methanol (110 mL) was added dimethylamine hydrochloride (4.89 g), acetic acid (3.42 mL) and potassium cyanide (3.92 g) and the mixture was stirred at 55° C. for 115 minutes. After cooling to room temperature, to the reaction mixture was added an aqueous saturated sodium hydrogencarbonate solution (150 mL) and the mixture was stirred at room temperature for 45 minutes. The mixture was extracted with ethyl acetate and the organic layer was washed successively with an aqueous sodium hydrogencarbonate solution and a brine, dried over magnesium sulfate and filtered. The filtrate was concentrated in vacuo and the resultant crude product was purified by column chromatography on silica gel (solvent: hexane/ethyl acetate=5/1 to 4/1) to obtain 1-benzhydryl-4-cyano-4-dimethylaminoazetidine (13.55 g, Yield: 100%) as a yellow viscosity.

MS (APCI) m/z; 292 [M+H]$^+$ (3) To a solution of the compound obtained in the above step (2) (13.5 g) in methylene chloride (275 mL) was added dropwise concentrated sulfuric acid (25.5 mL) over a period of 10 minutes under ice-cooling and the mixture was stirred at room temperature for 41 hours. The reaction mixture was added dropwise to ice-cooled water and then basified (pH 11) with an aqueous 2N sodium hydroxide solution under stirring. The mixture was extracted with methylene chloride and the organic layer was washed with an aqueous sodium hydrogencarbonate solution, dried over magnesium sulfate and filtered. The filtrate was concentrated in vacuo and the residue was recrystallized from ethyl acetate to give 1-benzhydryl-4-carbamoyl-4-dimethylaminoazetidine (9.47 g, yield: 68%) as a colorless solid.

MS (APCI) m/z; 310 [M+H]$^+$ (4) To a solution of the compound obtained in the above step (3) (3.95 g) in methanol (80 mL) was added 1N HCl-dioxane (12.8 mL) and 10% palladium-carbon (1.36 g) and the mixture was stirred at room temperature under nitrogen-gas atmosphere for 3 hours. The reaction mixture was filtered and the filtrate was concentrated in vacuo. To the residue was added diethylether and the mixture was stirred. The resultant crystals were collected by filtration and dried in vacuo to give 4-carbamoyl-4-dimethylaminoazetidine hydrochloride (2.20 g, yield: 96%) as a colorless solid.

MS (APCI) m/z; 144 [M+H]$^+$ (5) To a solution of the compound obtained in the above step (4) (180 mg) in water (2 mL) was added an aqueous 2N sodium hydroxide solution (500 μL) and the mixture was stirred at room temperature for 30 minutes. To the reaction mixture was added sodium nitrite (138 mg) and acetic acid (93 μL) under ice-cooling and the mixture was stirred at room temperature overnight. To the reaction mixture was added an aqueous saturated sodium hydrogencarbonate solution. After stirring, the mixture was concentrated in vacuo and the crude product was purified by column chromatography on silica gel (solvent: hexane/ethyl acetate=30/70 to 0/100) and dried in vacuo to obtain 4-carbamoyl-4-dimethylamino-1-nitrosoazetidine (137 mg, Yield: 79%) as a pale yellow solid.

MS (APCI) m/z; 173 [M+H]$^+$ (6) To a solution of the compound obtained in the above step (5) (69 mg) in ethanol (2 mL) was added tin(II) chloride dihydrate (316 mg) and the mixture was refluxed under heating and stirring for one day. After cooling to room temperature, the reaction mixture was concentrated in vacuo. To the residue was added chloroform and the mixture was stirred and filtered through Celite. The filtrate was concentrated in vacuo and the residue was dissolved in N,N-dimethylformamide (3 mL). Thereto was added the compound obtained in Reference Example 1(6) (145 mg) and the mixture was treated in the same manner as described in Example 1 to give 1-(2-chlorophenyl)-5-(4-chlorophenyl)-4-methoxy-3-[N-[3-carbamoyl-3-(dimethylamino)azetidin-1-yl]carbamoyl]-1H-pyrazole (compound a; 4.7 mg, Yield: 2.7%) as a pale yellow solid and 1-(2-chlorophenyl)-5-(4-chlorophenyl)-3-[[3-carbamoyl-3-(dimethylamino)azetidin-1-yl]carbonyl]-4-methoxy-1H-pyrazole (compound b; 45.5 mg, Yield: 27%) as a colorless solid.

Compound a; MS (APCI) m/z; 488/490 [M+H]$^+$

Compound b; MS (APCI) m/z; 503/505 [M+H]$^+$

Example 337

(1) To a solution of 2,5-dichloropyridine (2 g) in dimethylformamide (30 mL) was added potassium carbonate (3.73 g) and piperazine (1.16 g) and the mixture was stirred at 110° C. for 4 hours. After cooling the reaction mixture, thereto was added ethyl acetate and an aqueous saturated sodium hydrogencarbonate solution and the mixture was extracted with ethyl acetate. The organic layer was washed with water, dried over magnesium sulfate and filtered. The filtrate was concentrated in vacuo and the resultant crude product was purified by column chromatography on NH-silica gel (Chromatorex NH-silica gel, solvent: chloroform/methanol=100/0 to 99/1) to obtain 5-chloro-2-(1-piperazinyl)pyridine (0.28 g, Yield: 10%) as a pale yellow solid.

MS (APCI) m/z; 198/200 [M+H]$^+$ (2) The compound obtained in the above step (1) (270 mg) was treated in the same manner as described in Example 336(5) to give 5-chloro-2-(4-nitroso-piperazin-1-yl)pyridine as a pale yellow solid.

(3) A solution of the compound obtained in the above step (2) in tetrahydrofuran (4 mL) was cooled to 0° C. Thereto was gradually added lithium aluminum hydride (91 mg) and the mixture was stirred for 1 hour. To the reaction mixture was gradually added an aqueous saturated sodium hydrogencarbonate solution and the mixture was extracted with chloroform. The organic layer was dried over magnesium sulfate and filtered. The filtrate was concentrated in vacuo to give 2-(4-aminopiperazin-1-yl)-5-chloropyridine (276 mg,) as a pale yellow solid.

MS (APCI) m/z; 213/215 [M+H]$^+$ (4) The compound obtained in Reference Example 1(6) (100 mg) and the compound obtained in the above step (3) (59 mg) were treated in the same manner as described in Example 1 to give 1-(2-chlorophenyl)-5-(4-chlorophenyl)-3-[N-[4-(5-chloropyridin-2-yl)piperazin-1-yl]carbamoyl]-4-methoxy-1H-pyrazole (96 mg, yield: 63%) as a colorless powder.
MS (APCI) m/z; 557/559 [M+H]⁺

Example 338

To a solution of the compound obtained in Reference Example 22(2) (60 mg) in dimethylformamide (1.2 mL) was added potassium carbonate (50 mg) and 6-chloronicotinnitrile (50 mg) and the mixture was stirred at 170° C. in a microwave reactor for 1 hour. After cooling the reaction mixture, thereto was added ethyl acetate and water and the mixture was extracted with ethyl acetate. The organic layer was washed with water, dried over magnesium sulfate and filtered. The filtrate was concentrated in vacuo and the resultant crude product was purified by column chromatography on silica gel (solvent: hexane/ethyl acetate=50/50 to 30/70) to obtain 1-(2-chlorophenyl)-5-(4-chlorophenyl)-3-[N-[4-(5-cyanopyridin-2-yl)piperazin-1-yl]carbamoyl]-4-methoxy-1H-pyrazole (20.8 mg, yield: 28%) as a colorless powder.
MS (APCI) m/z; 548/550 [M+H]⁺

Example 339

The corresponding materials were treated in the same manner as described in Example 338 to give 1-(2-chlorophenyl)-5-(4-chlorophenyl)-3-[N-[4-(5-difluoromethyl-pyridin-2-yl)piperazin-1-yl]carbamoyl]-4-methoxy-1H-pyrazole as a colorless powder.
MS (APCI) m/z; 573/575 [M+H]⁺

Examples 340 to 351

The corresponding materials were treated in the same manner as described in Example 337 to obtain the compounds as shown in the following Table 15.

TABLE 15

(No. 1)

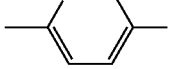

| Example Nos. | R″ | R″″ | Physicochemical properties etc. |
|---|---|---|---|
| 340 | Cl | 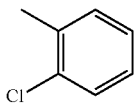 | powder MS(APCI): 591/593 [M + H]⁺ |
| 341 | F | 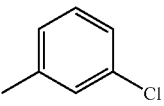 | powder MS(APCI): 540/542 [M + H]⁺ |
| 342 | F | 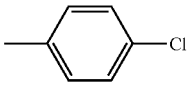 | powder MS(APCI): 540/542 [M + H]⁺ |
| 343 | F | 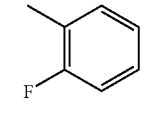 | powder MS(APCI): 540/542 [M + H]⁺ |
| 344 | F | 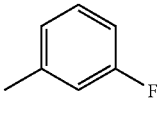 | powder MS(APCI): 524/526 [M + H]⁺ |
| 345 | F | 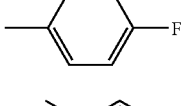 | powder MS(APCI): 524/526 [M + H]⁺ |
| 346 | F | 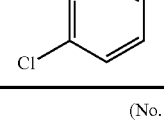 | powder MS(APCI): 524/526 [M + H]⁺ |
| 347 | Cl | 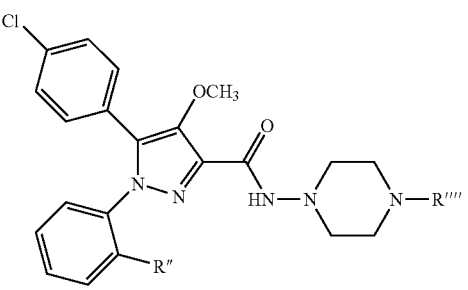 | powder MS(APCI): 556/558 [M + H]⁺ |

(No. 2)

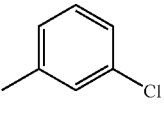

| Example Nos. | R″ | R″″ | Physicochemical properties etc. |
|---|---|---|---|
| 348 | Cl | 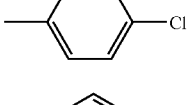 | powder MS(APCI): 556/558 [M + H]⁺ |
| 349 | Cl | 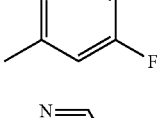 | powder MS(APCI): 556/558 [M + H]⁺ |
| 350 | Cl | 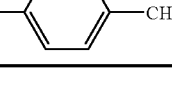 | powder MS(APCI): 540/542 [M + H]⁺ |
| 351 | Cl |  | powder MS(APCI): 537/539 [M + H]⁺ |

Example 352

(1) To a solution of the compound obtained in Reference Example 1(6) (750 mg) in methanol (10 mL) was added an aqueous 1N sodium hydroxide solution (5 mL) at room temperature and the mixture was stirred overnight. To the reaction mixture was added an aqueous 2N HCl solution and the mixture was extracted with chloroform. The extract was dried over magnesium sulfate and concentrated in vacuo. The resultant crude product was washed with methanol and dried to give 3-carboxy-1-(2-chlorophenyl)-5-(4-chlorophenyl)-4-hydroxy-1H-pyrazole (626 mg, Yield: 90%) as a solid.

MS (APCI) m/z; 349/351 [M+H]$^+$ (2) To a solution of the compound obtained in the above step (1) (620 mg), 4-aminotetrahydropyrane (300 mg), 1-hydroxybenzotriazole (460 mg) and triethylamine (300 mg) in N,N-dimethylformamide (15 mL) was added water-soluble carbodiimide hydrochloride (570 mg) at room temperature and the mixture was stirred overnight. To the reaction mixture was added an aqueous saturated sodium hydrogencarbonate solution and the mixture was extracted with chloroform. The extract was dried over magnesium sulfate and concentrated in vacuo. The resultant crude product was purified by column chromatography on silica gel (solvent: hexane/ethyl acetate=75/25 to 0/100) to obtain 1-(2-chlorophenyl)-5-(4-chlorophenyl)-4-hydroxy-3-[N-(4-tetrahydropyranyl)carbamoyl]-1H-pyrazole (272 mg, Yield: 35%) as a solid.

MS (APCI) m/z; 432/434 [M+H]$^+$ (3) To a suspension of the compound obtained in the above step (2) (129 mg) and cesium carbonate (163 mg) in N,N-dimethylformamide (3 mL) was added bromoacetonitrile (180 mL) at room temperature and the mixture was stirred at the same temperature for 6 hours. To the reaction mixture was added water and the mixture was extracted with ethyl acetate. The extract was dried over magnesium sulfate and concentrated in vacuo. The resultant crude product was purified by column chromatography on silica gel (solvent: hexane/ethyl acetate =60/40 to 40/60) to obtain 1-(2-chlorophenyl)-5-(4-chlorophenyl)- 4-cyanomethoxy-34N-(4-tetrahydropyranyl)carbamoyl]-1H-pyrazole (135 mg, Yield: 95%) as a solid.

MS (APCI) m/z; 471/473 [M+H]$^+$

Examples 353 to 355

The corresponding materials were treated in the same manner as described in Example 23 to obtain the compounds as shown in the following Table 16.

TABLE 16

| Example Nos. | R" | Physicochemical properties etc. |
|---|---|---|
| 353 | H | solid<br>MS(APCI): 565/567 [M + H]$^+$ |
| 354 | Cl | solid<br>MS(APCI): 599/601 [M + H]$^+$ |
| 355 | F | solid<br>MS(APCI): 583/585 [M + H]$^+$ |

Examples 356 to 359

The corresponding materials were treated in the same manner as described in Example 1 to obtain the compounds as shown in the following Table 17.

TABLE 17

| Example Nos. | R'''' | Physicochemical properties etc. |
|---|---|---|
| 356 | —C(O)CH$_2$NH$_2$ | solid<br>MS(APCI): 488/490 [M + H]$^+$ |
| 357 | —N(CH$_3$)C(O)CH$_2$CF$_3$ (NH form) | solid<br>MS(APCI): 570/572 [M + H]$^+$ |
| 358 | —N(CH$_3$)C(O)Ph | solid<br>MS(APCI): 564/566 [M + H]$^+$ |
| 359 | —N(CH$_3$)C(O)CH$_2$CF$_3$ | solid<br>MS(APCI): 584/586 [M + H]$^+$ |

Examples 360

The corresponding materials were treated in the same manner as described in Example 22(1) to (2) to obtain 5-(4-chlorophenyl)-1-(2,4-dichlorophenyl)-4-methoxy-3-[N-(1-piperazinyl)carbamoyl]-1H-pyrazole (560 mg, Yield: 81%) as a powder.

MS (APCI) m/z; 480/482 [M+H]$^+$

Example 361

The corresponding materials were treated in the same manner as described in Example 22(3) to obtain 1-(2-chlorophenyl)-5-(4-chlorophenyl)-4-methoxy-3-[N-[4-[2-(methylsulfonyl)acetyl]piperazin-1-yl]carbamoyl]-1H-pyrazole (28 mg, Yield: 63%) as a powder.

MS (APCI) m/z; 566/568 [M+H]$^+$

Example 362

To a suspension of the compound obtained in Example 352(2)(129 mg) and cesium carbonate (163 mg) in N,N-dimethylformamide (3 mL) was added ethyl bromodifluoroacetate (305 mg) at room temperature and the mixture was stirred at room temperature for 6 hours. To the reaction mixture was added water and the mixture was extracted with ethyl acetate. The extract was dried over magnesium sulfate and concentrated in vacuo. The resultant crude product was purified by column chromatography on silica gel (solvent: hexane/ethyl acetate =60/40 to 40/60) to obtain 1-(2-chlorophenyl)-5-(4-chlorophenyl)-4-(ethoxycarbonyl) (difluoro)methoxy-34N-(4-tetrahydropyranyl)carbamoyl]-1H-pyrazole (74 mg, Yield: 44%) as a powder.

MS (APCI) m/z; 554/556 [M+H]$^+$

Examples 363 to 364

The corresponding materials were treated in the same manner as described in Example 279 to obtain the compounds as shown in the following Table 18.

TABLE 18

| Example Nos. | —N(R$^5$)(R$^6$) | Physicochemical properties etc. |
|---|---|---|
| 363 | (azetidinyl-N-methylimidazolidinone structure) | solid MS(APCI): 472/474 [M + H]$^+$ |

TABLE 18-continued

| Example Nos. | —N(R$^5$)(R$^6$) | Physicochemical properties etc. |
|---|---|---|
| 364 | (azetidine with N(CH$_3$)$_2$ and CONH$_2$ substituents) | solid MS(APCI): 474/476 [M + H]$^+$ |

Reference Example 1

(1) To a solution of ethyl malonate potassium salt (39 g) in acetonitrile (100 mL) was added magnesium chloride (26 g) and triethylamine (48.6 g) and the mixture was stirred at room temperature for 2 hours (solution A). To a solution of 4-chlorophenylacetic acid (18.6 g) in acetonitrile (100 mL) was added carbonyldiimidazole (19.5 g) at room temperature and the mixture was stirred at the same temperature fro 1.5 hours. To the reaction mixture was added the solution A prepared above at room temperature and the mixture was stirred at the same temperature for 30 minutes and at 80° C. for 2 hours. After cooling the reaction mixture to room temperature, thereto was added 2N HCl solution (260 mL) and the mixture was stirred. The organic layer was washed with an aqueous sodium hydrogencarbonate solution and a brine, dried over magnesium sulfate and filtered. The filtrate was concentrated in vacuo and the resultant crude product was purified by column chromatography on silica gel (solvent: hexane/ethyl acetate=8/1 to 6/1) to obtain ethyl 4-(4-chlorophenyl)-3-oxobutyrate (25 g, yield: 95%) as a liquid.

MS (APCI) m/z; 241/243[M+H]$^+$ (2) To a solution of 2-chloroaniline (13.3 g) in 2N HCl was added dropwise an aqueous solution of sodium nitrite (7.9 g) over a period of 10 minutes under ice cooling and the mixture was stirred at the same temperature for 2 hours (solution B). To a solution of the compound obtained in the above step (1) (25 g) in ethanol (300 mL) was added sodium acetate (27.2 g) at room temperature and the mixture was ice-cooled. Thereto was added the solution B prepared as above and the mixture was stirred at the same temperature for 30 minutes and at room temperature for 1 hour. The resultant solid materials were collected by filtration with glass filter, washed with water and dissolved in chloroform. The solution was washed with a brine and the organic layer was dried over magnesium sulfate and filtered. The filtrate was concentrated in vacuo and the resultant solid materials were washed with hexane and dried in vacuo to obtain ethyl 4-(4-chlorophenyl)-2-[(2-chlorophenyl)hydrazono]-3-oxobutyrate (32.3 g, yield: 82%) as a powder.

MS (APCI) m/z; 379/381[M+H]$^+$ (3) To a solution of the compound obtained in the above step (2) (32.2 g) in chloroform (500 mL) was added dropwise bromine (4.37 mL) and the mixture was stirred at room temperature for 1 hour. After adding bromine (1 mL) thereto, the mixture was stirred at room temperature for 1 hour. The reaction mixture was concentrated in vacuo and the residue was diluted with diethylether and washed with a brine. The organic layer was dried over magnesium sulfate and filtered, and the filtrate was concentrated in vacuo to obtain ethyl 4-bromo-4-(4-chlorophenyl)-2-[(2-chlorophenyl)-hydrazono]-3-oxobutyrate (39 g, yield: 100%) as a solid.

MS (APCI) m/z; 457/459 M+H]$^+$ (4) To a solution of the compound obtained in the above step (3) (39 g) in ethanol/water (300 mL/100 mL) was added sodium acetate (35 g) and the mixture was stirred at 90° C. for 3 hours. After concentrating the reaction mixture, to the residue was added ethyl acetate and water and the mixture was stirred. The organic layer was washed with a brine, dried over magnesium sulfate and filtered. The filtrate was concentrated in vacuo and the resultant solid materials were washed with diisopropyl ether and ethanol to obtain 1-(2-chlorophenyl)-5-(4-chlorophenyl)-3-ethoxycarbonyl-4-hydroxy-1H-pyrazole (26 g, yield: 81%) as a powder.

MS (APCI) m/z; 377/379 M+H]$^+$ (5) To a solution of the compound obtained in the above step (4) (20 g) in dimethylformamide (150 mL) was added sodium hydride (2.54 g) under ice-cooling and the mixture was stirred at the same temperature for 30 minutes and at room temperature for 1 hour. To the reaction mixture was added methyl iodide (4.95 mL) and the mixture was stirred at room temperature for 1 hour. To the reaction mixture was added water and ethyl acetate and the mixture was stirred. The organic layer was washed with a brine, dried over magnesium sulfate and filtered. The filtrate was concentrated in vacuo and the resultant solid materials were washed with diisopropylether to give 1-(2-chlorophenyl)-5-(4-chlorophenyl)-3-ethoxycarbonyl-4-methoxy-1H-pyrazole (15.7 g, yield: 76%) as a powder.

MS (APCI) m/z; 391/393 M+H]$^+$ (6) To a solution of the compound obtained in the above step (5) (15.7 g) in ethanol (200 mL) was added an aqueous 2N sodium hydroxide solution (24 mL) under ice-cooling and the mixture was stirred at room temperature overnight. To the reaction mixture was added an aqueous 2N HCl solution (30 mL) and the mixture was stirred and concentrated. The resultant solid materials were collected by filtration and washed with water to give 3-carboxyl-1-(2-chlorophenyl)-5-(4-chlorophenyl)-4-methoxy-1H-pyrazole (14.4 g, yield: 99%) as a powder.

MS (APCI) m/z; 363/365 M+H]$^+$

Reference Example 2

To a solution of 1-(2-chlorophenyl)-5-(4-chlorophenyl)-3-ethoxycarbonyl-4-hydroxy-1H-pyrazole (200 mg, compound obtained in Reference Example 1 (4)) in tetrahydrofuran (4 mL) was added triphenylphosphine (208 mg) and 2-morpholino-ethanol (96 µL) and the mixture was stirred. Thereto was added dropwise diisopropyl azodicarboxylate (154 µL) at 0° C. under nitrogen-gas atmosphere and the mixture was stirred at room temperature overnight. The reaction mixture was concentrated in vacuo and the crude product was purified by column chromatography on silica gel (solvent: hexane/ethyl acetate=67/33 to 30/70) to obtain ethyl 1-(2-chlorophenyl)-5-(4-chlorophenyl)-3-ethoxycarbonyl-4-(2-morpholinoethoxy)-1H-pyrazole (463 mg, yield: 100%) as a colorless viscidity.

MS (APCI) m/z; 490/492 [M+H]$^+$

Reference Example 3

(1) The corresponding starting materials were treated in the same manner as described in Reference Example 1 (1) to (4) to give 5-(4-chlorophenyl)-1-(2,4-dichlorophenyl)-3-ethoxycarbonyl-4-hydroxy-1H-pyrazole (6.2 g).

MS (APCI) m/z; 411/413 [M+H]$^+$ (2) To a solution of the compound obtained in the above step (1) (1.1 g) in dimethylformamide (12 mL) was added sodium hydride (118 mg, 60% dispersion in mineral oil) under nitrogen-gas atmosphere and the mixture was stirred at the same temperature for 15 minutes. To the reaction mixture was added 2,2,2-trifluoroethyl trifluoromethanesulfonate (1.18 mL) and the mixture was stirred at 60° C. for 15 minutes. After cooling to room temperature, to the reaction mixture was added an aqueous citric acid and ethyl acetate. The mixture was extracted with ethyl acetate and the organic layer was dried over magnesium sulfate and filtered. The filtrate was concentrated in vacuo and the resultant crude product was purified by column chromatography on NH-silica gel (Chromatorex NH-silica gel, Fuji Silicia Chem., solvent: hexane/ethyl acetate =90/10 to 80/20) to obtain ethyl 5-(4-chlorophenyl)-1-(2,4-dichlorophenyl)- 3-ethoxycarbonyl-4-(2,2,2-trifluorethoxy)-1H-pyrazole (1.28 g, yield: 97%) as a colorless solid.

MS (APCI) m/z; 493/495 [M+H]$^+$

Reference Example 4

(1) The corresponding starting materials were treated in the same manner as described in Reference Example 1 (1) to (4) to obtain 1-(2-chlorophenyl)-3-ethoxycarbonyl-4-hydroxy-5-(4-trifluoromethylphenyl)-1H-pyrazole (40 g).

MS (APCI) m/z; 411/413 [M+H]$^+$ (2) To a solution of the compound obtained in the above step (1) (820 mg) in dimethylformamide (10 mL) was added chlorodifluoroacetic acid (1.30 g) and potassium carbonate (2.76 g) and the mixture was stirred at 80° C. for 2 days. After cooling to room temperature, to the reaction mixture was added a diluted aqueous HCl solution. After stirring, the mixture was extracted with chloroform and the extract was concentrated in vacuo. The residue was diluted with methanol (10 mL) and thereto was added an aqueous 1N sodium hydroxide solution (4 mL) at room temperature and the mixture was stirred at the same temperature overnight. To the reaction mixture was added a diluted aqueous HCl solution. After stirring, the mixture was extracted with chloroform and the extract was concentrated in vacuo. The resultant crude product was washed with methanol and dried to obtain 1-(2-chlorophenyl)-4-difluoromethoxy-3-ethoxycarbonyl-5-(4-trifluoromethylphenyl)-1H-pyrazole (504 mg, yield: 58%) as a colorless solid.

MS (APCI) m/z; 433/435 [M+H]$^+$

Reference Example 5

(1) To a solution of the compound obtained in Reference Example 1 (4) (1.39 g) in dimethylformamide (10 mL) was added sodium hydride (0.40 g, 60% dispersion in mineral oil) at room temperature and the mixture was stirred at the same temperature for 15 minutes. To the reaction mixture was added bromoacetonitrile (1.20 g) and the mixture was stirred at room temperature overnight. To the reaction mixture was added an aqueous citric acid and ethyl acetate. After stirring, the mixture was extracted with ethyl acetate and the organic layer was dried over magnesium sulfate and filtered. The filtrate was concentrated in vacuo and the resultant crude product was purified by column chromatography on silica gel (solvent: hexane/ethyl acetate=50/50 to 30/70) to obtain 1-(2-chlorophenyl)-5-(4-chlorophenyl)-3-ethoxycarbonyl-4-cyanomethoxy-1H-pyrazole (1.28 g, yield: 61%) as a white powder.

MS (APCI) m/z; 416/418 [M+H]$^+$ (2) To a solution of the compound obtained in the above step (1) in methanol (5 mL) was added an aqueous 1N sodium hydroxide (2 mL) under ice-cooling and the mixture was stirred at room temperature for 2 hours. The reaction mixture was added an aqueous 2N HCl solution (4 mL) and the mixture was extracted with chloroform. The organic layer was dried over magnesium sulfate and filtered. The filtrate was concentrated in vacuo to obtain 3-carboxy-1-(2-chlorophenyl)-5-(4-chlorophenyl)-4-(methoxycarbonyl)methoxy-1H-pyrazole (431 mg, yield: 99%) as a white powder.

MS (APCI) m/z; 421/423 [M+H]$^+$

Reference Example 6

To a solution of the compound obtained in Reference Example 1 (6) (363 mg) in toluene (30 mL) was added diphenylphosphorylazide (250 µL) and triethylamine (170 µL) at 0° C. under nitrogen-gas atmosphere and the mixture was stirred at the same temperature for 30 minutes and at 80° C. for 2 hours. To the reaction mixture was added an aqueous 6N HCl solution (1 mL) and the mixture was stirred at 100° C. overnight. After cooling to room temperature, to the reaction mixture was added an aqueous sodium hydrogencarbonate solution. After stirring, the mixture was extracted with chloroform and the extract was dried over magnesium sulfate and filtered. The filtrate was concentrated in vacuo and the resultant crude product was purified by column chromatography on silica gel (solvent: hexane/ethyl acetate=80/20 to 40/60) to obtain 3-amino-1-(2-chlorophenyl)-5-(4-chlorophenyl)-4-methoxy-1H-pyrazole (43 mg, yield: 50%) as a pale yellow solid.

MS (APCI) m/z; 334/336 [M+H]$^+$

Reference Example 7

To a solution of the compound obtained in Reference Example 1 (6) (2.5 g) in tetrahydrofuran (100 mL) was added dropwise methyl lithium (13.9 mL, 1.04 M ether solution) at 0° C. under nitrogen-gas atmosphere and the mixture was stirred at the same temperature for 30 minutes and at room temperature for 3 hours. To the reaction mixture was added water and ethyl acetate under ice-cooling and the mixture was stirred. The organic layer was washed with an aqueous sodium hydrogencarbonate solution, dried over magnesium sulfate and filtered. The filtrate was concentrated in vacuo and the resultant crude product was purified by column chromatography on silica gel (solvent: hexane/ethyl acetate=90/10 to 85/15) to obtain 3-acetyl-1-(2-chlorophenyl)-5-(4-chlorophenyl)-4-methoxy-1H-pyrazole (1.1 g, yield: 43%) as a pale yellow solid.

MS (APCI) m/z; 361/363 [M+H]$^+$

Reference Example 8

To a solution of 3-carboxy-1-(2-chlorophenyl)-5-(4-chlorophenyl)-4-methoxy-1H-pyrazole (1.09 g) in tetrahydrofuran (30 mL) was added dropwise methyl lithium (2.9 mL, 1.04 M diethylether solution) at −78° C. under nitrogen-gas atmosphere and the mixture was stirred at the same temperature for 30 minutes After warming to room temperature, to the reaction mixture was added dropwise vinylmagnesium bromide (7.7 mL, 0.97 M tetrahydrofuran solution) and the mixture was stirred at room temperature for 3 hours. To the reaction mixture was added water and an aqueous 1N HCl solution. After stirring, the mixture was extracted with ethyl acetate. The organic layer was dried over magnesium sulfate and filtered. The filtrate was concentrated in vacuo and the resultant crude product was purified by column chromatography on silica gel (solvent: hexane/ethyl acetate=90/10 to 85/15) to obtain 1-(2-chlorophenyl)-5-(4-chlorophenyl)-4-methoxy-3-vinylcarbonyl-1H-pyrazole (780 mg, yield: 70%) as a colorless solid.

MS (APCI) m/z; 373/375 [M+H]$^+$

Reference Example 9

(1) To a solution of 3-carboxy-1-(2-chlorophenyl)-5-(4-chlorophenyl)-4-methoxy-1H-pyrazole (3.63 g) in toluene (30 mL) was added diphenylphosphorylazide (2.37 mL) and triethylamine (1.67 mL) at 0° C. under nitrogen-gas atmosphere and the mixture was stirred at the same temperature for 30 minutes and at 80° C. for 3 hours. After cooling to 0° C., to the reaction mixture was added benzyl alcohol (1.86 mL) and 4-dimethylaminopyridine (61 mg) and the mixture was stirred at 80° C. overnight. After cooling to room temperature, to the reaction mixture was added an aqueous sodium hydrogencarbonate solution. After stirring, the mixture was extracted with ethyl acetate and the extract was dried over magnesium sulfate and filtered. The filtrate was concentrated in vacuo and the resultant crude product was purified by column chromatography on silica gel (solvent: hexane/ethyl acetate=80/20 to 60/40) to obtain 3-benzyloxycarbonylamino-1-(2-chlorophenyl)-5-(4-chlorophenyl)-4-methoxy-1H-pyrazole (4.15 g, yield: 89%) as a pale yellow viscidity.

MS (APCI) m/z; 468/470 [M+H]$^+$ (2) To a solution of the compound obtained in the above step (1) (4.1 g) in methanol (50 mL) was added 10% palladium-carbon (400 mg) and the mixture was stirred at room temperature under hydrogen-gas atmosphere for 7 hours. The reaction mixture was filtered and the filtrate was concentrated in vacuo. To the residue was added chloroform and an aqueous sodium hydrogencarbonate solution. After stirring, the mixture was extracted with chloroform and the extract was dried over magnesium sulfate and filtered. The filtrate was concentrated in vacuo and the resultant crude product was recrystallized from ethanol and resultant precipitated colorless materials were removed by filtration. The filtrate was concentrated in vacuo and the resultant crude product was purified by column chromatography on silica gel (solvent: hexane/ethyl acetate=70/30 to 50/50) to obtain 3-amino-1-(2-chlorophenyl)-5-(4-chlorophenyl)-4-methoxy-1H-pyrazole (310 mg, yield: 11%) as a pale yellow solid.

MS (APCI) m/z; 334/336 [M+H]$^+$

Reference Example 10

(1) To a solution of 1-benzyloxycarbonyl-4-hydroxypiperidine (1.3 g) in dimethylformamide (10 mL) was added sodium hydride (360 mL) under ice cooling and the mixture was stirred at room temperature under nitrogen-gas atmosphere for 1 hours. To the reaction mixture was added methyl iodide (374 µL) under ice-cooling and the mixture was stirred at the same temperature for 1 hour and at room temperature for 2 hours. To the reaction mixture was added water and ethyl acetate and the mixture was stirred. The organic layer washed with a brine, dried over magnesium sulfate and filtered. The filtrate was concentrated in vacuo and the resultant crude product was purified by column chromatography on silica gel (solvent: hexane/ethyl acetate=88/12 to 70/30) to obtain 1-benzyloxycarbonyl-4-methoxypiperidine (622 mg, yield: 45%) as a pale yellow oil.

MS (APCI) m/z; 250 [M+H]$^+$ (2) To a solution of the compound obtained in the above step (1) (620 mg) in methanol (20 mL) was added 10% palladium-carbon (80 mg) and the mixture was stirred at room temperature under hydrogen-gas atmosphere for 3 hours. The reaction mixture was filtered by a membrane filter and the filtrate was concentrated in vacuo to obtain 4-methoxypiperidine (290 mg, yield: 100%) as a pale yellow oil.

MS (APCI) m/z; 116 [M+H]$^+$

Reference Example 11

(1) To a solution of 1-benzyl-4-aminopiperidine (57.1 g) in methylene chloride (300 mL) was added tert-butyl dicarboxylate (68.8 g) under ice-cooling and the mixture was stirred at room temperature for 3 days. The reaction mixture was concentrated in vacuo and to the residue was added ethyl acetate and an aqueous sodium hydrogencarbonate solution. The mixture was stirred and the organic layer was washed with a brine, dried over magnesium sulfate and filtered. The filtrate was concentrated in vacuo and the resultant crude crystals were washed with diisopropylether and collected by filtration. The filtrate was concentrated in vacuo and the resultant crude crystals were washed with diisopropylether and collected by filtration. The crude crystals were combined and dried to obtain 1-benzyl-4-(tert-butoxycarbonyl)aminopiperidine (83.2 g, yield: 96%) as a pale yellow solid.

MS (APCI) m/z; 291 [M+H]$^+$ (2) To a solution of the compound obtained in the above step (1) (72.6 g) in methanol (350 mL) was added 20% palladium-carbon (17.5 g) and the mixture was stirred at room temperature under hydrogen-gas atmosphere overnight. The reaction mixture was filtered by a membrane filter and the filtrate was concentrated in vacuo to obtain 4-(tert-butoxycarbonyl)aminopiperidine (48.3 g, yield: 96%) as a pale yellow solid.

MS (APCI) m/z; 201 [M+H]$^+$ (3) To a solution of the compound obtained in the above step (2) (5.0 g) in methylene chloride (50 mL) was added triethylamine (5.23 mL) and thereto was added ethanesulfonyl chloride (2.36 mL) under ice-cooling. The mixture was stirred at the same temperature for 30 minutes. After warming to room temperature, the reaction mixture was concentrated in vacuo and to the residue was added chloroform and an aqueous sodium hydrogencarbonate solution. After stirring, the organic layer was dried over magnesium sulfate and filtered. The filtrate was concentrated in vacuo and the resultant crystals were recrystallized from diisopropylether to obtain 4-tert-butoxycarbonyl)amino-1-ethanesulfonylpiperidine (6.99 g, yield: 96%) as a pale yellow solid.

MS (APCI) m/z; 291 [M+H]$^+$ (4) To the compound obtained in the above step (3) (6.8 g) was added 4N HCl-dioxane (23.3 mL) and methanol (5 mL) and the mixture was stirred at room temperature overnight. To the reaction mixture was neutralized by adding tetrahydrofuran and an aqueous 2N sodium hydroxide solution. The mixture was saturated with potassium carbonate and extracted with tetrahydrofuran. The extract was dried over magnesium sulfate and filtered. The filtrate was concentrated in vacuo and the residue was dissolved in tert-butyl alcohol and lyophilized to obtain 4-amino-1-ethanesulfonylpiperidine (4.20 g, yield: 94%) as a pale red powder.

MS (APCI) m/z; 193 [M+H]$^+$

Reference Example 12

(1) To a solution of 4-tetrahydrothiopyranone (2.32 g) in ethanol (100 mL) was added sodium acetate (3.28 g) and hydroxylamine hydrochloride (1.81 g) at room temperature and the mixture was stirred at the same temperature for 2 hours. The reaction mixture was concentrated in vacuo and to the residue was added ethyl acetate and an aqueous sodium hydrogencarbonate solution. After stirring, the mixture was extracted with ethyl acetate and the organic layer was washed with a brine, dried over sodium sulfate and filtered. The filtrate was concentrated in vacuo to obtain 4-tetrahydrothiopyrane oxime (2.53 g, yield: 96%) as a colorless solid.

MS (APCI) m/z; 132 [M+H]$^+$ (2) To a solution of the compound obtained in the above step (1) (500 mg) in diethylether (10 mL) was added lithium aluminum hydride (289 mg) under ice-cooling and nitrogen-gas atmosphere and the mixture was stirred at the same temperature for 30 minutes and at room temperature for 1 hour. To the reaction mixture was added lithium aluminum hydride (72 mg) and the mixture was stirred at 40° C. for 2 hours. To the reaction mixture was added water (1 mL) and an aqueous 2N sodium hydroxide solution (1 mL) at room temperature. After stirring, the mixture was filtered through Celite and the filtrate was concentrated in vacuo to obtain 4-tetrahydrothiopyranylamine (150 mg, yield: 34%) as a yellow fluid.

MS (APCI) m/z; 118 [M+H]$^+$

Reference Example 13

To a solution of 4-nitrosothiomorpholine (17.6 g) i in water (5 mL) was added an aqueous 20% titanium trichloride solution (413 mL) and the mixture was stirred at room temperature for 3.5 hours. To the reaction mixture was added potassium carbonate to basify and the mixture was filtered. To the filtrate was added chloroform and the mixture was stirred. The organic layer was washed with a brine, dried over magnesium sulfate and filtered. The filtrate was concentrated in vacuo to obtain 4-aminothiomorpholine (10.14 g, yield: 64.5%) as a pale yellow viscosity. To a solution of the product (7.57 g) in chloroform (10 mL) was added 4N HCl-dioxane (17.6 mL) and the mixture was stirred. The reaction mixture was concentrated in vacuo and the resultant crystals were washed with diisopropyl ether-hexane and dried to give 4-aminothiomorpholine hydrochloride (6.3 g, yield: 63.6%) as a powder.

MS (APCI) m/z; 119 [M−HCl]$^+$

Reference Example 14

(1) To a solution of 4,4-difluoropiperidine hydrochloride (2.0 g) in water (32 mL) was added an aqueous 2N sodium hydroxide solution (7.6 mL) and the mixture was stirred at room temperature for 1 hours. To the reaction mixture was added sodium nitrite (1.75 g) and thereto was added acetic acid (1.27 mL) under ice-cooling. The mixture was stirred at room temperature for 2 hours. To the reaction mixture was added an aqueous sodium hydrogencarbonate solution and the mixture was stirred and extracted with chloroform. The extract was dried over magnesium sulfate and filtered. The filtrate was concentrated in vacuo and the resultant crude product was purified by column chromatography on silica gel (solvent: hexane/ethyl acetate=4/1) to obtain 4,4-difluoro-1-nitrosopiperidine (1.89 g, yield: 99%) as a pale yellow solid.

MS (APCI) m/z; 151 [M+H]$^+$ (2) To a solution of the compound obtained in the above step (1) (1.89 g) in tetrahydrofuran was gradually added lithium aluminum hydride (837 mg) under ice-cooling and the mixture was refluxed under heating for 1 hour. To the reaction mixture was added water under ice-cooling and the mixture was refluxed under heating for 30 minutes. After cooling to room temperature, the reaction mixture was filtered through Celite. The filtrate was concentrated in vacuo and to the residue was added an aqueous sodium hydrogencarbonate solution and chloroform. After stirring, the organic layer was dried over sodium sulfate and filtered. The filtrate was concentrated in vacuo to obtain 1-amino-4,4-difluoropiperidine (500 mg, yield: 29%) as a pale yellow oil.

MS (APCI) m/z; 137 [M+H]$^+$

Reference Example 15

To a solution of the compound obtained in Reference Example 9 (1) (1.9 g) in acetic acid (10 mL) was added an aqueous hydrogen bromide solution (10 mL) and the mixture was stirred at 80° C. for 2 hours. To the reaction mixture was added an aqueous 2N sodium hydroxide solution (130 mL) and the mixture was stirred and extracted with chloroform. The extract was dried over magnesium sulfate and filtered. The filtrate was concentrated in vacuo and the resultant crude product was purified successively by column chromatography on silica gel (solvent: hexane/ethyl acetate=70/30 to 0/100) and column chromatography on NH— silica gel (Chromatorex NH-silica gel, Fuji Silicia Chem., solvent: hexane/ethyl acetate=70/30 to 60/40) to obtain 3-amino-1-(2-chlorophenyl)-5-(4-chlorophenyl)-4-methoxy-1H-pyrazole (353 mg, yield: 26%) as a pale yellow solid.

MS (APCI) m/z; 334/336 [M+H]$^+$

Reference Example 16

(1) To a solution of 4-tert-butoxycarbonylpiperazine (1.3 g) in methylene chloride (50 mL) was added 4-tert-butyl nitrite (3.5 mL) and the mixture was refluxed under heating overnight. The reaction mixture was concentrated in vacuo and the resultant crude product was purified by column chromatography on silica gel (solvent: hexane/ethyl acetate=4/1 to 2/1) to obtain 4-tert-butoxycarbonyl-1-nitrosopiperazine (758 mg, yield: 50%) as a yellow solid.

MS (APCI) m/z; 216 [M+H]$^+$ (2) To a solution of the compound obtained in the above step (1) (730 mg) in methanol (10 mL) was added zinc powder (1.1 g) at room temperature and thereto was added dropwise acetic acid (10 mL) under ice-cooling and the mixture was stirred at room temperature for 2 hours. The reaction mixture was filtered and to the filtrate was added an aqueous sodium hydrogencarbonate solution to basify. After stirring, the mixture was extracted with chloroform. The organic layer was dried over sodium sulfate and filtered. The filtrate was concentrated in vacuo to obtain 1-amino-4-tert-butoxycarbonylpiperazine (730 mg, yield: 100%) as a pale yellow oil.

Reference Example 17

The compound obtained in Reference Example 3 (1) was treated in the same manner as described in Reference Example 1 (5) to (6) to obtain 3-carboxy-1-(2,4-dichlorophenyl)-5-(4-chlorophenyl)-4-methoxy-1H-pyrazole (2.8, yield: 89% g) as a solid.

MS (APCI) m/z; 397/399 [M+H]$^+$

Reference Example 18

The compound obtained in Reference Example 1 (4) (321 mg) and tetrahydrothiopyran-4-ol were treated in the same manner as described in Reference Example 2 to obtain 1-(2-chlorophenyl)-5-(4-chlorophenyl)-3-ethoxycarbonyl-4-(4-tetrahydrothiopyranyl)oxy-1H-pyrazole and then treating the product in the same manner as described in Reference Example 1 (6) to obtain 3-carboxy-1-(2-chlorophenyl)-5-(4-chlorophenyl)-4-(4-tetrahydrothiopyranyl)oxy-1H-pyrazole (351 mg, yield: 87% g) as a solid.

MS (APCI) m/z; 449/451 [M+H]$^+$

Reference Example 19

The corresponding starting materials were treated in the same manner as described in Reference Example 1 to obtain 1,5-bis(4-chlorophenyl)-4-methoxy-1H-pyrazole-3-carboxylic acid (3.0 g, yield: 67% g) as a solid.

MS (APCI) m/z; 363/365 [M+H]$^+$

Reference Examples 20 to 43

The corresponding starting materials were treated in the same manner as described in either one of Reference Examples 1 to 5 to obtain the compounds as shown

TABLE B1

(No. 1)

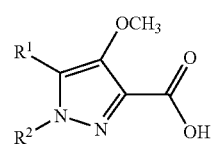

| Ref. Ex. Nos. | $R^1$ | $R^2$ | Physicochemical properties etc. |
|---|---|---|---|
| 20 | F-⟨⟩- | 2-Cl-C₆H₄- | solid<br>MS(APCI): 347/349 [M + H]$^+$ |
| 21 | Cl-⟨⟩- | 2-Cl-4-F-C₆H₃- | solid<br>MS(APCI): 381/383 [M + H]$^+$ |

TABLE B1-continued

| Ref. Ex. Nos. | R¹ | R² | Physicochemical properties etc. |
|---|---|---|---|
| 22 | H₃CO—⟨C₆H₄⟩— | 2-Cl-C₆H₄— | solid MS(APCI): 359/361 [M + H]⁺ |
| 23 | Cl—⟨C₆H₄⟩— | 2-CF₃-C₆H₄— | solid MS(APCI): 397/399 [M + H]⁺ |
| 24 | Cl—⟨C₆H₄⟩— | 2-CN-C₆H₄— | solid MS(APCI): 354/356 [M + H]⁺ |
| 25 | Cl—⟨C₆H₄⟩— | 2-F-C₆H₄— | solid MS(APCI): 347/349 [M + H]⁺ |
| 26 | NC—⟨C₆H₄⟩— | 2-Cl-C₆H₄— | solid MS(APCI): 354/356 [M + H]⁺ |

(No. 2)

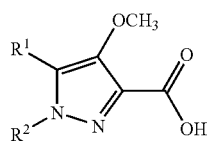

| Ref. Ex. Nos. | R¹ | R² | Physicochemical properties etc. |
|---|---|---|---|
| 27 | F₃C—⟨C₆H₄⟩— | 2,4-Cl₂-C₆H₃— | solid MS(ESI): 429/431 [M − H]⁻ |
| 28 | F₃C—⟨C₆H₄⟩— | 2-Cl-4-F-C₆H₃— | solid MS(ESI): 413/415 [M − H]⁻ |
| 29 | Cl—⟨C₆H₄⟩— | 2-OCH₃-C₆H₄— | solid MS(APCI): 359/361 [M + H]⁺ |
| 30 | H₃CO₂S—⟨C₆H₄⟩— | 2-Cl-C₆H₄— | solid MS(APCI): 407/409 [M + H]⁺ |

TABLE B1-continued (No. 3)

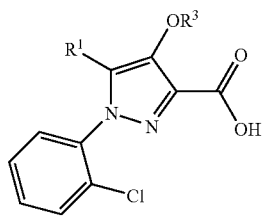

| Ref. Ex. Nos. | R¹ | R³ | Physicochemical properties etc. |
|---|---|---|---|
| 31 | 4-Cl-C₆H₄— | tetrahydropyran-4-yl | solid<br>MS(APCI): 433/435 [M + H]⁺ |
| 32 | 4-Cl-C₆H₄— | —(CH₂)₂SCH₃ | powder<br>MS(APCI): 423/425 [M + H]⁺ |
| 33 | 4-F₃C-C₆H₄— | —CHF₂ | powder<br>MS(APCI): 433/435 [M + H]⁺ |
| 34 | 4-Cl-C₆H₄— | —C₂H₅ | solid<br>MS(APCI): 377/379 [M + H]⁺ |
| 35 | 4-F₃C-C₆H₄— | —C₂H₅ | solid<br>MS(APCI): 411/413 [M + H]⁺ |
| 36 | 4-Cl-C₆H₄— | —(CH₂)₂OCH₃ | solid<br>MS(APCI): 407/409 [M + H]⁺ |
| 37 | 4-F₃C-C₆H₄— | —(CH₂)₂OCH₃ | solid<br>MS(APCI): 441/443 [M + H]⁺ |
| 38 | 4-Cl-C₆H₄— | —C₃H₇ | solid<br>MS(APCI): 391/393 [M + H]⁺ |

TABLE B1-continued (No. 4)

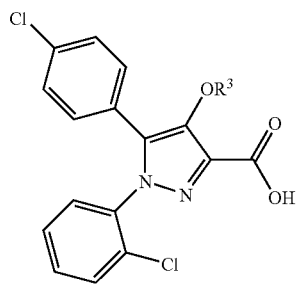

| Ref. Ex. Nos. | R³ | Physicochemical properties etc. |
|---|---|---|
| 39 | —S(=O)₂—N(CH₃)₂ | solid<br>MS(APCI): 456/458 [M + H]⁺ |
| 40 | —CHF₂ | Each compound was used as a starting material without further purification in the following step. |
| 41 | ethyl-thiazolyl | |
| 42 | 3,5-dimethyl-4-ethyl-isoxazolyl | |
| 43 | 3-ethyl-5-methyl-isoxazolyl | |

Reference Example 44

A solution of 1-aminocyclohexanecarboxylic acid (600 mg) in tetrahydrofuran-methanol was stirred under ice-cooling. Thereto was added dropwise a (trimethylsilyl) diazomethane solution (4.2 mL) and the mixture was stirred overnight. The reaction mixture was concentrated in vacuo and to the residue was added diethyl ether-hexane (1/1). Thereto was added 4M HCl-ethyl acetate (1.05 mL) and the precipitates were collected by filtration and dried to give 1-amino-1-methoxy-carbonylcyclohexane (423 mg, yield: 52%) as a white powder.

MS (APCI) m/z; 158 [M+H]⁺

Reference Example 45

(1) To a solution of potassium cyanide (5.6 g) and ammonium chloride (5.06 g) in water (17 mL) was added a solution of tetrahydrothiopyran-4-one (10 g) in methanol (22 mL) and the mixture was refluxed under heating overnight. After cooling to room temperature, to the reaction mixture was added an aqueous 1N sodium hydroxide solution. The mixture was extracted with diethyl ether and the organic layer was dried over magnesium sulfate and filtered. The filtrate was concentrated in vacuo and to a solution of the residue in diethyl ether was added 4N HCl-ethyl acetate. The precipitates were collected by filtration to give 4-amino-4-cyano-tetrahydrothiopyrane hydrochloride (13.6 g, yield: 88%) as a colorless solid.

MS (ESI) m/z; 143 [M+H]⁺

(2) A solution of the compound obtained in the above step (1) (10.5 g) in an aqueous 6N HCl solution (500 mL) was refluxed under heating overnight. After cooling to room temperature, the reaction mixture was concentrated in vacuo. The residue was dried to give 4-amino-tetrahydrothiopyran-4-carboxylate hydrochloride (10.6 g) as a crude product.

MS (ESI) m/z; 162 [M+H]⁺

(3) To a solution of the compound obtained in the above step (2) (10.6 g) in methanol (70 mL) was added dropwise thionyl chloride (5.7 mL) gradually and the mixture was refluxed under heating overnight. After cooling to room temperature, the reaction mixture was concentrated in vacuo. The residue was washed with ethyl acetate-diethyl ether and thereto was added an aqueous 1N sodium hydroxide solution. The mixture was extracted with chloroform and the organic layer was dried over magnesium sulfate and filtered. The filtrate was concentrated in vacuo to give 4-amino-4-methoxycarbonyl-tetrahydrothiopyrane (3.83 g, yield: 39%) as a brown oil.

MS (ESI) m/z; 176 [M+H]$^+$ (4) To a solution of the compound obtained in the above step (3) (100 mg) in methylene chloride (4 mL) was added m-chloroperbenzoic acid (394 mg) gradually and the mixture was stirred at room temperature for 30 minutes. To the reaction mixture was added methanol (4 mL) and then added PL-HCO$_3$ MP resin (0.9 g) gradually and the mixture was stirred overnight. The reaction mixture was filtered and the filtrate was concentrated in vacuo. The resultant crude product was purified by column chromatography on silica gel (solvent: hexane/ethyl acetate=30/70 to 0/100) to obtain 4-amino-4-methoxycarbonyl-1,1-dioxotetrahydrothiopyrane (38 mg, yield: 32%) as a colorless solid.

MS (ESI) m/z; 208 [M+H]$^+$

Reference Example 46

The corresponding materials were treated in the same manner as described in Reference Example 45(1) to (3) to give 4-amino-4-methoxycarbonyltetrahydropyrane as white crystals.

MS (ESI) m/z; 160 [M+H]$^+$

Reference Example 47

(1) To a solution of 1-tert-butoxycarbonyl-4-carboxy-4-phenylpiperidine (1.53 g) in tetrahydrofuran (2 mL)-methanol (2 mL) was added dropwise 2N (trimethylsilyl)diazomehane-diethyl ether solution (8.8 mL) at room temperature and the mixture was stirred at the same temperature for 3 hours. To the reaction mixture was added an aqueous saturated sodium hydrogencarbonate solution and the mixture was stirred and extracted with chloroform. The extract was dried over magnesium sulfate and filtered. The filtrate was concentrated in vacuo and the resultant crude product was purified by column chromatography on silica gel (solvent: hexane/ethyl acetate=90/10 to 85/15) to obtain 1-tert-butoxycarbonyl-4-methoxycarbonyl-4-phenylpiperidine (1.31 g, yield: 82%) as a colorless solid.

MS (APCI) m/z; 220 [M+H]$^+$ (2) To a solution of the compound obtained in the above step (1) in dioxane (2 mL) was added 4N HCl-dioxane (3 mL) and the mixture was stirred at room temperature for 1 hour. To the reaction mixture was further added 4N HCl-dioxane (2 mL) and the mixture was stirred at room temperature for 2 hours. To the reaction mixture was added an aqueous saturated sodium hydrogencarbonate solution under ice-cooling and the mixture was stirred and extracted with chloroform. The extract was dried over magnesium sulfate and filtered. The filtrate was concentrated in vacuo and to the residue was added water (5 mL), sodium nitrite (276 mg) and acetic acid (172 µL) and the mixture was stirred at room temperature overnight. To the reaction mixture was added an aqueous saturated sodium hydrogencarbonate solution and the mixture was stirred and extracted with chloroform. The extract was concentrated in vacuo and the resultant crude product was purified by column chromatography on silica gel (solvent: hexane/ethyl acetate=85/15 to 75/25) and the resultant product was diluted with methanol (3 mL). Thereto was added zinc powder (654 mg) and then added dropwise acetic acid (3 mL) under ice-cooling and the mixture was stirred at room temperature for 2 hours. The reaction mixture was filtered and to the filtrate was added an aqueous saturated sodium hydrogencarbonate solution. After stirring, the mixture was extracted with chloroform and the extract was dried over magnesium sulfate and filtered. The filtrate was concentrated in vacuo to obtain 1-amino-4-methoxycarbonyl-4-phenylpiperidine (389 mg, yield: 83%) as a colorless solid.

MS (APCI) m/z; 235 [M+H]$^+$

Reference Example 48

To a solution of 4-ethoxycarbonyl-4-benzylpiperidine (495 mg) in water (5 mL) was added sodium nitrite (276 mg) and acetic acid (201 µL) and the mixture was stirred at room temperature overnight. To the reaction mixture was added an aqueous saturated sodium hydrogencarbonate solution and the mixture was stirred and extracted with chloroform. The extract was concentrated in vacuo and the resultant crude product was purified by column chromatography on silica gel (solvent: hexane/ethyl acetate=85/15 to 80/20) and dried in vacuo to give 4-ethoxycarbonyl-4-benzyl-1-nitrosopiperidine (565 mg, yield: 100%) as a colorless solid. To a solution of the product (565 mg) in methanol (3 mL) was added zinc powder (654 mg) and then added acetic acid (3 mL) under ice-cooling and the mixture was stirred at room temperature for 3 hours. The reaction mixture was filtered and the filtrate was concentrated in vacuo. To the residue was added an aqueous saturated sodium hydrogencarbonate solution and chloroform and the mixture was stirred and extracted with chloroform. The extract was dried over magnesium sulfate and filtered. The filtrate was concentrated in vacuo to give 1-amino-4-benzyl-4-ethoxycarbonylpiperidine (508 mg, yield: 97%) as a colorless viscosity.

MS (APCI) m/z; 263 [M+H]$^+$

Reference Example 49

The compound obtained in Reference Example 4(1) was treated in the same manner as described in Reference Example 1(5) to (6) to give 3-carboxy-1-(2-chlorophenyl)-5-(4-trifluoromethylphenyl)-4-methoxy-1H-pyrazole (4.1 g, yield: 85%) as a colorless solid.

MS (APCI) m/z; 397/399 [M+H]$^+$

Reference Examples 50 to 52

The corresponding materials were treated in the same manner as described in Reference Example 1(1) to (4) and then the resultant product was treated in the same manner as described in Reference Example 4(2) to give the compounds as shown in the following Table B2.

TABLE B2

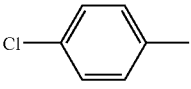

| Ref. Ex. Nos. | R$^1$ | R$^2$ | Physico-chemical properties etc. |
|---|---|---|---|
| 50 | 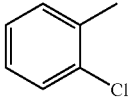 | | white solid MS(APCI): 399/401 [M + H]$^+$ |

TABLE B2-continued

[Structure: pyrazole with R¹ at 5-position, R² on N, OCHF₂ at 4-position, and C(=O)OH at 3-position]

| Ref. Ex. Nos. | R¹ | R² | Physico-chemical properties etc. |
|---|---|---|---|
| 51 | F₃C—⟨C₆H₄⟩— | 2,4-dichlorobenzyl (Cl, Cl) | white solid MS(APCI): 467/469 [M + H]⁺ |
| 52 | F₃C—⟨C₆H₄⟩— | 4-fluoro-2-chlorobenzyl (F, Cl) | pale yellow solid MS(APCI): 451/453 [M + H]⁺ |

Reference Examples 53

(1) To a solution of 1-benzylpiperidin-4-one (5.69 g) in ethanol (4.2 mL) was added dropwise a solution of ethylamine hydrochloride (2.69 g) in water (3 mL) under ice-cooling and then added dropwise a solution of potassium cyanide (2.04 g) in water (7 mL) and the mixture was stirred at room temperature overnight. To the reaction mixture was added isopropyl alcohol (10 mL) and water (30 mL) and the mixture was stirred and extracted. To the organic layer was added water (30 mL) and the mixture was stirred and extracted. The organic layer was diluted with methylene chloride (30 mL) and the mixture was washed with a brine, dried over magnesium sulfate and filtered. The filtrate was concentrated in vacuo and to the residue was added isopropyl alcohol (100 mL) and the precipitates were filtered off. The filtrate was concentrated in vacuo to give 1-benzyl-4-cyano-4-(ethylamino)piperidine (7.3 g, yield: 99.7%) as a yellow oil.

MS (APCI) m/z; 244 [M+H]⁺

(2) To a solution of the compound obtained in the above step (1) (1.38 g) in methylene chloride (4.8 mL) was added dropwise concentrated sulfuric acid (4.3 mL) over a period of 20 minutes under ice-cooling and the mixture was stirred at room temperature overnight. The organic layer was extracted from the reaction mixture and thereto was added dropwise an aqueous 28% ammonia under ice-cooling (18 mL) over a period of 1 hour. To the reaction mixture was added water (12 mL) and the mixture was extracted with methylene chloride. The organic layer was washed with a brine, dried over magnesium sulfate and filtered. The filtrate was concentrated in vacuo to give 1-benzyl-4-carbamoyl-4-(ethylamino)piperidine (1.44 g, yield: 97%) as a pale yellow solid.

MS (APCI) m/z; 262 [M+H]⁺

(3) To a solution of the compound obtained in the above step (2) (1.4 g) in methanol (19 mL) was added 20% palladium hydroxide-carbon and the mixture was stirred at room temperature under hydrogen-gas atmosphere overnight. The reaction mixture was filtered through Celite and the filtrate was concentrated in vacuo. To the concentrated solution was added isopropyl ether (30 mL) and the precipitated crystals were collected by filtration and dried to give 4-carbamoyl-4-ethylaminopiperidine (0.84 g, yield: 91%) as a pale yellow solid.

MS (APCI) m/z; 172 [M+H]⁺

Experiment 1

[Human CB1 Receptor Binding Assay]

(1) Preparation of human CB1 receptor (membrane fraction):

Materials)

Human CB1-expressing cell line: hCB1/CHO#C3 (Euroscreen)

Medium: F-12 (GIBCO#11765-062), 10% fetal calf serum, antibiotics (400 □g, Geneticin (GIBCO# 11811-031)

Buffer A: 50 mM tris-HCl (pH 7.5) containing ethylenediaminetetraacetic acid (2.5 mM), $MgCl_2$ (5 mM) and sucrose (200 mM)

Procedure)

The receptor-expressing cells cultivated in the above medium were washed with phosphate buffer (×2) and thereto was added Buffer A (2 mL) under ice-cooling or 4° C. (the following procedures were also carried out at the same temperature). The cells were collected by using a cell-scraper, treated by a microtip-type ultrasonicator for 20 seconds (pulse-on: 2 sec, pulse-off: 1 sec) and centrifuged (500×g, 15 min). The supernatant was separated and centrifuged (43000×g, 60 min). The resultant pellet was suspended in Buffer A and homogenized with a potter-type homogenizer. To the homogenate was added an equal volume of 80% glycerol and stored at −80° C.

(2) Procedure of CB1 Receptor Binding Assay:

Materials)

Buffer B: 50 mM tris-HCl (pH 7.5) containing ethylenediaminetetraacetic acid (2.5 mM), $MgCl_2$ (5 mM) and bovine serum albumine (2 mg/mL, fatty acid-free, SIGMA-A7030)

Buffer C: 50 mM tris-HCl (pH 7.5) containing ethylenediaminetetraacetic acid (2.5 mM), $MgCl_2$ (5 mM) and bovine serum albumine (2 mg/mL, SIGMA-A7906)

Coating solution: 0.3% ethyleneimine polymer

Radioligand: [³H]-CP55940 (30 nM/7992 dpm/μL) prepared by diluting 8.3 □M solution of the radioligand with Buffer B Method)

Each well of the assay plate (96-well, Costar Code#3371) was filled with Buffer B (140 μL), a solution of each test compound in dimethylsulfoxide (20 μL, final concentration: 0.1%), radioligand (20 μL) and membrane preparation (20 μL, 0.5 □g/20 μL) and the mixture was incubated at 30° C. for 90 minutes to proceed the binding reaction. The reaction mixture was harvested to each well of a plate presoaked with the above coating solution (Packard Unifilter GF/B, #6005177). The plate was washed with Buffer C (200 μL×10) and dried at 50° C. for 1 hour and Microscinti 40 (40 μL) was added to each well. The bound radiolabel was quantitated by scintilation counting (Top Count NXT, Packard). $IC_{50}$ value of each test compound against the radioligand-binding to CB1 receptors was calculated on the basis of the quantitated radiolabel activity by using Graphpad Prism 3.02.

3) Results:

$IC_{50}$ value of each test compound is shown in the following Table C1. Meanwhile, the symbols (+, ++ and +++) are defined as follows:

+: 100 nM<$IC_{50}$<500 nM
++: 10 nM<$IC_{50}$<100 nM
+++: 10 nM>$IC_{50}$

TABLE C1

| Test Compounds | $IC_{50}$ (nM) |
|---|---|
| Compound of Example 4 | ++ |
| Compound of Example 36 | ++ |
| Compound of Example 54 | ++ |

TABLE C1-continued

| Test Compounds | IC$_{50}$ (nM) |
|---|---|
| Compound of Example 55 | ++ |
| Compound of Example 18 | ++ |
| Compound of Example 134 | ++ |
| Compound of Example 148 | ++ |
| Compound of Example 216 | ++ |
| Compound of Example 276 | ++ |
| Compound of Example 279 | ++ |
| Compound of Example 288 | + |
| Compound of Example 307 | +++ |
| Compound of Example 339 | ++ |

INDUSTRIAL APPLICABILITY

The compounds [I] of the present invention are useful for treatment and/or prophylaxis of various CB1 receptor-mediated diseases such as psychosis including schizophrenia. The compounds [I] of the present invention are also useful for withdrawal from a chronic treatment, alcohol dependence or drug abuse. Furthermore, the compounds [I] of the present invention are useful as an agent for enhancing analgesic activity or an agent for smoking cessation.

The invention claimed is:

1. A pyrazole compound of the formula [I]:

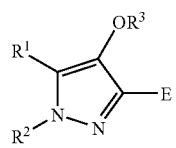

wherein
R$^1$ is a phenyl group substituted by one to two groups selected from a halogen atom and a trihalogeno-C$_{1-4}$ alkyl group,
R$^2$ is a phenyl group substituted by one to two halogen atoms,
R$^3$ is a C$_{1-4}$ alkyloxy-C$_{1-4}$ alkyl group or an alkyl group optionally substituted by one to three halogen atoms,
E is a group of the following formula:

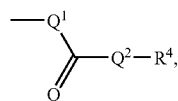

Q$^1$ is a single bond,
Q$^2$ is a single bond or a C$_{1-4}$ alkylene group,
R$^4$ is a saturated or unsaturated 5- to 6-membered heteromonocyclic group optionally substituted by one to three groups selected from an oxo group or a group of the formula: —NH(R$^6$), and
R$^6$ is (i) a saturated or unsaturated 5- to 7-membered heteromonocyclic group optionally substituted by one to three groups selected from the group consisting of a halogen atom, a C$_{1-4}$ alkyl group optionally substituted by one to three halogen atoms, a phenyl group optionally substituted by one to two halogen atoms, and an acyl group or (ii) an amino group optionally substituted by one to two C$_{1-4}$ alkyl groups,
or a pharmaceutically acceptable salt thereof.

2. The compound according to claim 1 in which
R$^1$ is a phenyl group substituted by a group selected from a chlorine atom and a trifluoro-C$_{1-3}$ alkyl group,
R$^2$ is a phenyl group substituted by one to two group(s) selected from a chlorine atom or a fluorine atom,
R$^3$ is a C$_{1-4}$ alkyl group optionally substituted by one to three group(s) selected from a fluorine atom or a C$_{1-4}$ alkyloxy group,
R$^4$ is (i) an unsaturated 5- to 6-membered heteromonocyclic group optionally substituted by one to two oxo group(s) or (ii) a group of the formula: —NH(R$^6$),
R$^6$ is (i) a saturated or unsaturated 5- to 6-membered heteromonocyclic group optionally substituted by one to three group(s) selected from (a) a fluorine atom, (b) a C$_{1-3}$ alkyl group optionally substituted by one to three fluorine atom(s), (c) a benzoyl group optionally substituted by one to two group(s) selected from a chlorine atom and a fluorine atom, and (d) a phenyl group optionally substituted by one to two group(s) selected from a chlorine atom and a fluorine atom or (ii) a di(C$_{1-3}$ alkyl) amino group.

3. A compound selected from the group consisting of:
1-(2-chlorophenyl)-5-(4-chlorophenyl)-4-methoxy-3-[N-(1-azacycloheptyl)-carbamoyl]-1H-pyrazole;
1-(2-chlorophenyl)-5-(4-chlorophenyl)-4-methoxy-3-[N-(4-tetrahydropyranyl)-carbamoyl]-1H-pyrazole;
1-(2-chlorophenyl)-5-(4-chlorophenyl)-4-ethoxy-3-(N-morpholinocarbamoyl)-1H-pyrazole;
1-(2-chlorophenyl)-5-(4-chlorophenyl)-4-methoxy-3-(N-piperidinocarbamoyl)-1H-pyrazole;
1-(2-chlorophenyl)-5-(4-chlorophenyl)-4-methoxy-3-(N-morpholinocarbamoyl)-1H-pyrazole;
1-(2-chlorophenyl)-5-(4-chlorophenyl)-4-methoxy-3-[N-(1-pyrrolidinyl)-carbamoyl]-1H-pyrazole;
1-(2-chlorophenyl)-5-(4-chlorophenyl)-4-ethoxy-3-(N-piperidinocarbamoyl)-1H-pyrazole;
1-(2-chlorophenyl)-5-(4-chlorophenyl)-4-(2-methoxy-ethoxy)-3-(N-piperidino-carbamoyl)-1H-pyrazole;
1-(2-chlorophenyl)-5-(4-chlorophenyl)-4-methoxy-3-(1-morpholinoacetyl)-1H-pyrazole;
1-(2,4-dichlorophenyl)-5-(4-chlorophenyl)-4-methoxy-3-(N-piperidino-carbamoyl)-1H-pyrazole;
1-(2,4-dichlorophenyl)-5-(4-chlorophenyl)-4-methoxy-3-[N-(1-pyrrolidinyl-carbamoyl]-1H-pyrazole;
1-(2,4-dichlorophenyl)-5-(4-chlorophenyl)-4-methoxy-3-(N-morpholino-carbamoyl)-1H-pyrazole;
1-(2,4-dichlorophenyl)-5-(4-chlorophenyl)-4-methoxy-3-[(N',N'-dimethyl-hydrazino)carbonyl]-1H-pyrazole;
1-(2,4-dichlorophenyl)-5-(4-chlorophenyl)-4-difluoromethoxy-3-[N-(1-pyrrolidinyl)carbamoyl]-1H-pyrazole;
1-(2-chloro-4-fluorophenyl)-5-(4-chlorophenyl)-4-methoxy-3-(N-morpholino-carbamoyl)-1H-pyrazole;
1-(2-chlorophenyl)-5-(4-trifluoromethylphenyl)-4-methoxy-3-[(N',N'-dimethylhydrazino)carbonyl]-1H-pyrazole;
1-(2-chlorophenyl)-5-(4-trifluoromethylphenyl)-4-methoxy-3-[N-(1-pyrrolidinyl)carbamoyl]-1H-pyrazole;
1-(2-chlorophenyl)-5-(4-trifluoromethylphenyl)-4-methoxy-3-(N-morpholino-carbamoyl)-1H-pyrazole;
1-(2-chlorophenyl)-5-(4-trifluoromethylphenyl)-4-methoxy-3-[N-(4-tetrahydro-pyranyl)carbamoyl]-1H-pyrazole;
1-(2-chlorophenyl)-5-(4-chlorophenyl)-4-methoxy-3-[N-[1-(4-fluorobenzoyl)-piperazin-4-yl]carbamoyl]-1H-pyrazole;

1-(2-chlorophenyl)-5-(4-trifluoromethylphenyl)-4-difluoromethoxy-3-[(N',N'-dimethylhydrazino)carbonyl]-1H-pyrazole;

1-(2-chlorophenyl)-5-(4-trifluoromethylphenyl)-4-difluoromethoxy-3-[N-(4-tetrahydropyranyl)carbamoyl]-1H-pyrazole;

1-(2-chlorophenyl)-5-(4-trifluoromethylphenyl)-4-difluoromethoxy-3-[N-(1-pyrrolidinyl)carbamoyl]-1H-pyrazole;

1-(2-chlorophenyl)-5-(4-chlorophenyl)-4-methoxy-3-[N-(1-pyrrolidinyl)-carbamoyl]-1H-pyrazole;

1-(2-chlorophenyl)-5-(4-chlorophenyl)-4-methoxy-3-[N-(cis-2,6-dimethyl-morpholino)carbamoyl]-1H-pyrazole;

1-(2-chlorophenyl)-5-(4-chlorophenyl)-4-methoxy-3-[N-(4,4-difluoro-piperidino)carbamoyl]-1H-pyrazole;

1-(2-chlorophenyl)-5-(4-chlorophenyl)-4-methoxy-3-[N-(4-trifluoromethyl-piperidino)carbamoyl]-1H-pyrazole;

1-(2-chlorophenyl)-5-(4-chlorophenyl)-4-methoxy-3-[(N',N'-dimethyl-hydrazino)carbonyl]-1H-pyrazole;

1-(2-chlorophenyl)-5-(4-chlorophenyl)-4-ethoxy-3-[N-(4-tetrahydropyranyl)-carbamoyl]-1H-pyrazole;

1-(2-chlorophenyl)-5-(4-trifluoromethylphenyl)-4-ethoxy-3-[(N',N'-dimethyl-hydrazino)carbonyl]-1H-pyrazole;

1-(2-chlorophenyl)-5-(4-chlorophenyl)-4-(2-methoxyethoxy)-3-[N-(4-tetrahydropyranyl)carbamoyl]-1H-pyrazole;

1-(2-chlorophenyl)-5-(4-trifluoromethylphenyl)-4-(2-methoxyethoxy)-3-[N-(1-pyrrolidinyl)carbamoyl]-1H-pyrazole;

1-(2-chlorophenyl)-5-(4-trifluoromethylphenyl)-4-(2-methoxyethoxy)-3-(N-morpholinocarbamoyl)-1H-pyrazole;

1-(2-chlorophenyl)-5-(4-chlorophenyl)-4-methoxy-3-[N-(1,1-dioxo-thiomorpholin-4-yl)carbamoyl]-1H-pyrazole;

1-(2-chlorophenyl)-5-(4-chlorophenyl)-4-methoxy-3-[N-(tetrahydrofuran-3-yl)-carbamoyl]-1H-pyrazole;

1-(2-chlorophenyl)-5-(4-chlorophenyl)-4-methoxy-3-[N-(4-benzoylpiperazin-1-yl)carbamoyl]-1H-pyrazole;

1-(2-chlorophenyl)-5-(4-chlorophenyl)-4-(n-propoxy)-3-[(N',N'-dimethyl-hydrazino)carbonyl]-1H-pyrazole;

1-(2-chlorophenyl)-5-(4-chlorophenyl)-4-methoxy-3-[N-[4-(4-chlorobenzoyl)-piperazin-1-yl]carbamoyl]-1H-pyrazole;

1-(2-chlorophenyl)-5-(4-chlorophenyl)-4-methoxy-3-[N-[4-(3-fluorobenzoyl)-piperazin-1-yl]carbamoyl]-1H-pyrazole;

1-(2-chlorophenyl)-5-(4-chlorophenyl)-4-methoxy-3-[(1,1-dioxothiomorpholin-4-yl)acetyl]-1H-pyrazole;

1-(2-chlorophenyl)-5-(4-chlorophenyl)-4-difluoromethoxy-3-[N-(1-pyrrolidinyl)carbamoyl]-1H-pyrazole;

1-(2-chlorophenyl)-5-(4-chlorophenyl)-4-difluoromethoxy-3-[(N',N'-dimethyl-hydrazino)carbonyl]-1H-pyrazole;

1-(2-chlorophenyl)-5-(4-chlorophenyl)-4-difluoromethoxy-3-[N-(4-tetrahydro-pyranyl)carbamoyl]-1H-pyrazole;

1-(2-chlorophenyl)-5-(4-chlorophenyl)-4-ethoxy-3-[N-[4-(4-fluorobenzoyl)-piperazin-1-yl]carbamoyl]-1H-pyrazole;

1-(2-chlorophenyl)-5-(4-trifluoromethylphenyl)-4-ethoxy-3-[N-[4-(4-fluoro-benzoyl)piperazin-1-yl]carbamoyl]-1H-pyrazole;

1-(2-chlorophenyl)-5-(4-chlorophenyl)-4-difluoromethoxy-3-[N-(1,1-dioxo-thiomorpholin-4-yl)carbamoyl]-1H-pyrazole;

1-(2-chlorophenyl)-5-(4-chlorophenyl)-4-methoxy-3-[N-[4-(3-chlorobenzoyl)-piperazin-1-yl)carbamoyl]-1H-pyrazole;

1-(2-chlorophenyl)-5-(4-chlorophenyl)-4-methoxy-3-[N-[4-(2-chlorobenzoyl)-piperazin-1-yl]carbamoyl]-1H-pyrazole;

1-(2-chlorophenyl)-5-(4-chlorophenyl)-4-methoxy-3-[N-[4-(3,4-difluoro-benzoyl)piperazin-1-yl]carbamoyl]-1H-pyrazole;

1-(2-chlorophenyl)-5-(4-chlorophenyl)-4-methoxy-3-[N-[4-(2,4-difluoro-benzoyl)piperazin-1-yl]carbamoyl]-1H-pyrazole;

1-(2-chlorophenyl)-5-(4-chlorophenyl)-4-methoxy-3-[N-[4-(3,5-difluoro-benzoyl)piperazin-1-yl]carbamoyl]-1H-pyrazole;

1-(2-chlorophenyl)-5-(4-chlorophenyl)-4-methoxy-3-[N-[4-(4-fluorophenyl)-piperazin-1-yl]carbamoyl]-1H-pyrazole;

1-(2-chlorophenyl)-5-(4-chlorophenyl)-4-methoxy-3-[N-(3-trifluoromethyl-pyrrolidin-1-yl)carbamoyl]-1H-pyrazole;

1-(2,4-dichlorophenyl)-5-(4-trifluoromethylphenyl)-4-methoxy-3-[N',N'-dimethylhydrazino)carbonyl]-1H-pyrazole;

1-(2,4-dichlorophenyl)-5-(4-trifluoromethylphenyl)-4-methoxy-3-[N-(morpholino)carbamoyl]-1H-pyrazole;

1-(2,4-dichlorophenyl)-5-(4-trifluoromethylphenyl)-4-methoxy-3-[N-(1,1-dioxo-2-tetrahydrothienyl)carbamoyl]-1H-pyrazole;

1-(2-chloro-4-fluorophenyl)-5-(4-trifluoromethylphenyl)-4-methoxy-3-[N-(4-tetrahydropyranyl)carbamoyl]-1H-pyrazole;

1-(2-chlorophenyl)-5-(4-trifluormethylphenyl)-4-methoxy-3-[N-(1,1-dioxothiomorpholino)carbamoyl]-1H-pyrazole;

1-(2-chlorophenyl)-5-(4-chlorophenyl)-4-methoxy-3-[N-(4-fluoropiperidino)-carbamoyl]-1H-pyrazole;

1-(2,4-dichlorophenyl)-5-(4-chlorophenyl)-4-methoxy-3-[N-(4-benzoyl-piperazin-1-yl)carbamoyl]-1H-pyrazole;

1-(2,4-dichlorophenyl)-5-(4-chlorophenyl)-4-methoxy-3-[N-[4-(2,4-difluoro-benzoyl)piperazin-1-yl]carbamoyl]-1H-pyrazole;

5-(4-chlorophenyl)-1-(2-fluorophenyl)-4-methoxy-3-[N-(4,4-difluoro-piperidino)carbamoyl]-1H-pyrazole;

1-(2-chlorophenyl)-5-(4-trifluoromethylphenyl)-4-methoxy-3-[N-(4,4-difluoro-piperidino)carbamoyl]-1H-pyrazole;

1-(2,4-dichlorophenyl)-5-(4-trifluoromethylphenyl)-4-methoxy-3-[N-(4,4-difluoropiperidino)carbamoyl]-1H-pyrazole;

5-(4-chlorophenyl)-1-(2-fluorophenyl)-4-methoxy-3-[N-[3-(trifluoromethyl)-pyrrolidin-1-yl]carbamoyl]-1H-pyrazole;

1-(2-chlorophenyl)-5-(4-chlorophenyl)-4-difluoromethoxy-3-[N-(4,4-difluoro-piperidino)carbamoyl]-1H-pyrazole;

5-(4-chlorophenyl)-1-(2-fluorophenyl)-4-methoxy-3-[N-[4-(4-chlorophenyl)-piperazin-1-yl]carbamoyl]-1H-pyrazole; and 5-(4-chlorophenyl)-1-(2-fluorophenyl)-4-methoxy-3-[N-[4-(4-fluorophenyl)-piperazin-1-yl]carbamoyl]-1H-pyrazole;

or a pharmaceutically acceptable salt thereof.

4. A pharmaceutical composition comprising as an active ingredient a pyrazole compound of the formula [I]:

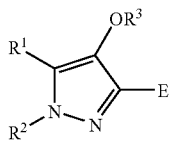

wherein
- $R^1$ is a phenyl group substituted by one to two groups selected from a halogen atom and a trihalogeno-$C_{1-4}$ alkyl group,
- $R^2$ is a phenyl group substituted by one to two halogen atoms,
- $R^3$ is a $C_{1-4}$ alkyloxy-$C_{1-4}$ alkyl group or an alkyl group optionally substituted by one to three halogen atoms,
- E is a group of the following formula:

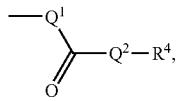

- $Q^1$ is a single bond,
- $Q^2$ is a single bond or a $C_{1-4}$ alkylene group,
- $R^4$ is a saturated or unsaturated 5- to 6-membered heteromonocyclic group optionally substituted by one to three groups selected from an oxo group or a group of the formula: —NH($R^6$), and
- $R^6$ is (i) a saturated or unsaturated 5- to 7-membered heteromonocyclic group optionally substituted by one to three groups selected from the group consisting of a halogen atom, a $C_{1-4}$ alkyl group optionally substituted by one to three halogen atoms, a phenyl group optionally substituted by one to two halogen atoms, and an acyl group or (ii) an amino group optionally substituted by one to two $C_{1-4}$ alkyl groups, or a pharmaceutically acceptable salt thereof.

5. The pharmaceutical composition according to claim 4 which is an agent for treatment of obesity.

6. The pharmaceutical composition according to claim 4 which is an agent for treatment of anxiety disorder or appetite disorder.

7. The pharmaceutical composition according to claim 6, wherein the appetite disorder is bulimarexia or anorexia.

* * * * *